United States Patent
Arai et al.

(10) Patent No.: US 10,842,431 B2
(45) Date of Patent: Nov. 24, 2020

(54) MENTAL ILLNESS DETERMINATION DEVICE

(71) Applicants: DAIKIN INDUSTRIES, LTD., Osaka (JP); TOKYO INSTITUTE OF TECHNOLOGY, Tokyo (JP); NATIONAL UNIVERSITY CORPORATION TOTTORI UNIVERSITY, Tottori (JP)

(72) Inventors: Junichiro Arai, Osaka (JP); Akira Matsubara, Osaka (JP); Takahiro Hirayama, Osaka (JP); Hideki Hashizume, Osaka (JP); Takashi Gotou, Osaka (JP); Yasunori Kotani, Tokyo (JP); Yoshimi Ohgami, Tokyo (JP); Taro Tomatsu, Tokyo (JP); Koichi Kaneko, Yonago (JP); Katsutoshi Yokoyama, Yonago (JP); Hiroshi Matsumura, Yonago (JP); Shenghong Pu, Yonago (JP); Masashi Itakura, Yonago (JP); Hiroaki Ohdachi, Yonago (JP); Masaru Ueki, Yonago (JP); Shinya Masuda, Yonago (JP)

(73) Assignees: Daikin Industries, Ltd., Osaka (JP); Tokyo Institute of Technology, Tokyo (JP); National University Corporation Tottori University, Tottori (JP)

( * ) Notice: Subject to any disclaimer, the term of this patent is extended or adjusted under 35 U.S.C. 154(b) by 0 days.

(21) Appl. No.: 16/468,663

(22) PCT Filed: Dec. 12, 2017

(86) PCT No.: PCT/JP2017/044545
§ 371 (c)(1),
(2) Date: Jun. 11, 2019

(87) PCT Pub. No.: WO2018/110544
PCT Pub. Date: Jun. 21, 2018

(65) Prior Publication Data
US 2019/0298244 A1    Oct. 3, 2019

(30) Foreign Application Priority Data
Dec. 12, 2016   (JP) .................. 2016-240737

(51) Int. Cl.
*A61B 5/00* (2006.01)
*A61B 5/01* (2006.01)
(Continued)

(52) U.S. Cl.
CPC ............ *A61B 5/165* (2013.01); *A61B 5/0075* (2013.01); *A61B 5/0077* (2013.01); *A61B 5/026* (2013.01);
(Continued)

(58) Field of Classification Search
CPC ......... A61B 5/165; A61B 5/026; A61B 5/163; A61B 5/0075; A61B 5/0077;
(Continued)

(56) References Cited

U.S. PATENT DOCUMENTS

2004/0210159 A1* 10/2004 Kibar ..................... G16H 20/70
600/558
2006/0116555 A1   6/2006 Pavlidis et al.
(Continued)

FOREIGN PATENT DOCUMENTS

| CN | 105559802 A | 5/2016 |
| JP | 2012-34839 A | 2/2012 |

(Continued)

OTHER PUBLICATIONS

Puri et al., "StressCann: Non-contact Measurement of Users' Emotional States through Thermal Imaging" CHI 2005, Apr. 2-7, 2005, Portland, Oregon, USA pp. 1725-1728 (Year: 2005).*
(Continued)

*Primary Examiner* — Boniface N Nganga
(74) *Attorney, Agent, or Firm* — Global IP Counselors, LLP

(57) ABSTRACT

A mental illness determination device includes a face change information acquisition unit and a mental illness determination unit. The face change information acquisition unit is configured to acquire face change information indicating a time-series change in face data of a subject when emotional stimulation information for stimulating any sense or any combination of senses among an auditory sense, an olfactory sense, a gustatory sense, a tactile sense, and a somatic sensation of the subject to change emotion, and is divided into positive information for increasing comfort and nega-
(Continued)

tive information for decreasing comfort is provided to the subject. The mental illness determination unit is configured to determine a state of mental illness of the subject on the basis of the face change information.

13 Claims, 40 Drawing Sheets

(51) Int. Cl.
*A61B 5/026* (2006.01)
*A61B 5/16* (2006.01)
*A61B 5/0476* (2006.01)
*A61B 10/00* (2006.01)

(52) U.S. Cl.
CPC ............ *A61B 5/0476* (2013.01); *A61B 5/163* (2017.08); *A61B 5/168* (2013.01); *A61B 5/4064* (2013.01); *A61B 10/00* (2013.01); *A61B 5/0064* (2013.01); *A61B 5/01* (2013.01); *A61B 5/167* (2013.01); *A61B 5/743* (2013.01); *A61B 2562/0233* (2013.01); *A61B 2562/046* (2013.01)

(58) Field of Classification Search
CPC ..... A61B 5/0476; A61B 5/168; A61B 5/4064; A61B 5/0064; A61B 5/01; A61B 5/167; A61B 5/743; A61B 5/015; A61B 5/7275; A61B 2562/0233; A61B 2562/046; A61B 10/00; G06K 9/00221
See application file for complete search history.

(56) References Cited

U.S. PATENT DOCUMENTS

| | | | |
|---|---|---|---|
| 2006/0187305 A1* | 8/2006 | Trivedi | G06K 9/00234 348/169 |
| 2009/0080730 A1* | 3/2009 | Pavlidis | G06K 9/00268 382/128 |
| 2014/0200416 A1 | 7/2014 | Kashef et al. | |
| 2014/0315168 A1 | 10/2014 | Movellan et al. | |
| 2017/0281070 A1 | 10/2017 | Arai et al. | |

FOREIGN PATENT DOCUMENTS

| | | |
|---|---|---|
| JP | 2013-176406 A | 9/2013 |
| WO | 2016/035719 A1 | 3/2016 |
| WO | 2016035719 A1 | 3/2016 |

OTHER PUBLICATIONS

International Search Report of corresponding PCT Application No. PCT/JP2017/044545 dated Feb. 13, 2018.
International Preliminary Report of corresponding PCT Application No. PCT/JP2017/044545 dated Jun. 27, 2019.
European Search Report of corresponding EP Application No. 17 88 1403.4 dated Nov. 27, 2019.

* cited by examiner

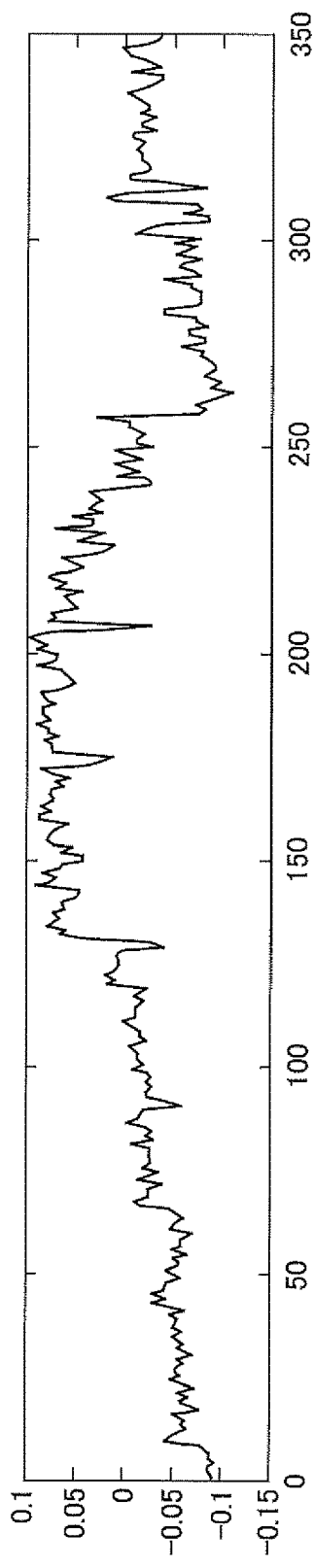
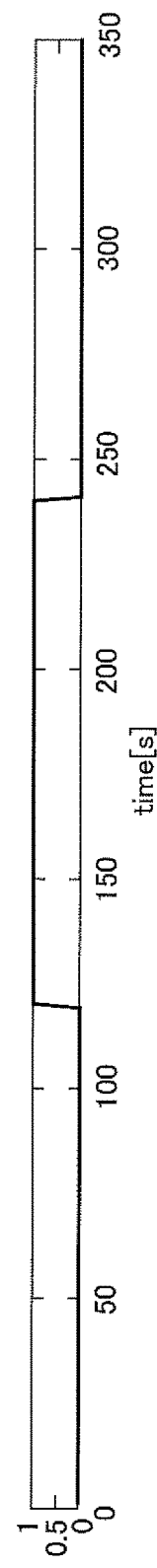
FIG. 36A
FIG. 36B

MENTAL ILLNESS DETERMINATION DEVICE

CROSS-REFERENCE TO RELATED APPLICATIONS

This U.S. National stage application claims priority under 35 U.S.C. § 119(a) to Japanese Patent Application No. 2016-240737, filed in Japan on Dec. 12, 2016, the entire contents of which are hereby incorporated herein by reference.

TECHNICAL FIELD

The present invention relates to a mental illness determination device.

BACKGROUND ART

In recent years, attempts have been made to estimate brain activity of persons by utilizing data detected using electroencephalography (EEG), magnetic resonance imaging (fMRI: functional Magnetic Resonance Imaging), and near-infrared spectroscopy (NIRS) such as disclosed in (Japanese Unexamined Patent Application Publication No. 2013-176406. Further, applications have been studied such as determination of physical and mental health status of persons from their estimated brain activity.

SUMMARY

However, electroencephalography and near-infrared spectroscopy require preprocessing such as making a subject wear electrodes. Also, magnetic resonance imaging requires measurement within a predetermined MRI room. In short, the methods described above have problems such as complex preparatory work or limited measurement conditions. In addition, all of the methods described above require huge cost. Consequently, the methods described above make it difficult to perform operations such as determining the physical and mental health status of the subject in some times.

The issue to be addressed by the present invention is to provide an apparatus and method for facilitating determination of a mental or physical physiological state of a subject. In particular, it is an object of the present invention to provide a mental illness determination device for facilitating determination of a state of mental illness of a subject.

A mental illness determination device according to a first aspect of the present invention includes an emotional stimulation information providing unit, a face change information acquisition unit, a face change information decomposition unit, a determination component extraction unit, and a mental illness determination unit. The emotional stimulation information providing unit provides emotional stimulation information for stimulating any sense or any combination of senses among an auditory sense, an olfactory sense, a gustatory sense, a tactile sense, and a somatic sensation of a subject to change emotion. The face change information acquisition unit acquires face change information indicating a time-series change in face data of the subject. The face change information decomposition unit decomposes the face change information into a plurality of components by using singular value decomposition, principal component analysis, or independent component analysis. The determination component extraction unit extracts a component related to the emotional stimulation information from the plurality of components as a determination component. The mental illness determination unit determines a state of mental illness of the subject on the basis of the determination component.

In the mental illness determination device according to the first aspect, a determination component is extracted from a plurality of components obtained by subjecting the face change information to the singular value decomposition, the principal component analysis, or the independent component analysis. This can facilitate estimation of the presence of brain activity of the subject without using electrodes or the like that require preprocessing before attachment. Accordingly, a state of mental illness of the subject can be easily determined on the basis of the determination component corresponding to the brain function of the subject.

A mental illness determination device according to a second aspect of the present invention is the mental illness determination device of the first aspect, wherein the emotional stimulation information providing unit provides, together with the emotional stimulation information, emotional image information for stimulating a visual sense of the subject to change emotion.

In the mental illness determination device according to the second aspect, stimulating different brain regions enables the determination of various types of mental illnesses. For example, using information for stimulating the visual sense, diseases related to the occipital region of the brain can be diagnosed. Using information for stimulating the auditory sense, diseases related to the temporal region and the frontal region of the brain can be diagnosed. Moreover, using information on a face image, dementia and autism can be diagnosed. Using voice audio information, anxiety disorders can be diagnosed.

A mental illness determination device according to a third aspect of the present invention is the mental illness determination device of the first aspect or the second aspect, wherein the determination component extraction unit extracts the determination component on the basis of a correlation value between a determination waveform corresponding to the emotional stimulation information and each of the plurality of components. This configuration can specify the determination component corresponding to the brain function of the subject.

A mental illness determination device according to a fourth aspect of the present invention is the mental illness determination device of the third aspect, wherein a modified wave that takes the human physiological response into account is used as the determination waveform. The determination waveform, when found to have a significant correlation with a component obtained from the face change information, shows a high correlation value, and thus the accuracy of the extraction of the determination component can be enhanced.

A mental illness determination device according to a fifth aspect of the present invention is the mental illness determination device of the fourth aspect, wherein the determination waveform is displaced after a predetermined time elapses, after the provision of the emotional stimulation information. A slight delay of the phase relative to the response of the brain provides accurate correlation.

A mental illness determination device according to a sixth aspect of the present invention is the mental illness determination device of the fourth or fifth aspect, wherein the determination waveform is a rectangular wave. A rectangular wave can be adjusted depending on whether emotional stimulation information is being provided, and thus the determination component can be easily extracted.

A mental illness determination device according to a seventh aspect of the present invention is the mental illness determination device of the fourth or fifth aspect, wherein the determination waveform is generated from a plurality of waveforms determined by calculating a component found to have a correlation among the plurality of components and performing calculation of the component a plurality of times. The determination waveform is optimized using previous history, and, thus, shows a high correlation value when the determination waveform is found to have a significant correlation with a component obtained from the face change information. This can enhance the accuracy of the extraction of the determination component.

A mental illness determination device according to an eighth aspect of the present invention is the mental illness determination devices of the first to seventh aspects, wherein the mental illness determination unit determines the state of mental illness on the basis of any one or any combination of an amount of change falling within a predetermined range for the determination component with respect to a reference value, a value obtained by performing multiple regression analysis on the determination component, an area of a region for which the determination waveform is generated, an average value of the determination waveform, and a value for a center of gravity of the determination waveform. This enables the determination of mental illness using an optimum technique in accordance with the calculation capabilities of the device. In addition, an optimum technique can be employed in accordance with the type of mental illness.

A mental illness determination device according to a ninth aspect of the present invention is the mental illness determination devices of the first to eighth aspects, further including an autonomic nervous activity measurement unit that measures autonomic nervous activity of the subject. The mental illness determination unit determines a type of the state of the mental illness on the basis of the autonomic nervous activity.

In the mental illness determination device according to the ninth aspect, the ratio of a response to emotional stimulation, which is derived from the autonomic nervous system, to a response to emotional stimulation, which is derived from brain activity, is determined. This enables the determination of the type of disease. Examples of the type of disease that can be determined include "depressive disorder/major depressive disorder, dysthymic disorder, depressive disorder not otherwise specified, depression-related syndrome", "bipolar disorder/bipolar I disorder, bipolar II disorder", "schizophrenia", "developmental disability/pervasive developmental disorders (autism, Asperger's syndrome, Tourette syndrome), learning disability LD, attention deficit hyperactivity disorder ADHD", "mental retardation", "anxiety disorder/generalized anxiety disorder, panic disorder, social anxiety disorder, obsessive-compulsive disorder, dissociative disorder, adjustment disorder", "dementia/Alzheimer-type dementia, vascular dementia, dementia with Lewy bodies, frontotemporal dementia", "substance use disorder", "organic mental illness, including the symptomatic ones", "epilepsy", and "personality disorder".

A mental illness determination device according to a tenth aspect of the present invention is the mental illness determination devices of the second to ninth aspects, further including a line-of-sight measurement unit that measures a line of sight of the subject. The mental illness determination unit removes a low-reliability determination result on the basis of the line of sight of the subject.

In the mental illness determination device according to the tenth aspect, by determining whether the subject is recognizing image information, a low-reliability determination result can be removed.

A mental illness determination device according to an eleventh aspect of the present invention includes an emotional stimulation information providing unit, a face change information acquisition unit, a face change information decomposition unit, a determination component extraction unit, and a mental illness determination unit. The emotional stimulation information providing unit provides emotional stimulation information for stimulating a sense of the subject to change emotion. The face change information acquisition unit acquires face change information indicating a time-series change in face data of the subject. The face change information decomposition unit decomposes the face change information into a plurality of components by using singular value decomposition, principal component analysis, or independent component analysis. The determination component extraction unit extracts a determination component on the basis of the intensity of correlation between a determination waveform corresponding to the emotional stimulation information and each of the plurality of components. The mental illness determination unit determines a state of mental illness of the subject on the basis of the determination component. The determination waveform is generated from a plurality of waveforms determined by calculating a component found to have a correlation among the plurality of components and performing calculation of the component a plurality of times.

In the mental illness determination device according to the eleventh aspect, the determination waveform is optimized using previous history. With the use of the determination waveform, which shows a high correlation value when the determination waveform is found to have a significant correlation with a component obtained from the face change information, the accuracy of the extraction of the determination component can be enhanced.

A mental illness determination device according to a twelfth aspect according to the present invention is the mental illness determination devices of the first to eleventh aspects, wherein the mental illness determination unit calculates a correlation value of the determination component for the emotional stimulation information, and determines a state level of mental illness of the subject on the basis of the calculated correlation value and determination information. Here, a determination information providing device on a network includes a determination information storage unit that stores, the amount of change falling within a predetermined range between a correlation value of a determination component calculated for emotional stimulation information and a reference correlation value of a reference determination component calculated for the emotional stimulation information, as the determination information, in association with a state level of mental illness.

In the mental illness determination device according to the twelfth aspect, the state level of the mental illness of the subject can be determined by using the determination information providing device on the network.

In the mental illness determination device according to the first aspect, a state of mental illness of a subject can be easily determined.

In the mental illness determination device according to the second aspect, various types of mental illnesses can be determined.

In the mental illness determination device according to the third aspect, a determination component corresponding to the brain function of the subject can be specified.

In the mental illness determination device according to the fourth aspect, the accuracy of the extraction of a determination component can be enhanced.

In the mental illness determination device according to the fifth aspect, accurate correlation can be obtained.

In the mental illness determination device according to the sixth aspect, a determination component can be easily extracted.

In the mental illness determination device according to the seventh aspect, the accuracy of the extraction of a determination component can be enhanced.

In the mental illness determination device according to the eighth aspect, mental illness can be determined by using an optimum technique.

In the mental illness determination device according to the ninth aspect, a type of disease can be determined.

In the mental illness determination device according to the tenth aspect, a low-reliability determination result can be removed.

In the mental illness determination device according to the eleventh aspect, the accuracy of the extraction of a determination component can be enhanced.

In the mental illness determination device according to the twelfth aspect, a state level of mental illness of the subject can be determined by using a determination information providing device on a network.

BRIEF DESCRIPTION OF THE DRAWINGS

FIGS. 36A and 36B are diagrams illustrating the waveform of a determination component when a negative image is presented.

DETAILED DESCRIPTION OF EMBODIMENT(S) EMBODIMENTS

Figure 1B:
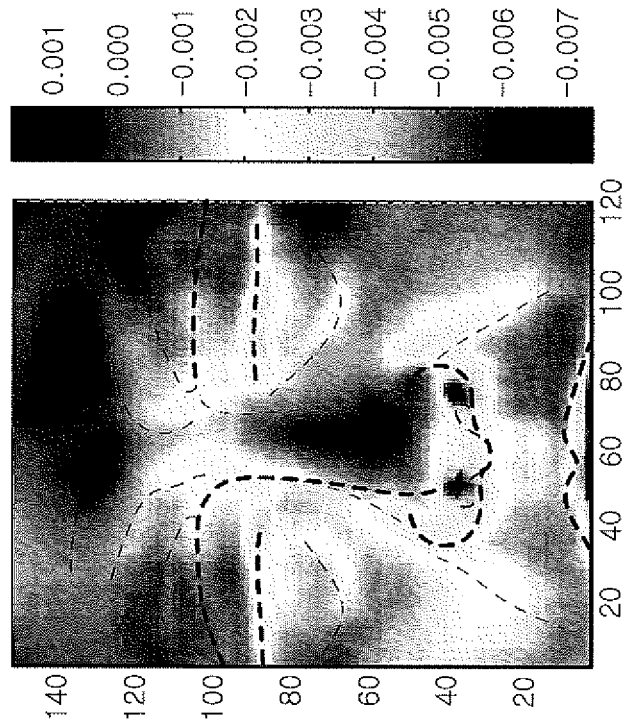
FIGS. 1A and 1B are diagrams illustrating an example of captured image data and the result of analyzing the captured image data.

Before the description of an embodiment of the present invention, findings obtained by the inventors will be described first, which are the important basis of the present invention made by the inventors.

(1) Summary of Findings Obtained by the Inventors

It is known that human brain activity reflects human intellectual activity (such as cognitive activity) and emotional activity (activity such as with comfort/discomfort). Hitherto, attempts have been made to estimate human brain activity, in which case data detected using any method among electroencephalography, magnetic resonance imaging, and near-infrared spectroscopy is generally used.

For example, when electroencephalography is employed as a detection method, electroencephalogram electrodes need to be attached to the test subject. When electroencephalogram electrodes are attached, it is necessary to reduce resistance between the skin and the electrodes. Accordingly, operations are required, such as a process to abrade the skin and an application of a paste to the electrodes. When magnetic resonance imaging is employed, measurement at a location other than an MRI room is impossible, and, in addition, there are limited measurement conditions such as allowing no metal within the measurement room. When near-infrared spectroscopy is employed, a probe needs to be attached to the test subject. In some cases, wearing a probe for a long time makes the test subject feel pain, or accurate detection is not attained depending on the state of contact between the probe and the test subject's hair. Accordingly, when an existing detection method is employed to measure human brain activity, a great load is imposed on the test subject. For example, preprocessing is required when the electroencephalogram electrodes, the probe, or the like is attached, or there are limited measurement conditions.

It is therefore desirable to develop a means to reduce the load on the test subject and to facilitate estimation of human brain activity.

The inventors have considered the possibility of estimating human brain activity on the basis of the facial skin temperature of a person or on the basis of the condition of facial blood circulation considered to be proportional to the facial skin temperature. The facial skin temperature of a person can be acquired by using a measurement device such as a thermography device, and the condition of facial blood circulation, that is, the amount of facial blood circulation, can be estimated from RGB data of a captured face image obtained by using an imaging device. Accordingly, the facial skin temperature or a captured face image can be acquired without attachment of sensors that require processing before attachment, such as electroencephalogram electrodes or a probe.

On the other hand, it is known that the facial skin temperature of a person changes due to various factors such as ambient temperature and/or autonomic nervous activity. For this reason, if brain activity is to be estimated on the basis of the facial skin temperature or on the basis of the amount of facial blood circulation considered to be proportional to the facial skin temperature, it is considered very difficult to determine whether the acquired data reflects only brain activity.

As a result of intensive studies, the inventors have found that a component indicating a facial skin temperature change, or a change in the amount of facial blood circulation, that reflects brain activity can be identified by detecting facial skin temperatures, decomposing time-series facial skin temperature data, which includes detected temperature data and location data (coordinate data) of a detection region, or time-series facial blood-circulation-amount data calculated on the basis of RGB data obtained from time-series captured face image data, into a plurality of components by using singular value decomposition, principal component analysis, or independent component analysis, and analyzing the plurality of components obtained by decomposition. Then, the inventors have arrived at the present invention in which by estimating and analyzing the brain activity of the subject, the physiological state of the subject can be visualized on the basis of the estimated brain activity.

(2) Method for Acquiring Various Face Data and Method for Analyzing Acquired Various Data (2-1) Method for Acquiring Facial Skin Temperature Data and Method for Analyzing Facial Skin Temperature Data Next, a method for acquiring facial skin temperature data and a method for analyzing facial skin temperature data, which are used by the inventors to obtain the findings described above, will be described.

In this test, facial skin temperature data was acquired from six test subjects. Specifically, the test subjects were seated in chairs placed in an artificial climate room maintained at a room temperature of 25° C., and facial skin temperature data was acquired from the entire areas of the faces of the test subjects by using an infrared thermography device. The infrared thermography device is a device capable of detecting infrared radiation energy emitted from a target object by using an infrared camera, converting the detected infrared radiation energy into temperatures (here, temperatures expressed in degrees Celsius) on the surface of the target object, and displaying and storing the distribution of the temperatures as facial skin temperature data (e.g., image data indicating the distribution of the temperatures). In the test, R300, manufactured by NEC Avio Infrared Technologies Co., Ltd., was used as the infrared thermography device. The infrared camera was placed in front of the test subjects at a distance of 1.5 m from the test subjects. The facial skin temperature data was acquired for 30 minutes.

In the test, furthermore, the test subjects were presented with a brain function activation exercise during the acquisition of the facial skin temperature data. Accordingly, facial skin temperature data during a brain deactivation time and facial skin temperature data during a brain activation time were acquired. Examples of the brain function activation exercise include psychological tasks such as causing each test subject to perform calculations, recognize numbers, shapes, and colors, or memorize symbols, characters, or words on the basis of video images displayed on a display device or the like. In this test, "mental multiplication" was employed as a brain function activation exercise. Each test subject was assigned tasks of calculating written numbers displayed on the display device and inputting the answers by using a keyboard. In the test, the brain function activation exercise was presented to the test subjects for a duration of 10 minutes after the lapse of 5 minutes from the start of acquisition of the facial skin temperature data.

As the analysis of the facial skin temperature data, the acquired facial skin temperature data was subjected to the singular value decomposition using SVD (Singular Value Decomposition) of MATLAB (registered trademark) as an analysis tool. The singular value decomposition was performed on all the pieces of facial skin temperature data acquired in time series (30-minute data), in which the factor was time data obtained at intervals of 30 seconds (60 time points within 30 minutes) and the measure was the facial skin temperature data (240×320 pixels) within the period (a period of 30 seconds). Through the singular value decomposition, facial skin temperature data X was decomposed into a plurality of components, and a temporal distribution V and a spatial distribution U of each of the components, and a singular value S indicating the magnitude of each component were calculated. The relationship among them is represented by a formula below. In the formula, V' denotes a matrix in which the rows and columns of V are transposed.

$$X = (U \cdot S) \cdot V^* \quad \text{[Formula. 1]}$$

The temporal distribution V and the spatial distribution U of each component determined using the singular value decomposition were plotted on a graph, and a component waveform diagram and a temperature distribution diagram of each component were created.

Further, the created component waveform diagram and temperature distribution diagram of each component were analyzed to identify a component indicating a skin temperature change reflecting brain activity.

The component waveform diagram of each component was analyzed to determine the existence of a correlation between the amplitude of the component waveform of the component and each of the brain deactivation time and the brain activation time. Specifically, an evaluation was made of whether a correlation existed between the amplitude shown in the component waveform diagram of each component and the brain deactivation period/brain activation period. In this test, within the period during which the facial skin temperature data was acquired, the period during which no brain function activation exercise was presented to the test subjects, which was equal to a period of 5 minutes from the start of data acquisition until the elapse of 5 minutes and a period of 15 minutes from the time of elapse of 15 minutes after the start of data acquisition until the end of data acquisition, was set as the brain deactivation time, and the period during which the test subjects were presented with a brain function activation exercise, which was equal to a period of 10 minutes from the time of elapse of 5 minutes after the start of data acquisition until the elapse of 10 minutes, was set as the brain activation time. Then, an evaluation was made of the existence of a correlation between the amplitude shown in the component waveform diagram of each component and each of the brain deactivation time and the brain activation time. The determination of the existence of a correlation was performed using statistical correlation analysis. When the significance level (a) was 0.05 or less, it was determined that a correlation existed.

The temperature distribution diagram of each component was analyzed for the presence of a temperature change in a predetermined face region. The brain has a mechanism for cooling the brain while leaving the body temperature unchanged, called a selective brain cooling system. The selective brain cooling system is known to dissipate heat generated by brain activity through a forehead portion and a paranasal-sinus surrounding area (including the glabella and an area around a nose portion). In this test, accordingly, an evaluation was made of whether a temperature change occurred in the paranasal-sinus surrounding area and the forehead portion on the temperature distribution diagram of each component. The presence of a temperature change in the paranasal-sinus surrounding area and the forehead portion on the temperature distribution diagram was determined by determining the presence of a temperature change by visual inspection or by determining whether the temperature of the paranasal-sinus surrounding area and the forehead portion was different from the average temperature of the overall measurement data by one standard deviation (SD) or more.

The determination of the polarity (plus or minus) of the facial skin temperature data X is based on the relationship among the values of the spatial distribution U, the singular value S, and the temporal distribution V. Accordingly, in some times, the polarity appears to be reversed on the component waveform diagram and temperature distribution diagram of each component. For this reason, the polarity is assumed to be excluded from the evaluation of the component waveform diagram and the temperature distribution diagram.

In the infrared thermography device, as described above, infrared radiation energy detected from a target object is converted into temperatures and the distribution of the temperatures is used as facial skin temperature data. When an infrared thermography device is used for a person to acquire the facial skin temperature of the person, a temperature change (so-called noise) that is not related to various brain activities such as movement of the face and/or autonomic nervous activity may also be acquired as facial skin temperature data (see FIG. 1A). To detect the temperature change not related to brain activity, relative facial skin temperature data was created such that all the average values of the pieces of temperature data included in facial skin temperature data obtained at intervals of 30 seconds were set to "0". The created facial skin temperature data was also subjected to the singular value decomposition using SVD of MATLAB (registered trademark) as an analysis tool to create a component waveform diagram and temperature distribution diagram of each component corresponding to the singular value S, which were analyzed to identify a component indicating a skin temperature change reflecting brain activity.

In the following, for convenience of description, facial skin temperature data acquired using an infrared thermography device is referred to as "facial skin temperature data corresponding to temperature conversion data", and relative facial skin temperature data in which all the average values of the pieces of temperature data included in facial skin temperature data corresponding to temperature conversion data obtained at intervals of a predetermined time (in this test, at intervals of 30 seconds) are set to "0" is referred to as "facial skin temperature data corresponding to relative temperature conversion data".

One of the six test subjects was also subjected to, in addition to the detection of the facial skin temperature by using an infrared thermography device, measurement of brain waves by connecting electrodes on the scalp of the test subject to also evaluate the correlation between the amplitude of the β wave (a brain wave in a frequency range of 14 to 30 Hz), which is known as a waveform that appears when people are awake or tense, and the amplitude shown in the component waveform diagram. In the measurement of the brain waves, the electrodes were placed at six locations (F3, F4, C3, C4, Cz, and Pz) based on the International 10-20 system.

While each test subject is presented with a brain function activation exercise, the head of the test subject may be moved upward and downward. This movement causes a change in the position of the face of the test subject relative to the infrared camera. To verify whether the change in the position of the face affects a skin temperature change, a contrast test was performed on one test subject. In a contrast test for verifying the influence of the movement of a test subject on the acquisition of facial skin temperature data, facial skin temperature data of the test subject was acquired by using an infrared thermography device in a way similar to that in the test described above. The test subject was also required to press the keyboard buttons at random timing while no brain function activation exercise was presented (i.e., the brain deactivation time). The facial skin temperature data corresponding to temperature conversion data and the facial skin temperature data corresponding to relative temperature conversion data, which were obtained by this contrast experiment, were also be subjected to the singular value decomposition using SVD of MATLAB (registered trademark) as an analysis tool to create a component waveform diagram and temperature distribution diagram of each component corresponding to the singular value S, which were analyzed to identify a component indicating a skin temperature change reflecting brain activity.

Figure 1A:
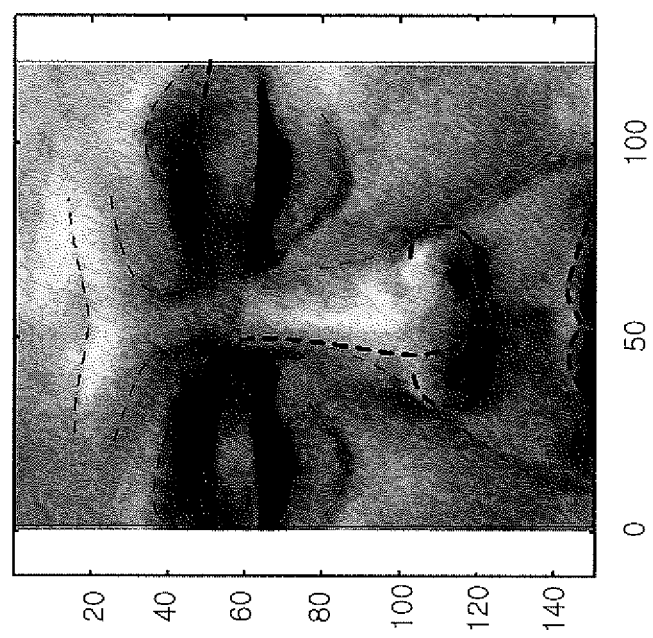

(2-2) Method for Acquiring Captured Face Image Data and Method for Analyzing Captured Face Image Data FIG. 1A is a diagram illustrating an example of captured image data of the paranasal-sinus surrounding area of the face of a test subject, which is captured using an imaging device. FIG. 1B is a diagram illustrating an example blood circulation amount distribution diagram (image map).

Next, a method for acquiring captured face image data and a method for analyzing captured face image data, which are used by the inventors to obtain the findings described above, will be described.

In this test, captured face image data was acquired from six test subjects. Specifically, the test subjects were seated in chairs placed in an artificial climate room maintained at a room temperature of 25° C., and captured image data of the paranasal-sinus surrounding areas of the entire areas of the faces of the test subjects was acquired in time series by using an imaging device capable of acquiring images in time series.

On the basis of the selective brain cooling system described above, a change in the amount of facial blood circulation considered to be proportional to the facial skin temperature that changes with brain activity is considered to occur in the forehead portion and/or the paranasal-sinus surrounding area. Accordingly, the inventors have considered that capturing a change in the amount of facial blood circulation in at least the forehead portion and/or the paranasal-sinus surrounding area enables accurate estimation of brain activity. In this test, captured image data of the paranasal-sinus surrounding area of the face of each test subject was acquired in time series.

In this test, furthermore, an imaging device installed on the liquid crystal display screen side of iPad Air (registered trademark), manufactured by Apple Inc., was used as an imaging device, and color moving image data was acquired as time-series captured image data. The imaging device was placed in front of the test subjects at a distance of 1.0 m from the test subjects. Then, the imaging device continuously captured image data for 30 minutes along the time axis in periods of 30 frames per second to obtain moving image data of the faces.

In this test, moreover, the test subjects were presented with a brain function activation exercise during the acquisition of the moving image data of the faces. Accordingly, moving image data of the faces at the brain deactivation time and moving image data of the faces at the brain activation time were acquired. In the test, as in the test described above, "mental multiplication" was employed as a brain function activation exercise. Each test subject was assigned tasks of calculating written numbers displayed on the display device and inputting the answers by using a keyboard. In the test, the brain function activation exercise was presented to the test subjects for a duration of 10 minutes after the lapse of 5 minutes from the start of acquisition of the moving image data of the faces.

As the analysis of the moving image data of the faces, blood-circulation-amount data was calculated on the basis of RGB data obtained from the captured moving image data of the faces, and the calculated time-series blood-circulation-amount data was subjected to the singular value decomposition using SVD of MATLAB (registered trademark) as an analysis tool. Here, an erythema index "a*" having a correlation with redness of the skin or the amount of hemoglobin, which was computed from RGB data of an image, was determined in accordance with the CIE-L*a*b* color system, and was defined as blood-circulation-amount data. The singular value decomposition was performed on the blood-circulation-amount data (here, the erythema index) based on RGB data obtained from all the pieces of moving image data acquired in time series (30-minute data), in which the factor was time data obtained at intervals of 30 seconds (60 time points within 30 minutes) and the measure was the erythema index computed from the RGB data for the period (at intervals of 30 seconds) (the erythema index computed from the average value of RGB values obtained from 1-second frame data extracted every 30 seconds; 240×320 pixels). Through the singular value decomposition, time-series blood-circulation-amount data based on the RGB data obtained from the moving image data of the faces is decomposed into a plurality of components, and a temporal distribution V and a spatial distribution U of each of the components, and a singular value S indicating the magnitude of each component were calculated. The relationship among them is represented by a formula similar to the formula above (Formula. 1).

The temporal distribution V and the spatial distribution U of each component determined using the singular value decomposition were plotted on a graph, and a component waveform diagram and a blood circulation amount distribution diagram of each component were created.

Further, the created component waveform diagram and blood circulation amount distribution diagram of each component were analyzed to identify a component indicating a change in the amount of facial blood circulation, that is, a face RGB change, that reflects brain activity.

The component waveform diagram of each component was analyzed to determine the existence of a correlation between the amplitude of the component waveform of the component and each of the brain deactivation time and the brain activation time. Specifically, an evaluation was made of whether a correlation existed between the amplitude shown in the component waveform diagram of each component and the brain deactivation period/brain activation period. In this test, within the period during which captured face image data was acquired, the period during which no brain function activation exercise was presented to the test subjects, which was equal to a period of 5 minutes from the start of data acquisition until the elapse of 5 minutes and a period of 15 minutes from the time of elapse of 15 minutes after the start of data acquisition until the end of data acquisition, was set as the brain deactivation time, and the period during which the test subjects were presented with a brain function activation exercise, which was equal to a period of 10 minutes from the time of elapse of 5 minutes after the start of data acquisition until the elapse of 10 minutes, was set as the brain activation time. Then, an evaluation was made of the existence of a correlation between the amplitude shown in the component waveform diagram of each component and each of the brain deactivation time and the brain activation time. The determination of the existence of a correlation was performed using statistical correlation analysis. When the significance level (a) was 0.01 or less, it was determined that a correlation existed.

The blood circulation amount distribution diagram of each component was analyzed for the presence of a change in the amount of blood circulation in a predetermined face region. The blood circulation amount distribution diagram is created by arranging a spatial distribution U calculated for each pixel at the position of the pixel. An evaluation was made of whether a change in the amount of blood circulation occurred in the paranasal-sinus surrounding area and the forehead portion on the blood circulation amount distribution diagram of each component created in the way described above. The presence of a change in the amount of blood circulation in the paranasal-sinus surrounding area and the forehead portion on the blood circulation amount distribution diagram was determined by determining the presence of a change in the amount of blood circulation by visual inspection or by ensuring that the value of the amount of blood circulation in the paranasal-sinus surrounding area and the forehead portion illustrated in FIG. 1B is not "0.000".

The determination of the polarity (plus or minus) of blood-circulation-amount data X is based on the relationship among the values of the spatial distribution U, the singular value S, and the temporal distribution V. Accordingly, in some times, the polarity appears to be reversed on the component waveform diagram and blood circulation amount distribution diagram of each component. For this reason, the polarity is assumed to be excluded from the evaluation of the component waveform diagram and the blood circulation amount distribution diagram.

Further, to verify the correlation between the facial skin temperature and the amount of facial blood circulation, during the acquisition of captured face image data from the six test subjects in time series, facial skin temperature data was also acquired in time series by using an infrared thermography device, and the acquired facial skin temperature data was also subjected to the singular value decomposition using SVD of MATLAB (registered trademark) as an analysis tool to create a component waveform diagram of each component corresponding to the singular value S, which was analyzed to determine the existence of a correlation between the amplitude of the component waveform of the component and each of the brain deactivation time and the brain activation time. In this test, a device similar to that in the test described above was used as an infrared thermography device. The infrared camera was placed in front of the test subjects at a distance of 1.5 m from the test subjects.

When captured facial image data is acquired by using an imaging device, in some cases, sunlight or the like may hit the face when an image of the face is being captured, resulting in light being reflected from the face. The reflected light may enter the lens of the imaging device. In this case, the captured face image data has recorded thereon the reflected light. In the RGB data obtained from the captured image data, a change in lightness that is based on the amount of facial blood circulation is less than a change in lightness that is based on the reflected light. Thus, if the amount of blood circulation calculated on the basis of the RGB data obtained from the captured image data having recorded thereon the reflected light is analyzed, the analysis result may be likely to be contaminated with a face RGB change that is not related to brain activity (so-called noise). To prevent the contamination of the face RGB change not related to brain activity, relative blood-circulation-amount data was created from the relative RGB data in which all the average values of RGB data obtained at intervals of 30 seconds were set to "0". The created blood-circulation-amount data was also subjected to the singular value decomposition using SVD of MATLAB (registered trademark) as an analysis tool to create a component waveform diagram and blood circulation amount distribution diagram of each component corresponding to the singular value S, which were analyzed to identify a component indicating a face RGB change reflecting brain activity.

In the following, for convenience of description, relative blood-circulation-amount data based on relative RGB data in which all the average values of RGB data obtained at intervals of a predetermined time (in this test, at intervals of 30 seconds) are set to "0" is referred to as "relative conversion blood-circulation-amount data", and blood-circulation-amount data based on RGB data obtained before conversion to the relative RGB data is referred to simply as "blood-circulation-amount data".

During the acquisition of time-series captured face image data of the six test subjects by using an imaging device, each of the six test subjects was also subjected to measurement of brain waves by connecting electrodes on the scalp of the test subject to also evaluate the correlation between the amplitude of the β wave (a brain wave in a frequency range of 13 to 30 Hz), which is known as a waveform that appears when the brain cells are active, such as when the test subject is awake, and the amplitude shown in the component waveform diagram. In the measurement of the brain waves, the electrodes were placed at 19 locations (Fp1, Fp2, F3, F4, C3, C4, P3, P4, O1, O2, F7, F8, T3, T4, T5, T6, Fz, Cz, and Pz) on the scalp on the basis of the International 10-20 system.

While each test subject is presented with a brain function activation exercise, the head of the test subject may be moved upward and downward. This movement causes a change in the position of the face of the test subject relative to the imaging device. To verify whether the change in the position of the face affects a face RGB change, a contrast test was performed on one test subject. In the contrast test, as in the test described above, time-series captured face image data of the test subject was acquired by using an imaging device. The test subject was also required to press the keyboard buttons at random timing while no brain function activation exercise was presented (i.e., the brain deactivation time). The time-series blood-circulation-amount data based on the RGB data obtained from the time-series captured face image data captured in the contrast experiment was also subjected to the singular value decomposition using SVD of MATLAB (registered trademark) as an analysis tool to create a component waveform diagram of each component corresponding to the singular value S, which was analyzed to determine the existence of a correlation between the amplitude of the component waveform of the component and each of the brain deactivation time and the brain activation time. Further, analysis was made of the existence of a correlation between the amplitude of the component waveform of each component and actual movement of the face. The actual movement of the face was evaluated by acquiring two-dimensional coordinates of the same location on the face from the captured image data and calculating the movement distance of the face at intervals of 30 seconds during the image capturing operation with respect to the captured image data obtained when the contrast experiment was started. Further, analysis was also made of the existence of a correlation between the amplitude of the component waveform of each component and the number of keyboard inputs during the image capturing operation. The number of keyboard inputs during the image capturing operation was evaluated by calculating a simple moving average at intervals of 30 seconds in the time-series captured image data.

(3) Analysis Results (3-1) Analysis Results of Facial Skin Temperature Data

Figure 2A:
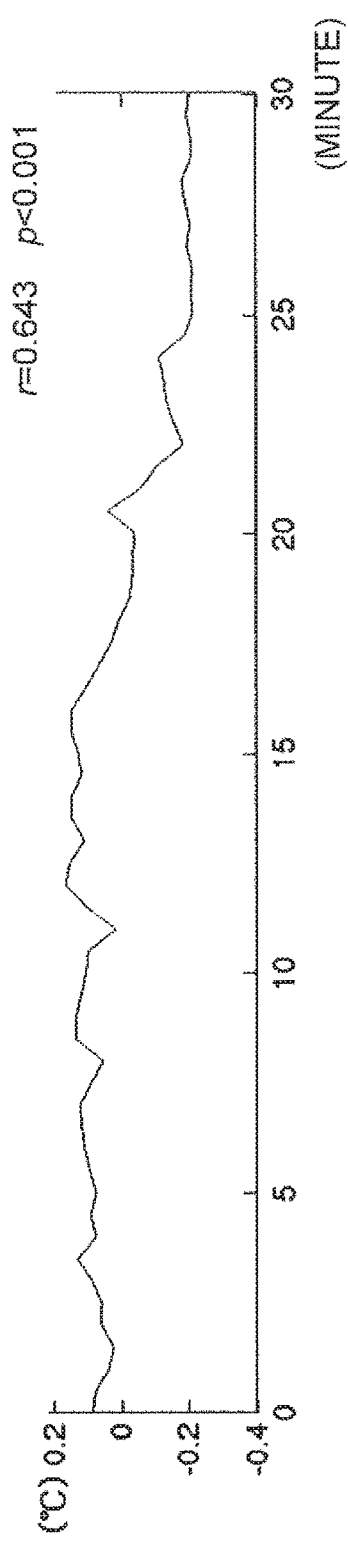
FIGS. 2A and 2B are diagrams illustrating part of the result of analyzing facial skin temperature data.
Figure 2B:
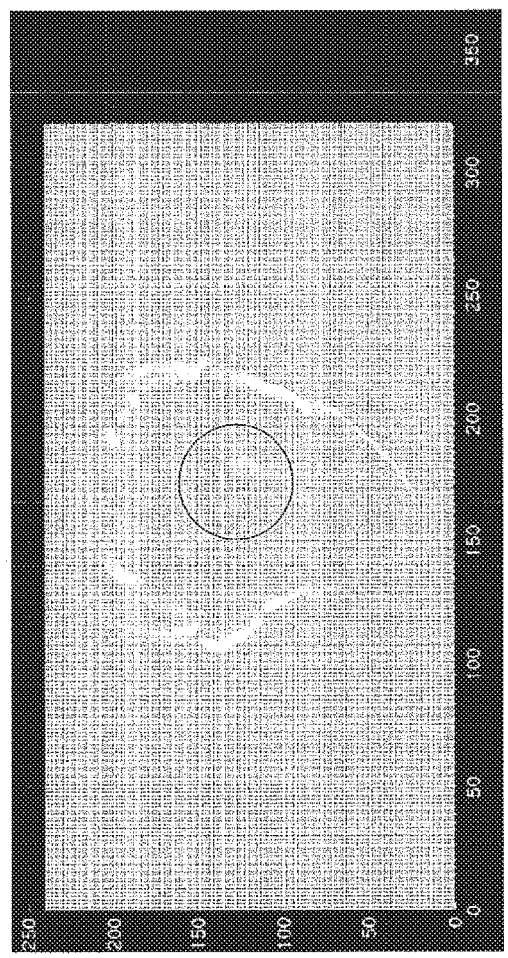
Figure 3A:
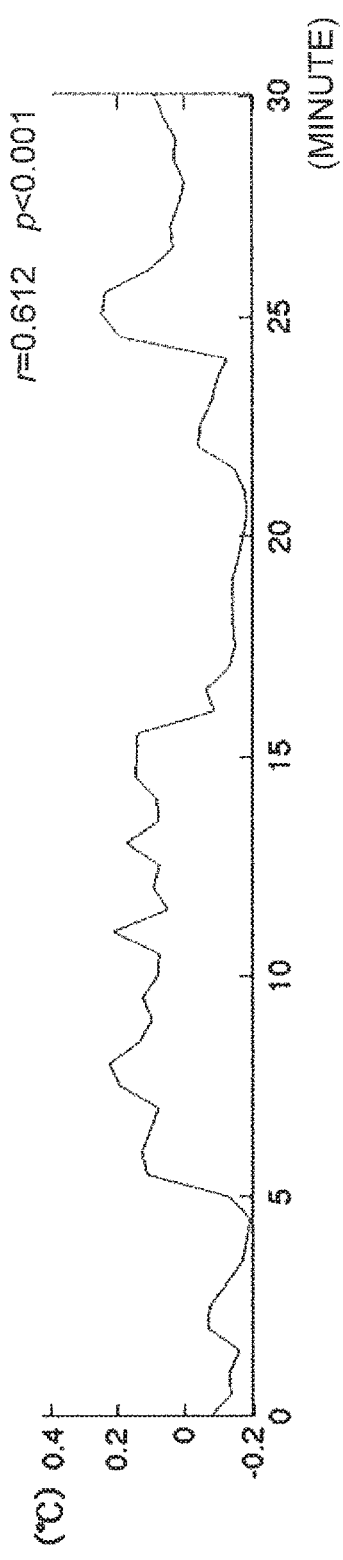
FIGS. 3A and 3B are illustrating part of the result of analyzing the facial skin temperature data.
Figure 3B:
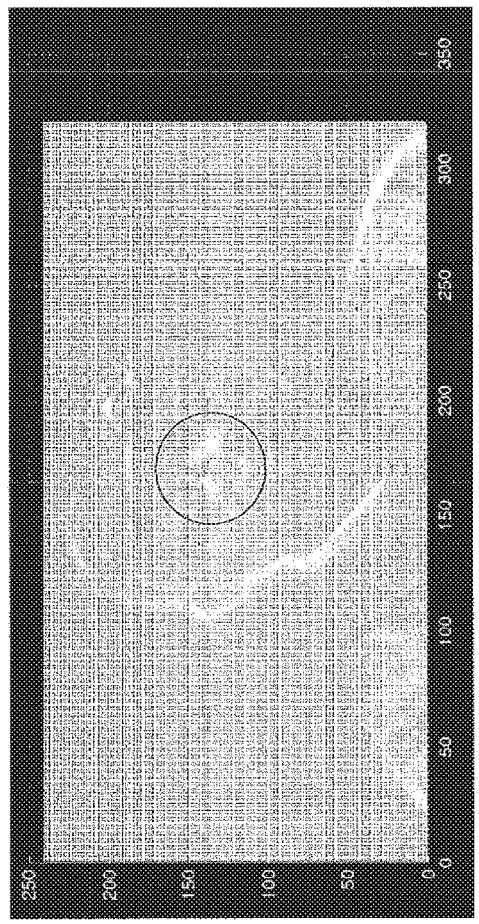
Figure 4:
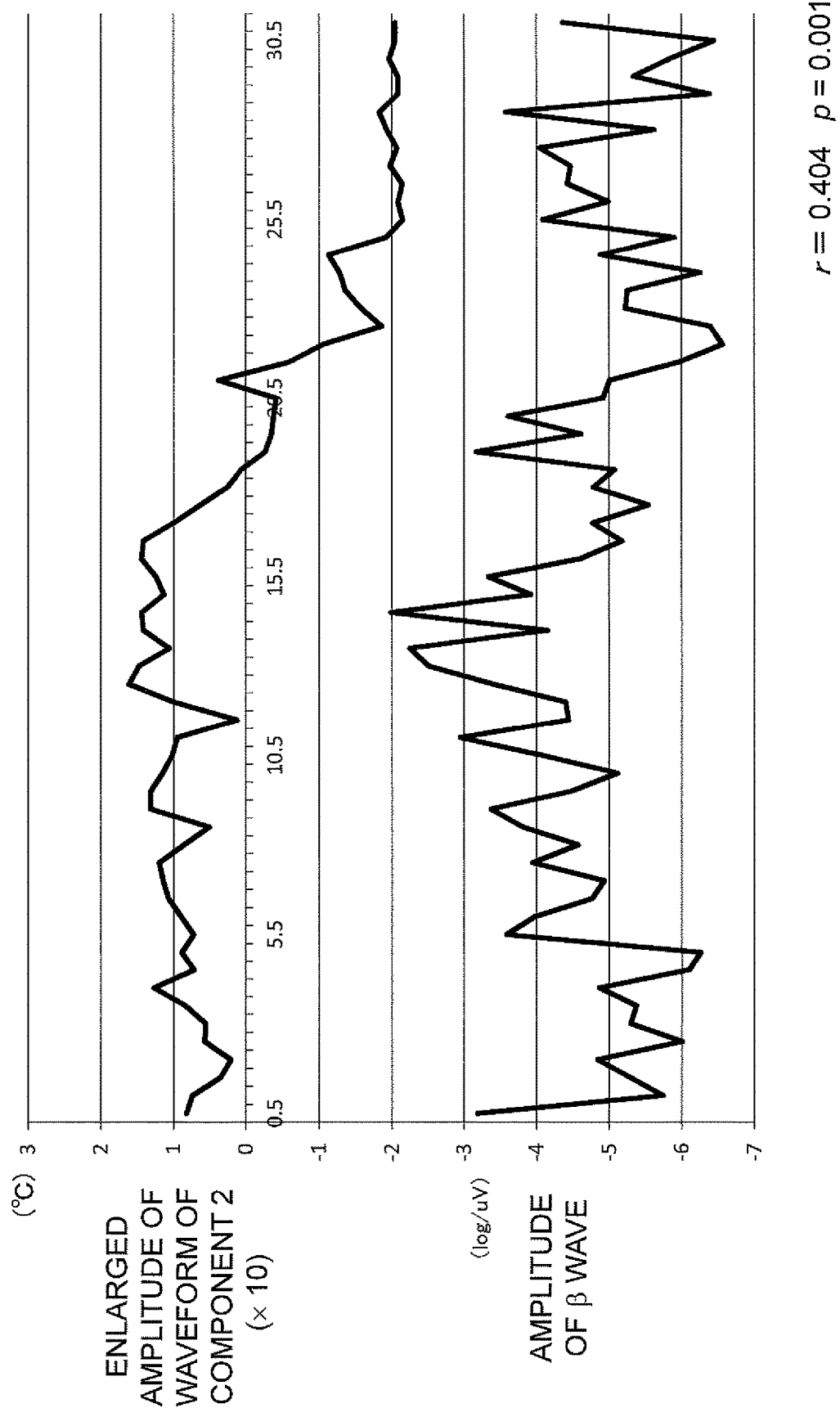
FIG. 4 includes diagrams illustrating the amplitude of a component waveform of component 2 and the amplitude of the β wave among measured brain waves.
Figure 5:
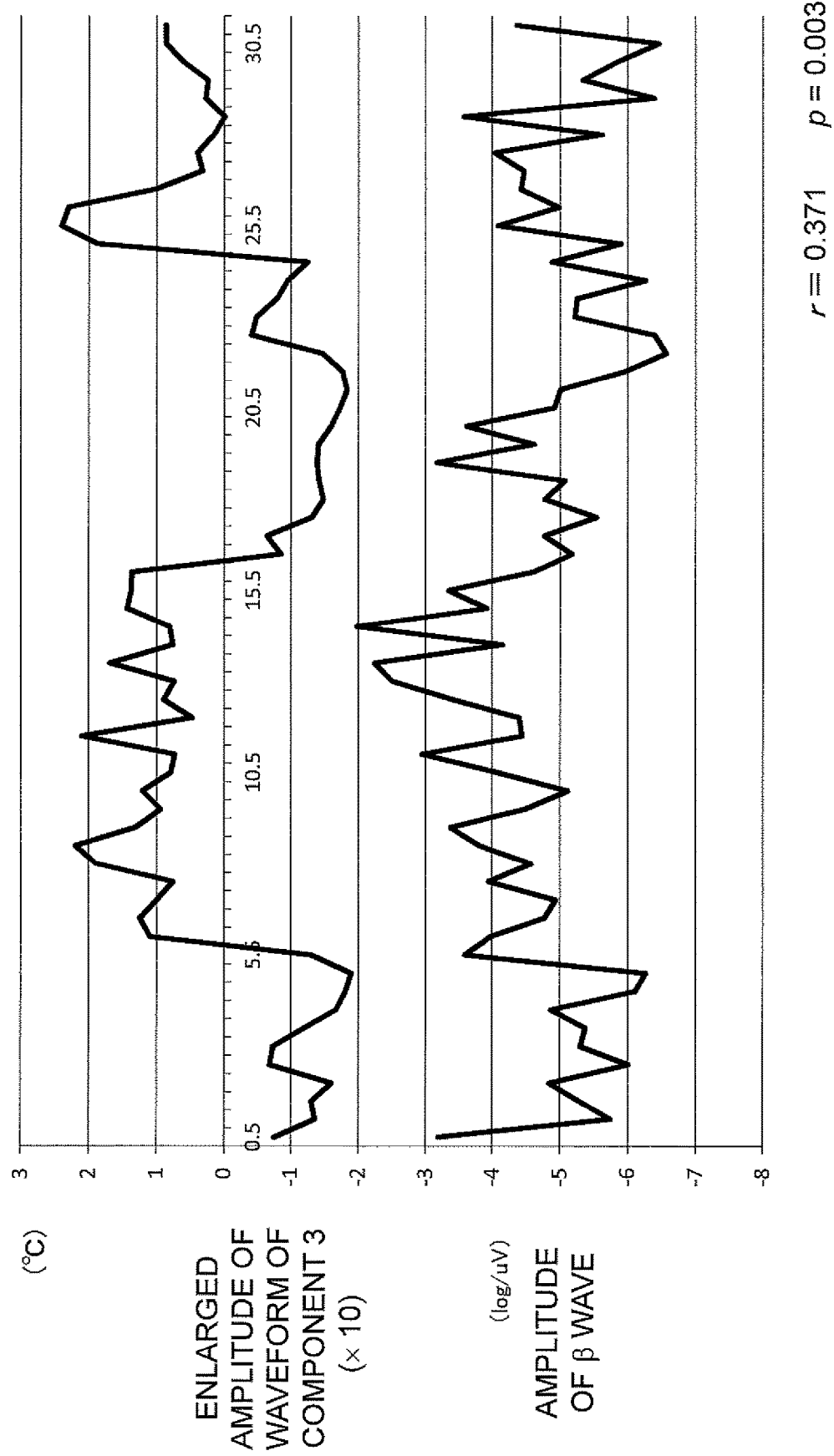
FIG. 5 includes diagrams illustrating the amplitude of a component waveform of component 3 and the amplitude of the β wave among measured brain waves.
Figure 6A:
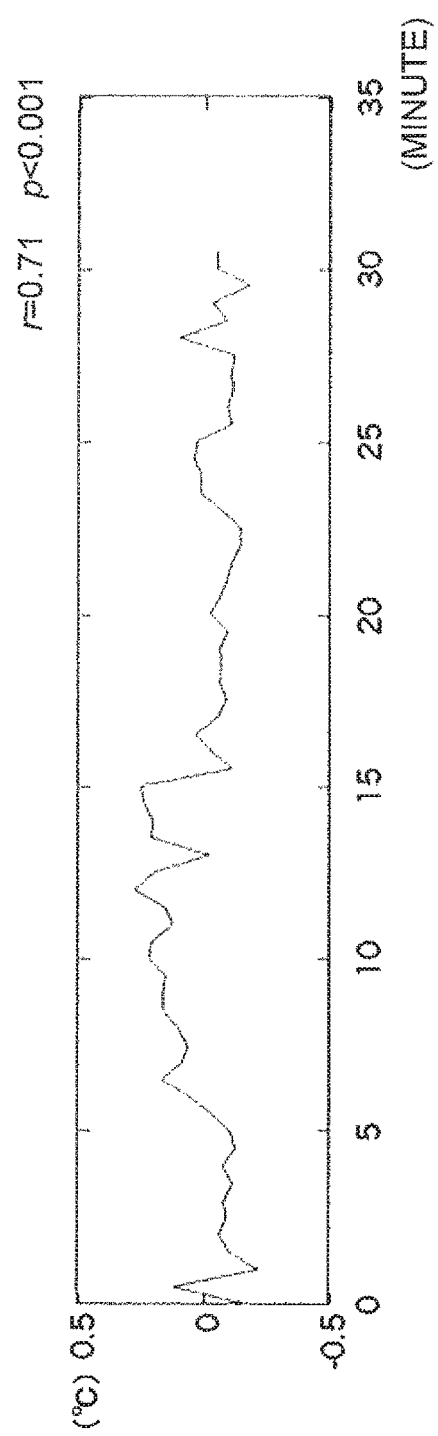
FIGS. 6A and 6B are diagrams illustrating part of the result of analyzing facial skin temperature data obtained by a contrast experiment.
Figure 6B:
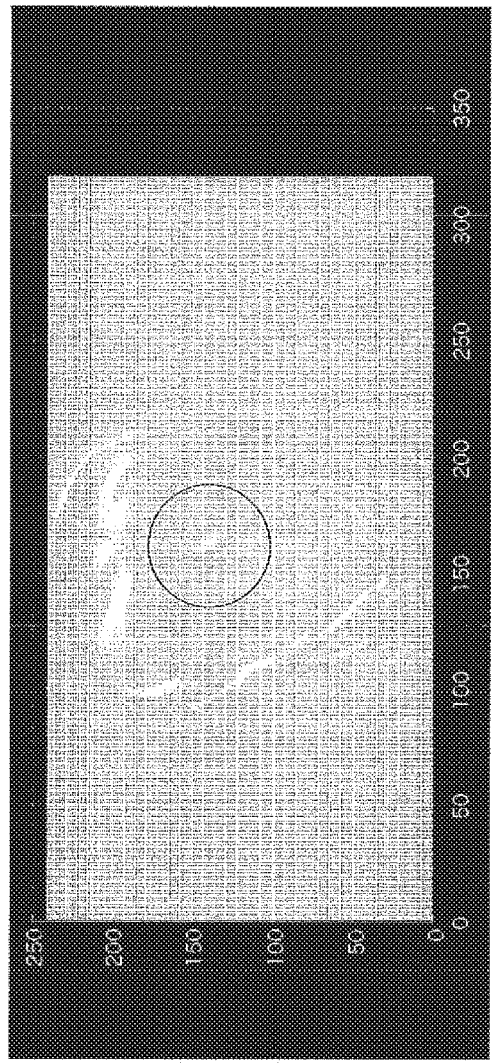

FIG. 2 diagrams illustrating part of the result of analyzing facial skin temperature data corresponding to temperature conversion data. FIG. 2A illustrates a component waveform diagram of component 2 for test subject 1. FIG. 2B illustrates a temperature distribution diagram of the component 2 for the test subject 1. FIG. 3A illustrates a component waveform diagram of component 3 for the test subject 1. FIG. 3B illustrates a temperature distribution diagram of the component 3 for the test subject 1. FIG. 4 and FIG. 5 are diagrams illustrating relationships between the amplitudes of component waveforms and brain waves. FIG. 4 diagrams illustrating the amplitude of the component waveform of the component 2 for the test subject 1 and the amplitude of the β wave among measured brain waves. FIG. 5 diagrams illustrating the amplitude of the component waveform of the component 3 for the test subject 1 and the amplitude of the β wave among measured brain waves. FIG. 6 diagrams illustrating part of the result of analyzing facial skin temperature data obtained by a contrast experiment. FIG. 6A illustrates a component waveform diagram of the component 3. FIG. 6B illustrates a temperature distribution diagram of the component 3.

Table 1 shows analysis results of facial skin temperature data of the test subjects.

The results obtained by the analysis of the facial skin temperature data described above indicate that a significant correlation exists between human brain activity and the component 2 and/or the component 3 among the plurality of components obtained by decomposing the time-series facial skin temperature data by using the singular value decomposition.

TABLE 1

| Test Subject | Correlation in Data Based on Absolute Temperature Conversion Data | | Correlation in Data Based on Relative Temperature Conversion Data | |
|---|---|---|---|---|
| | Component waveform | Temperature distribution | Component waveform | Temperature distribution |
| Test Subject 1 | Component 2, Component 3 | Component 2, Component 3 | Component 2, Component 3 | Component 2, Component 3 |
| Test Subject 2 | Component 3 | Component 3 | Component 3 | Component 3 |
| Test Subject 3 | Component 1, Component 2, Component 3 | Component 2, Component 3 | Component 2, Component 3 | Component 2, Component 3 |
| Test Subject 4 | Component 2, Component 3 | Component 2, Component 3 | Component 2, Component 3 | Component 2, Component 3 |
| Test Subject 5 | Component 2, Component 3 | Component 2, Component 3 | Component 2, Component 3 | Component 2, Component 3 |
| Test Subject 6 | Component 2, Component 5 | Component 2, Component 5 | Component 2, Component 5 | Component 2, Component 5 |

As illustrated in FIG. 4 and FIG. 5, the results of brain wave analysis indicate that a significant correlation exists between the amplitudes of the component waveforms of the component 2 and the component 3 and the amplitude of the β wave of brain waves.

In the contrast experiment, furthermore, even if the test subject moves during the acquisition of the facial skin temperature data, a significant correlation existed between the component 3 and human brain activity (see FIG. 6). This indicates that, among the plurality of components, the component 3 is not affected by the movement of the test subject during the acquisition of the facial skin temperature data.

From these results, the inventors have obtained the following findings.

As a result of decomposing the time-series facial skin temperature data acquired from the test subject into a plurality of components by using the singular value decomposition and analyzing the components obtained through decomposition, the component 3 among the plurality of components was found to be a component related to brain activity. That is, the time-series facial skin temperature data is decomposed into a plurality of components by using the singular value decomposition, a component having a correlation with the activation/deactivation of the brain is extracted from the plurality of components obtained through decomposition, and the extracted component is analyzed by utilizing the selective brain cooling system. Accordingly, it has turned out that a component indicating a skin temperature change reflecting brain activity can be identified from the plurality of components. From this, the inventors have obtained findings that brain activity can be estimated on the basis of the facial skin temperature of a person.

(3-2) Analysis Results of Captured Face Image Data

Figure 7:
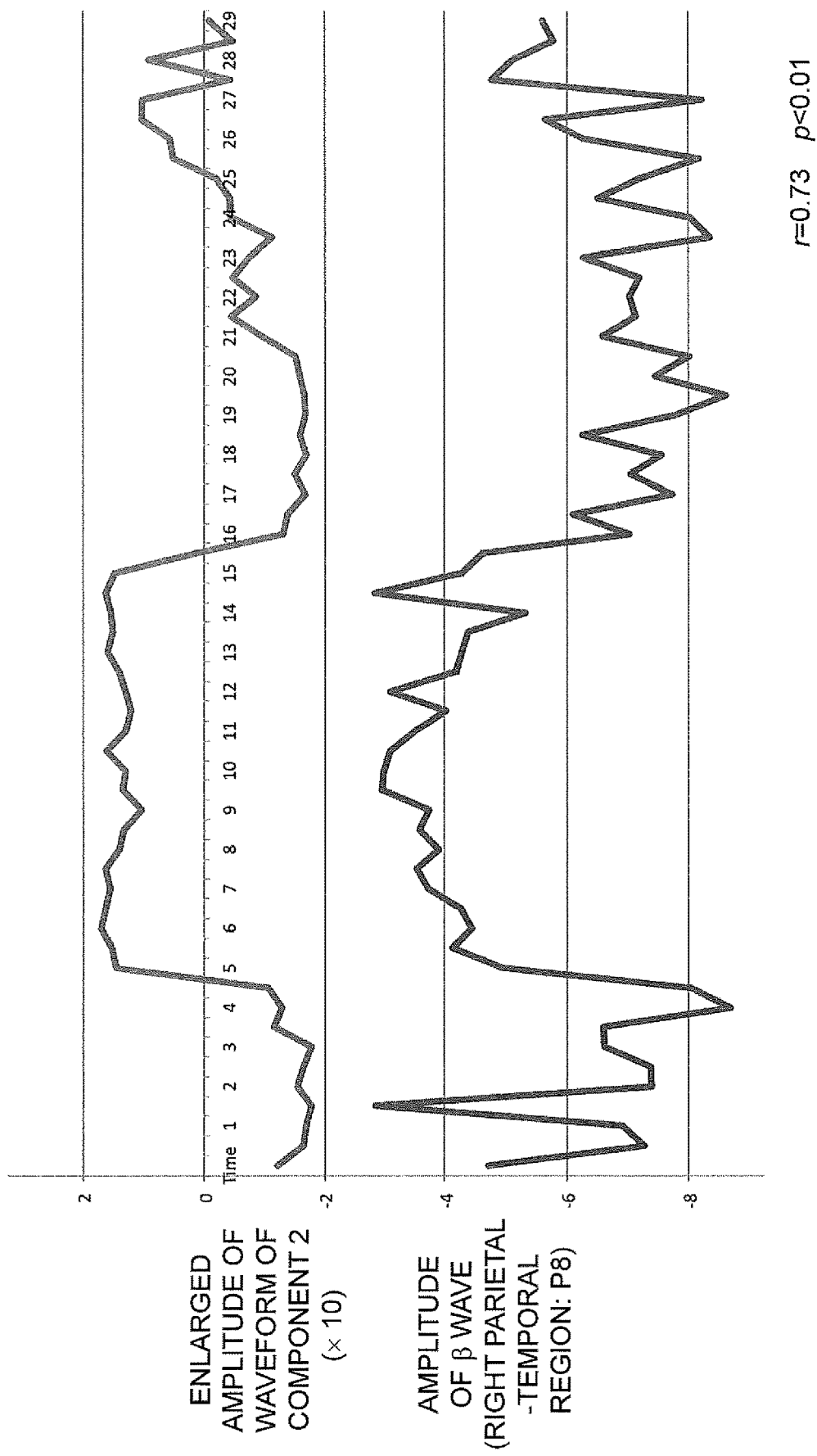
FIG. 7 is a diagram illustrating a component waveform based on captured image data of a face and the amplitude of the β wave among measured brain waves.
Figure 8:
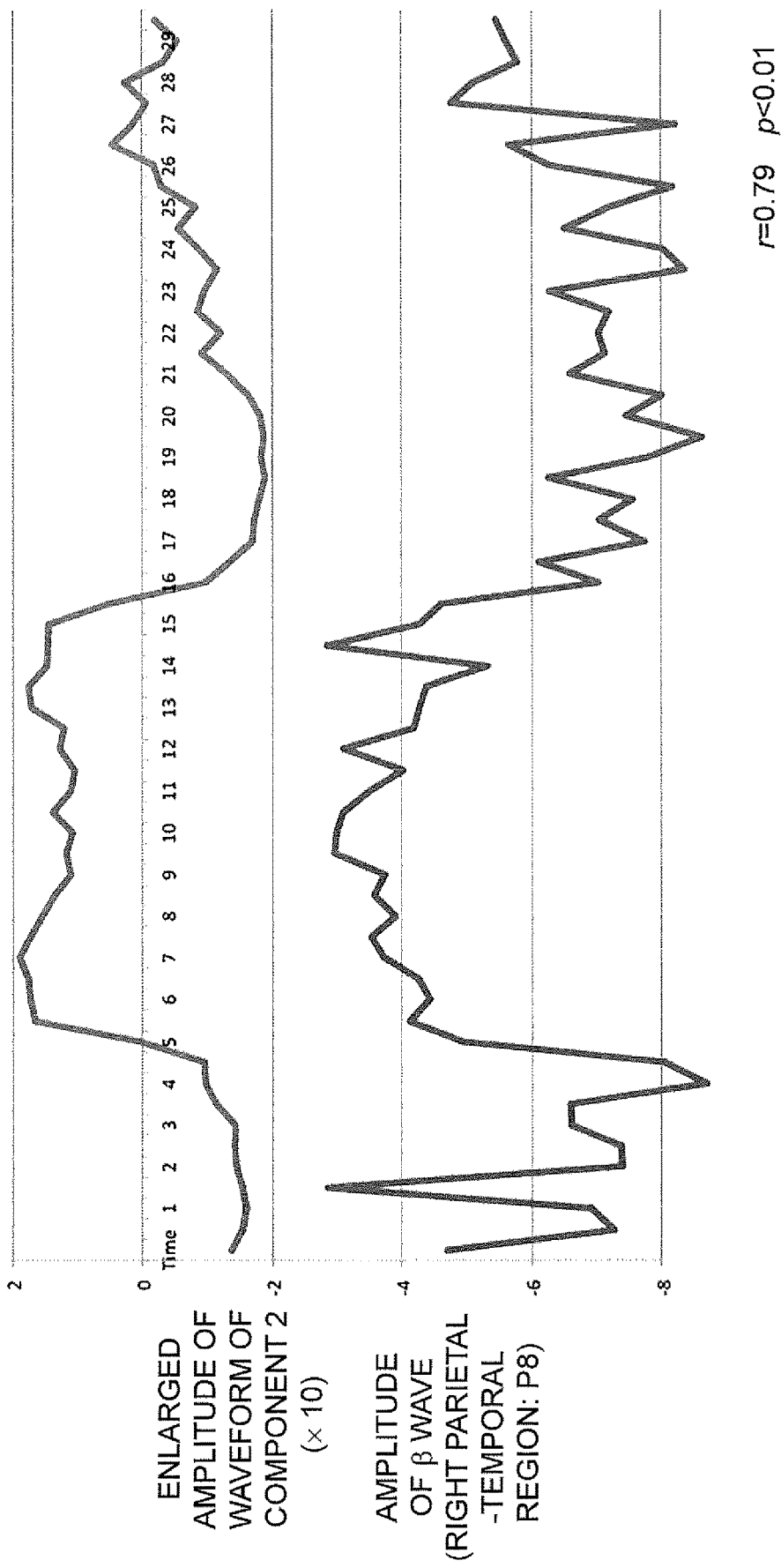
FIG. 8 is a diagram illustrating a component waveform based on facial skin temperature data and the amplitude of the β wave among measured brain waves.
Figure 9:
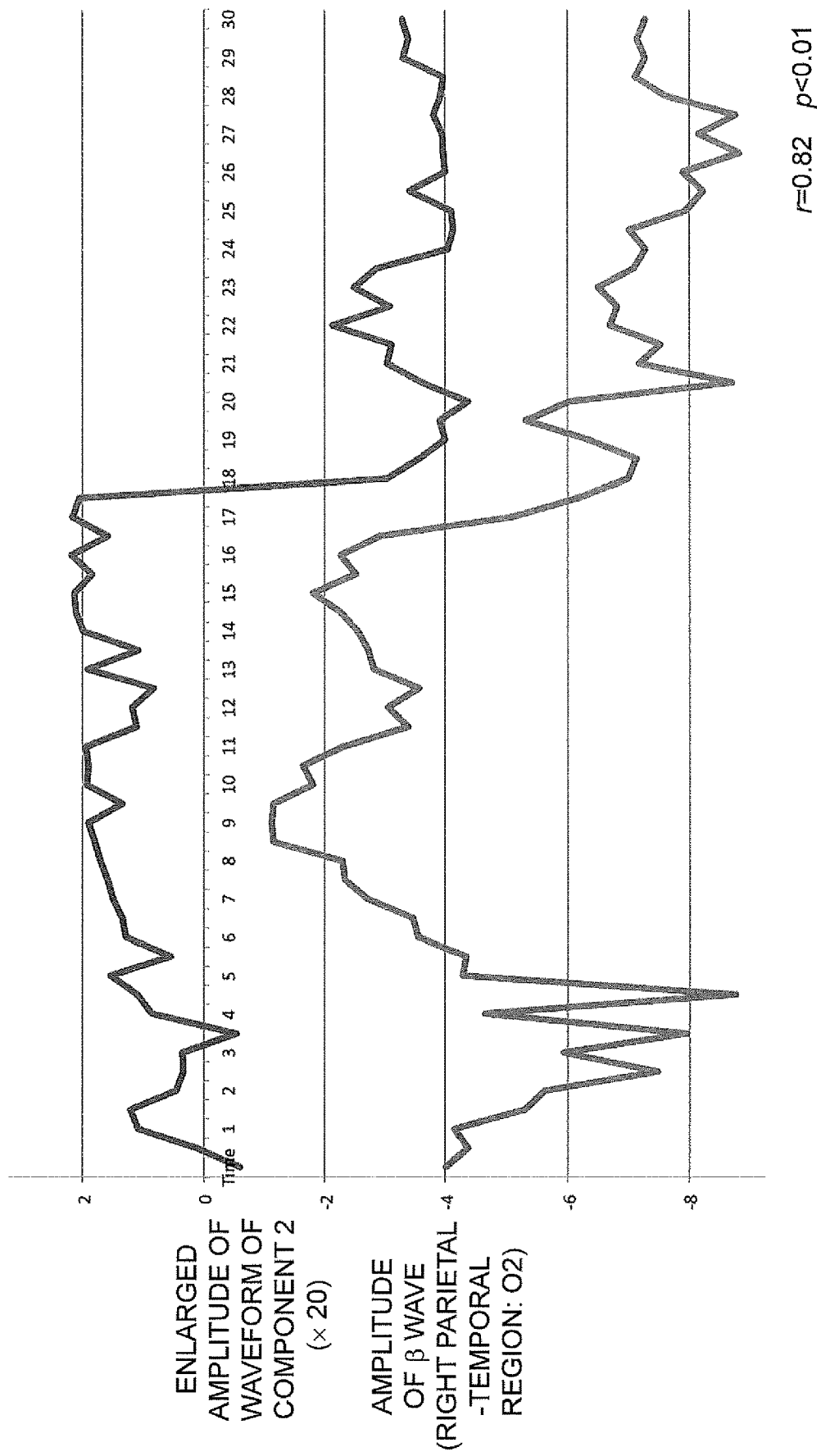
FIG. 9 is a diagram illustrating a component waveform based on captured image data of a face and the amplitude of the β wave among measured brain waves.
Figure 10:
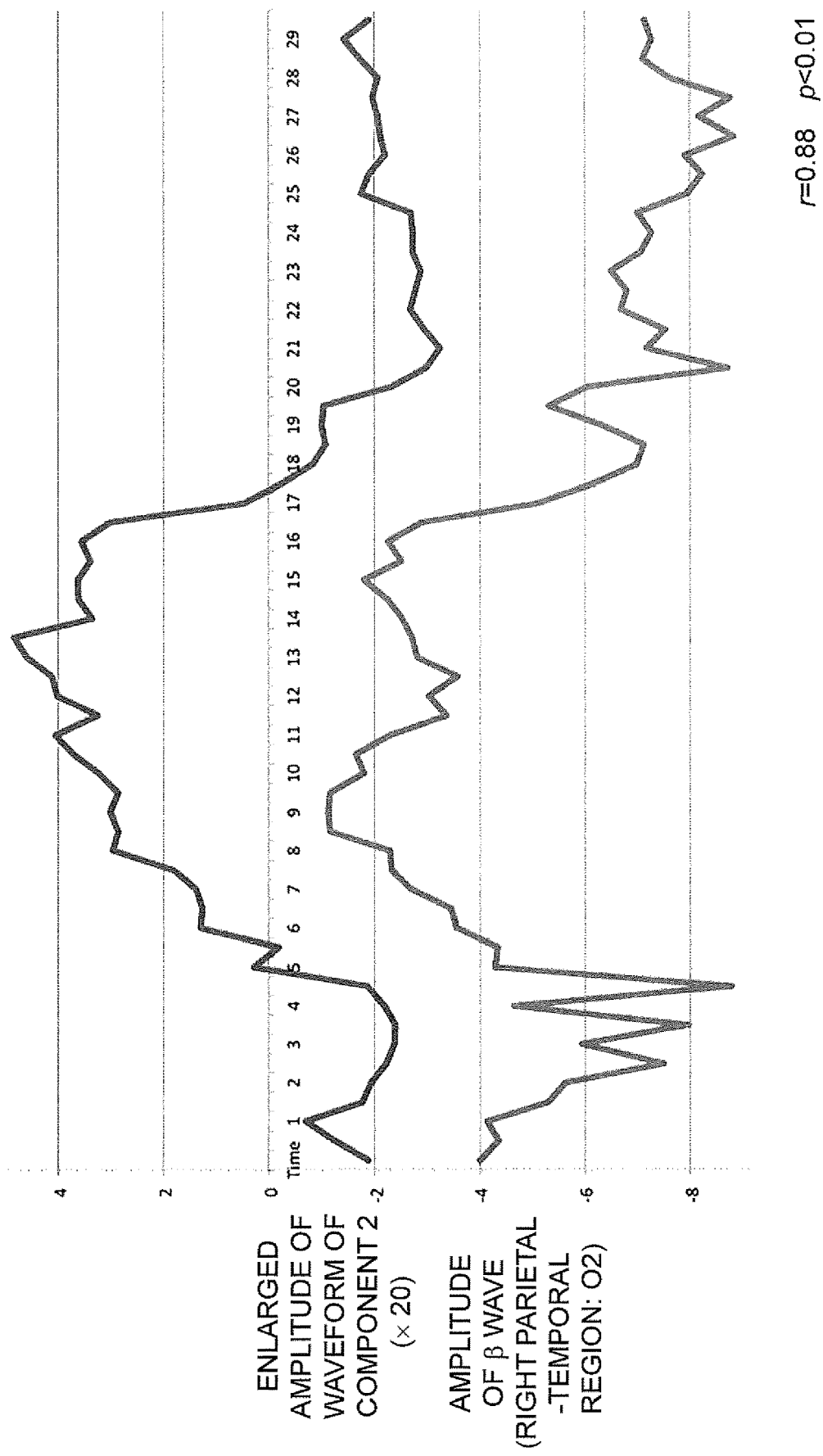
FIG. 10 is a diagram illustrating a component waveform based on facial skin temperature data and the amplitude of the β wave among measured brain waves.
Figure 11:
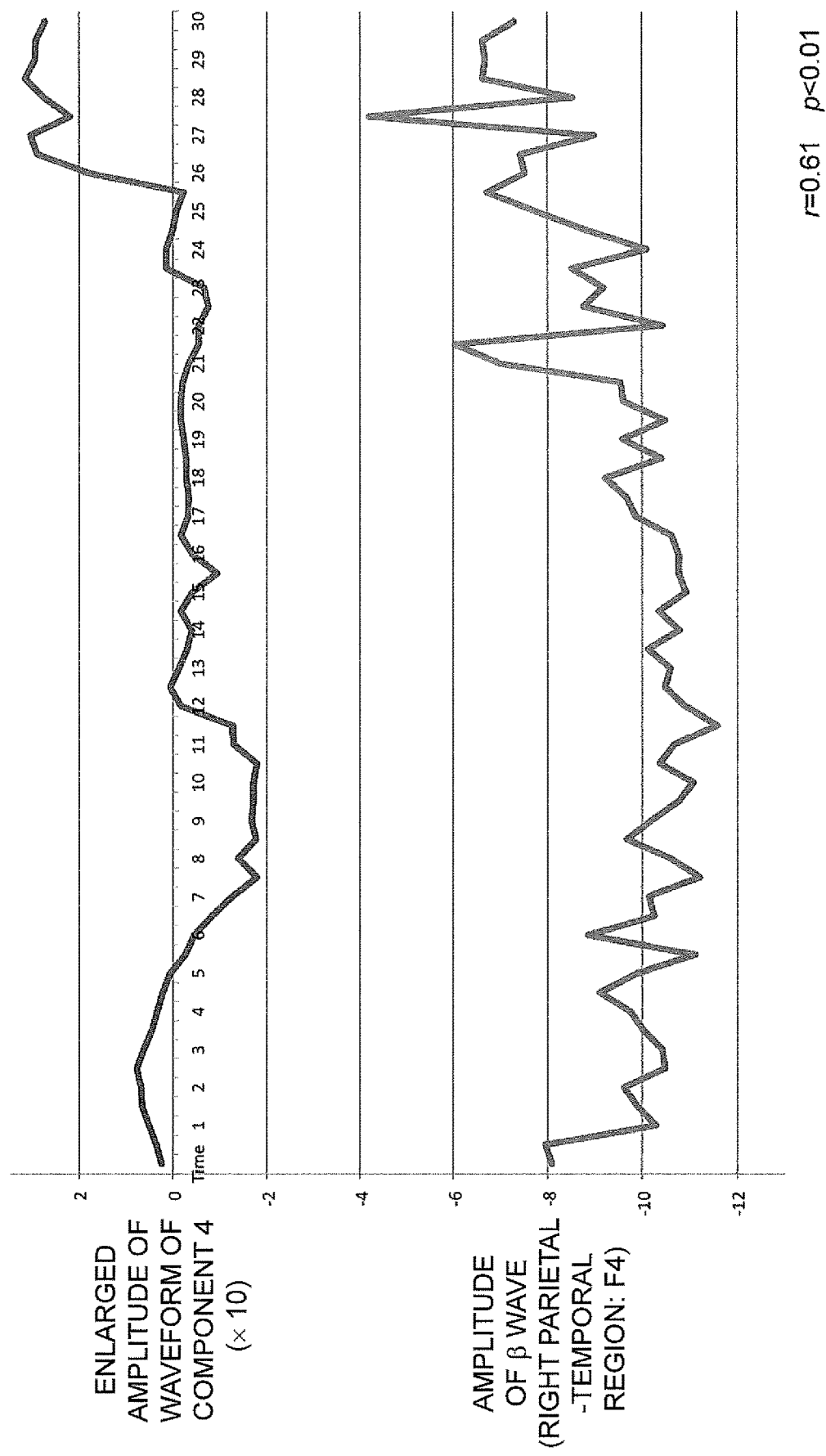
FIG. 11 is a diagram illustrating a component waveform based on captured image data of a face and the amplitude of the β wave among measured brain waves.
Figure 12:
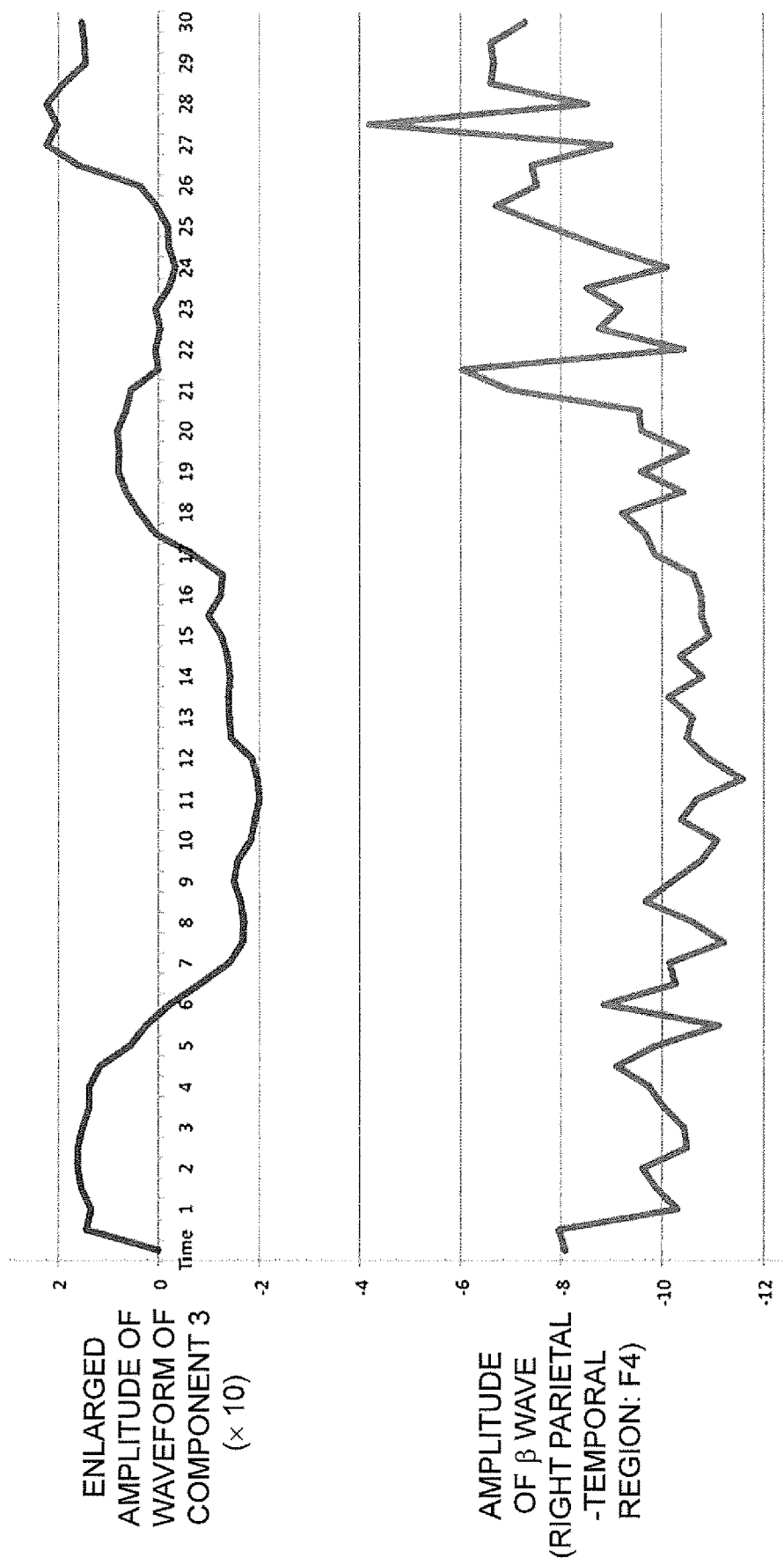
FIG. 12 is a diagram illustrating a component waveform based on facial skin temperature data and the amplitude of the β wave among measured brain waves.
Figure 13:
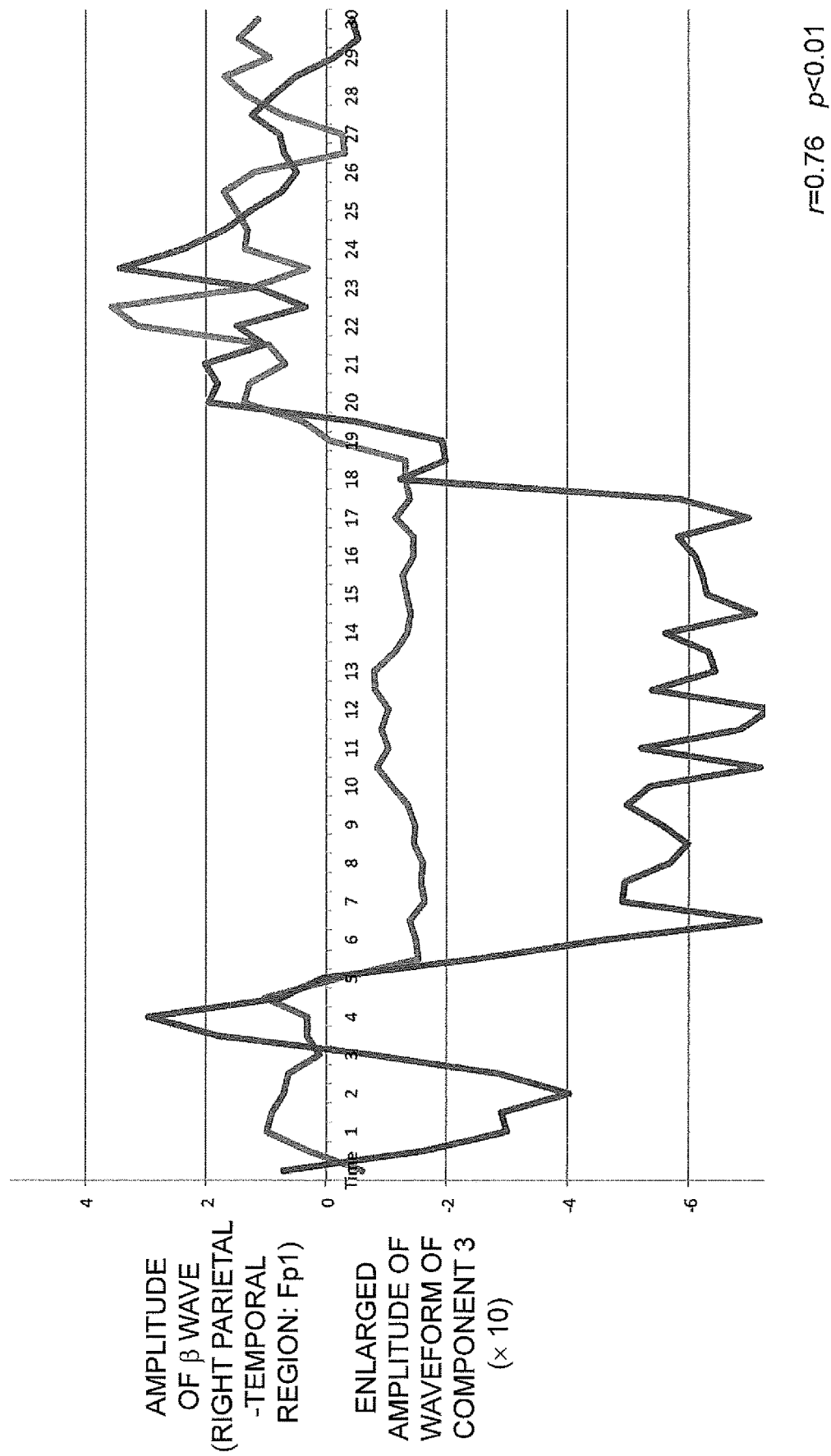
FIG. 13 is a diagram illustrating a component waveform based on captured image data of a face and the amplitude of the β wave among measured brain waves.
Figure 14:
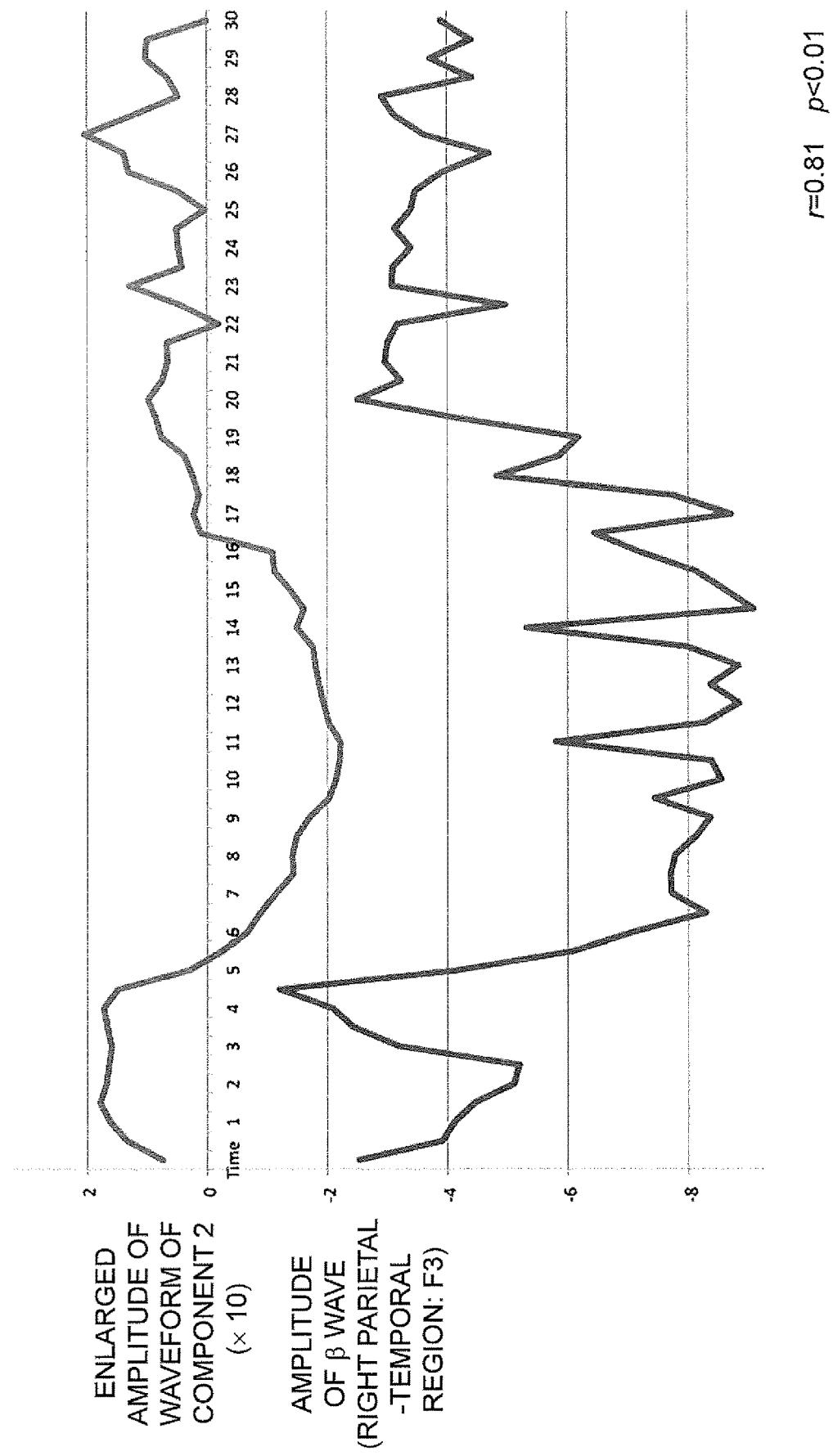
FIG. 14 is a diagram illustrating a component waveform based on facial skin temperature data and the amplitude of the β wave among measured brain waves.
Figure 15:
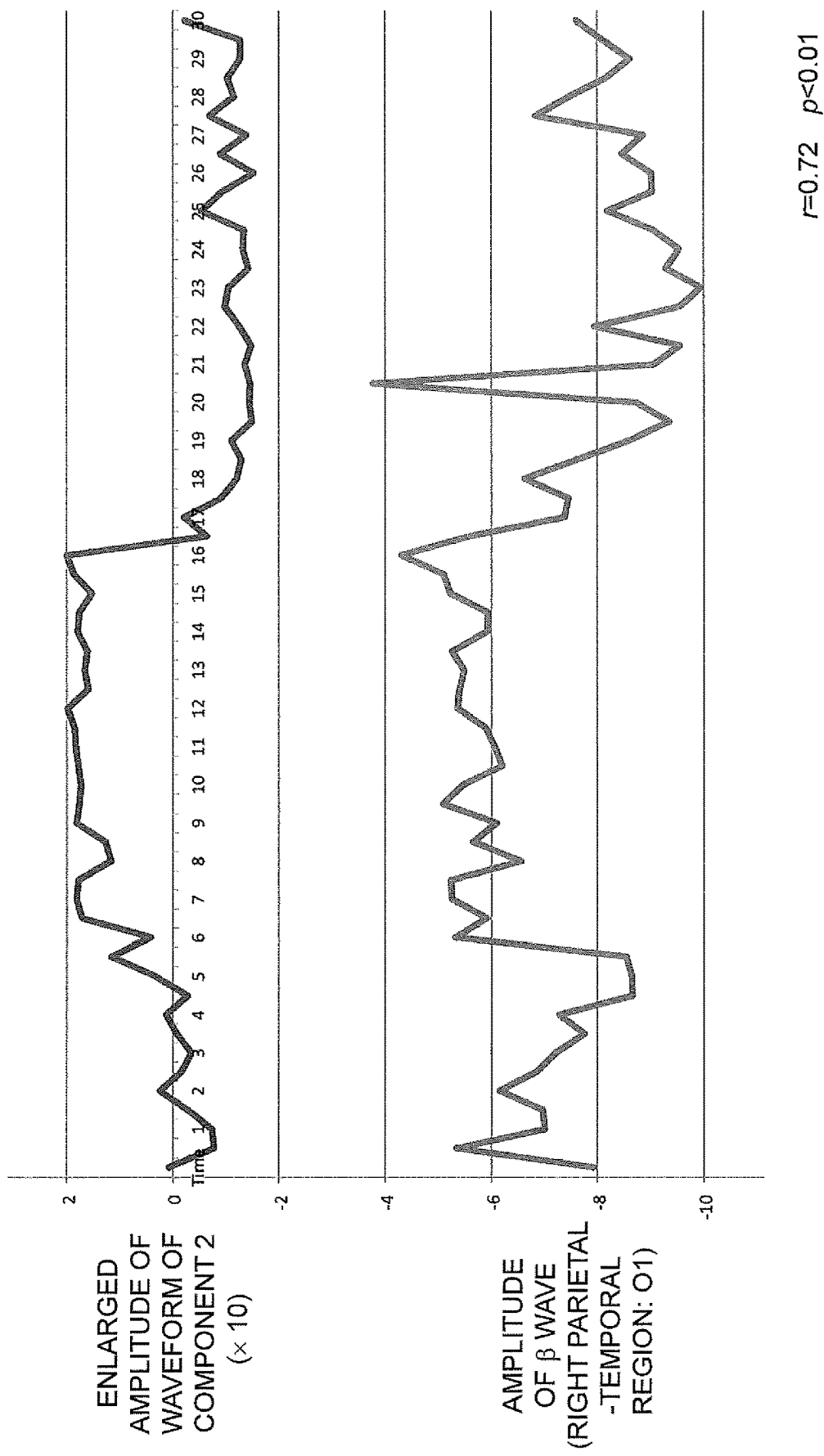
FIG. 15 is a diagram illustrating a component waveform based on captured image data of a face and the amplitude of the β wave among measured brain waves.
Figure 16:
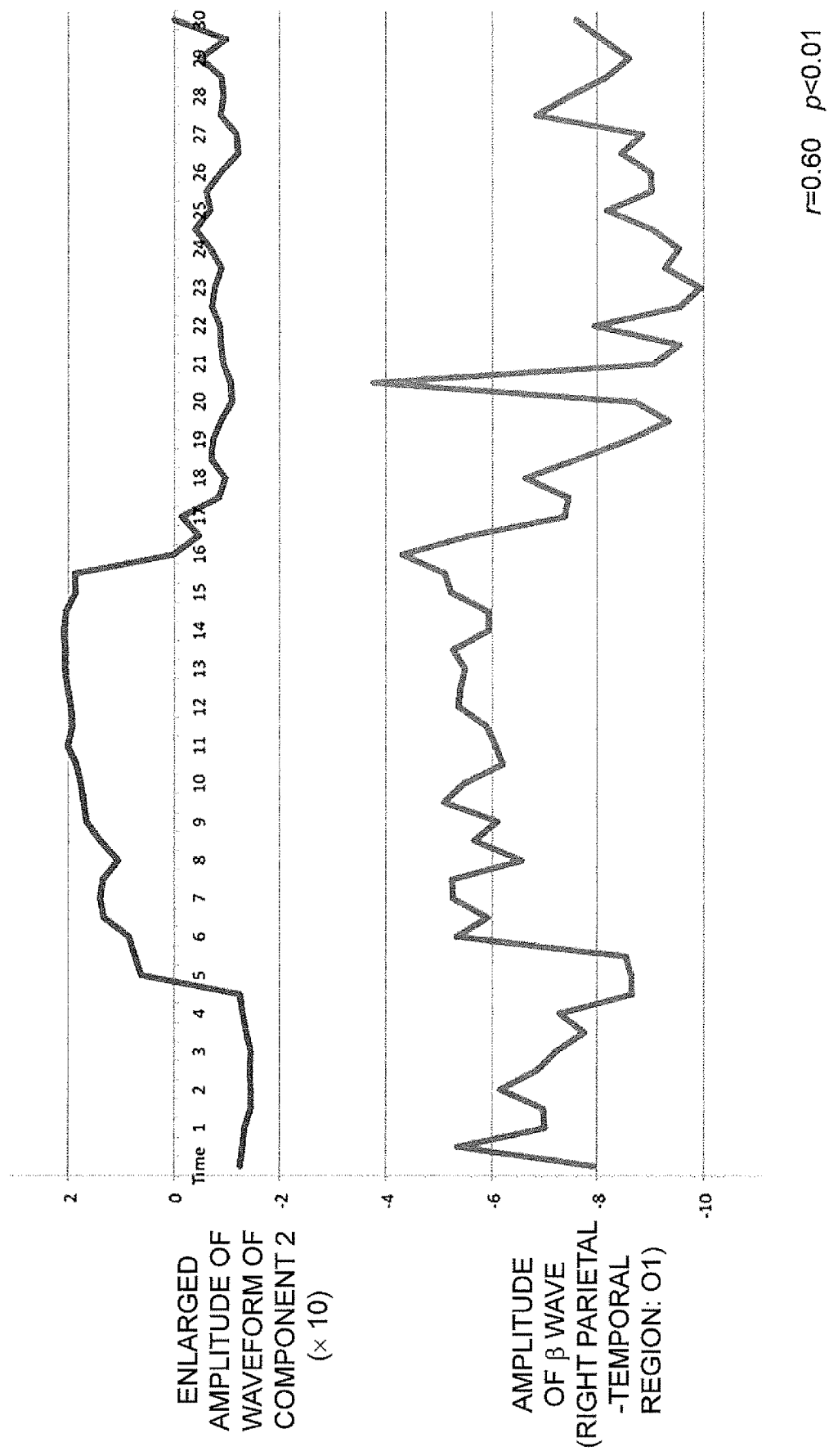
FIG. 16 is a diagram illustrating a component waveform based on facial skin temperature data and the amplitude of the β wave among measured brain waves.
Figure 17:
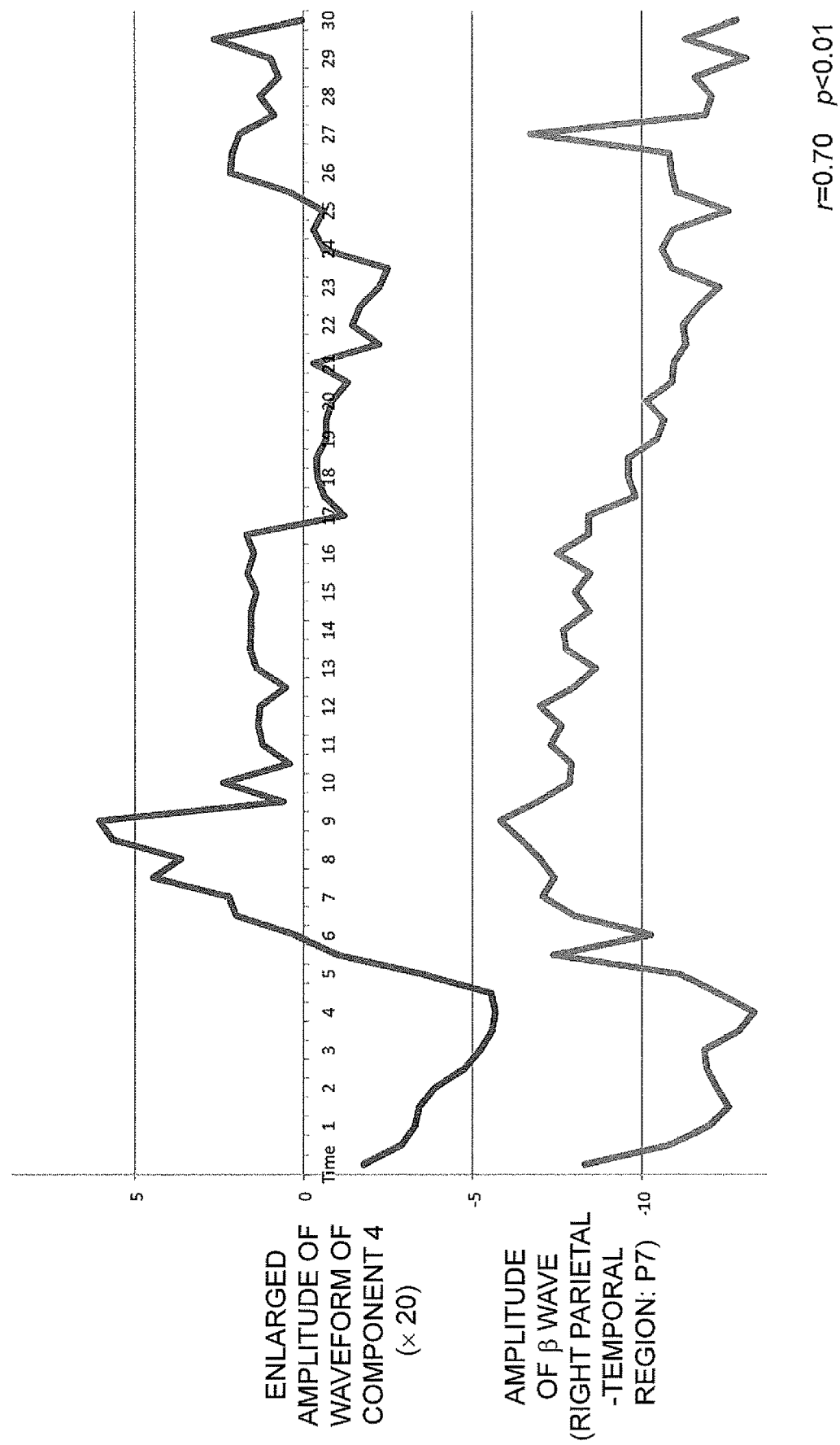
FIG. 17 is a diagram illustrating a component waveform based on captured image data of a face and the amplitude of the β wave among measured brain waves.
Figure 18:
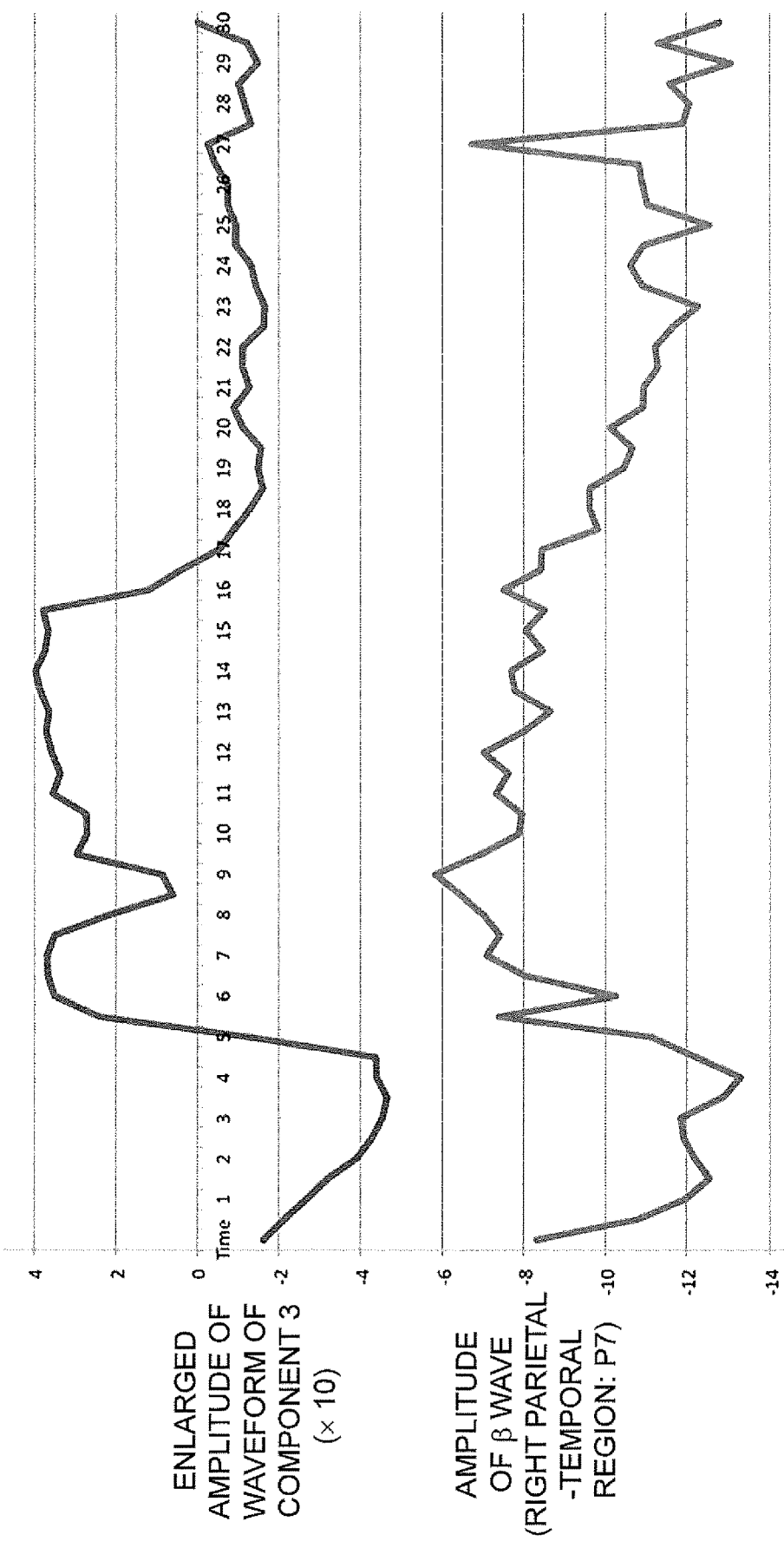
FIG. 18 is a diagram illustrating a component waveform based on facial skin temperature data and the amplitude of the β wave among measured brain waves.

FIGS. 7 to 18 are diagrams illustrating part of the result of comparing and analyzing component waveform diagrams based on captured face image data (blood-circulation-amount data) or facial skin temperature data and waveform diagrams of the β wave among measured brain waves. FIG. 7 is a diagram illustrating the amplitude of the component waveform of the component 2 based on the captured image data of the test subject 1, and the amplitude of the β wave among the measured brain waves of the test subject 1. FIG. 8 is a diagram illustrating the amplitude of the component waveform of the component 2 based on the facial skin temperature data of the test subject 1, and the amplitude of the β wave among the measured brain waves of the test subject 1. FIG. 9 is a diagram illustrating the amplitude of the component waveform of the component 2 based on the captured image data of the test subject 2, and the amplitude of the β wave among the measured brain waves of the test subject 2. FIG. 10 is a diagram illustrating the amplitude of the component waveform of the component 2 based on the facial skin temperature data of the test subject 2, and the amplitude of the β wave among the measured brain waves of the test subject 2. FIG. 11 is a diagram illustrating the amplitude of the component waveform of component 4 based on the captured image data of the test subject 3, and the amplitude of the β wave among the measured brain waves of the test subject 3. FIG. 12 is a diagram illustrating the amplitude of the component waveform of the component 3 based on the facial skin temperature data of the test subject 3, and the amplitude of the β wave among the measured brain waves of the test subject 3. FIG. 13 is a diagram illustrating the amplitude of the component waveform of the component 3 based on the captured image data of the test subject 4, and the amplitude of the β wave among the measured brain waves of the test subject 4. FIG. 14 is a diagram illustrating the amplitude of the component waveform of the component 2 based on the facial skin temperature data of the test subject 4, and the amplitude of the β wave among the measured brain waves of the test subject 4. FIG. 15 is a diagram illustrating the amplitude of the component waveform of the component 2 based on the captured image data of the test subject 5, and the amplitude of the β wave among the measured brain waves of the test subject 5. FIG. 16 is a diagram illustrating the amplitude of the component waveform of the component 2 based on the facial skin temperature data of the test subject 5, and the amplitude of the β wave among the measured brain waves of the test subject 5. FIG. 17 is a diagram illustrating the amplitude of the component waveform of the component 4 based on the captured image data of the test subject 6, and the amplitude of the β wave among the measured brain waves of the test subject 6. FIG. 18 is a diagram illustrating the amplitude of the component waveform of the component 3 based on the facial skin temperature data of the test subject 6, and the amplitude of the β wave among the measured brain waves of the test subject 6.

As illustrated in FIGS. 7 to 18, the results of the component waveforms and brain wave analysis indicate correlation between the facial skin temperature and the amount of facial blood circulation. Also in the analysis based on both the facial skin temperature data and the facial blood-circulation-amount data, a significant correlation was found between the amplitude of each of the component waveforms and the amplitude of the β wave of the brain waves measured using electrodes attached to the parietal or occipital region.

Table 2 below shows analysis results of captured face image data of the test subjects.

TABLE 2

| Test Subject | Correlation in Blood-Circulation-Amount Data | | Correlation in Relative Conversion Blood-Circulation-Amount Data | |
|---|---|---|---|---|
| | Component waveform | Blood circulation amount distribution | Component waveform | Blood circulation amount distribution |
| Test Subject 1 | Component 2 | 0.72 | Component 1 | 0.59 |
| | | | Component 2 | 0.85 |
| Test Subject 2 | Component 1 | 0.82 | Component 1 | 0.62 |
| | Component 2 | 0.82 | Component 2 | 0.60 |
| Test Subject 3 | Component 2 | 0.33 | Component 2 | 0.45 |
| | Component 3 | 0.31 | Component 3 | 0.56 |
| | | | Component 4 | 0.56 |
| Test Subject 4 | Component 1 | 0.57 | Component 1 | 0.66 |
| | Component 3 | 0.71 | Component 3 | 0.65 |
| Test Subject 5 | Component 1 | 0.56 | Component 1 | 0.51 |
| | Component 2 | 0.72 | Component 2 | 0.83 |
| Test Subject 6 | Component 2 | 0.38 | Component 2 | 0.45 |
| | Component 4 | 0.68 | Component 3 | 0.51 |
| | | | Component 5 | 0.36 |

As shown in Table 2, the results obtained by the analysis of the captured face image data described above indicate significant correlation between human brain activity and the components 1, 2, 3, 4, and 5 among the plurality of components obtained by decomposing time-series blood-circulation-amount data based on the captured face image data by using the singular value decomposition. Here, not only a component found to have a significant correlation with human brain activity for both the correlation based on the blood-circulation-amount data and the correlation based on the relative conversion blood-circulation-amount data, but also a component found to have no significant correlation with human brain activity for the correlation based on the blood-circulation-amount data but found to have a significant correlation with human brain activity for the correlation based on the relative conversion blood-circulation-amount data is also recognized to have a significant correlation with human brain activity.

Table 3 below shows results of the contrast experiment.

TABLE 3

| | |
|---|---|
| Components having correlation with brain resting time/brain activation time | Component 1, Component 2 |
| Components having correlation with movement distance of face | Component 1, Component 3, Component 4 |
| Components having correlation with number of keyboard inputs | Component 8 |

As shown in Table 3, in the contrast experiment, when the test subject moves during the acquisition of captured face image data, the component 2 among components whose amplitudes of the component waveforms have a significant correlation with each of the brain deactivation time and the brain activation time was found to have no significant correlation with each of the movement distance and the number of keyboard inputs. This indicates that, among a plurality of components obtained by performing the singular value decomposition on the blood-circulation-amount data based on the RGB data acquired from the captured face image data, a component having a significant correlation with brain activity is affected much less by the movement of the test subject during the acquisition of time-series captured face image data, if any, than by the brain activities of the brain (than by the activation or deactivation of the brain).

From these results, the inventors have obtained the following findings.

As a result of decomposing the blood-circulation-amount data obtained from the face RGB data based on the time-series captured face image data acquired from the test subject into a plurality of components by using the singular value decomposition and analyzing the components obtained through decomposition, the components 1, 2, 3, 4, and 5 among the plurality of components were found to be components related to brain activity. That is, the blood-circulation-amount data obtained from the face RGB data based on the time-series captured face image data is decomposed into a plurality of components by using the singular value decomposition, a component having a correlation with the activation/deactivation of the brain is extracted from the plurality of components obtained through decomposition, and the extracted component is analyzed. Accordingly, it has turned out that a component indicating a face RGB change reflecting brain activity can be identified from the plurality of components. From this, the inventors have obtained findings that brain activity can be estimated on the basis of time-series captured face image data of a person.

(4) Brain Activity Visualization Device

Next, brain activity visualization devices 10 and 110 according to an embodiment of the present invention, which has been achieved by the inventors on the basis of the findings described above, will be described. A brain activity visualization device according to the present invention is not limited to that in the following embodiment and may be modified as appropriate without departing from the scope of the invention.

The brain activity visualization devices 10 and 110 according to an embodiment of the present invention includes a brain activity estimation means 30 for estimating brain activity on the basis of facial skin temperature data, and/or a brain activity estimation means 130 for estimating brain activity on the basis of captured face image data. In the following, before the description of the brain activity visualization devices 10 and 110 according to an embodiment of the present invention, the brain activity estimation means 30 and 130 will be described.

Figure 19:
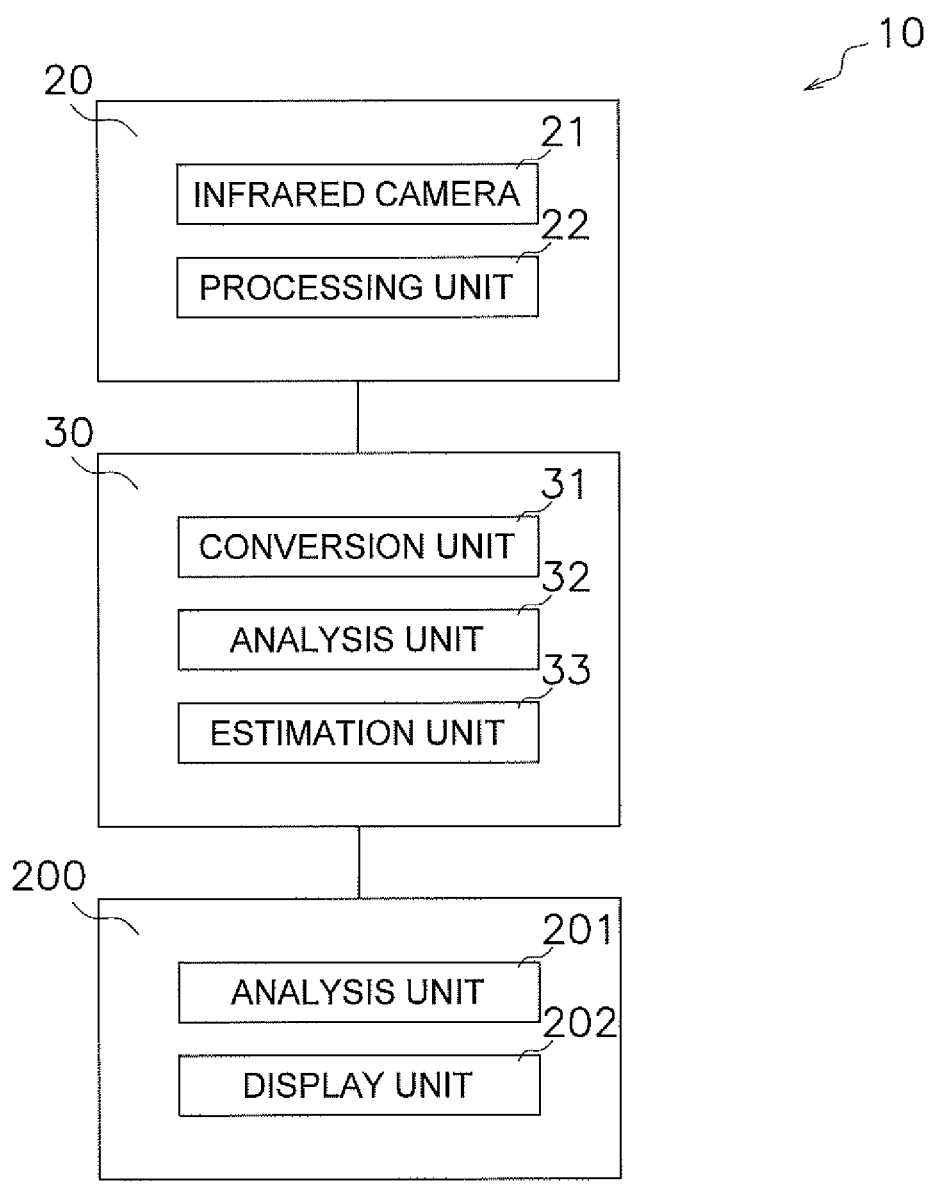
FIG. 19 is a diagrammatic illustration of a brain activity visualization device according to an embodiment of the present invention.
Figure 20:
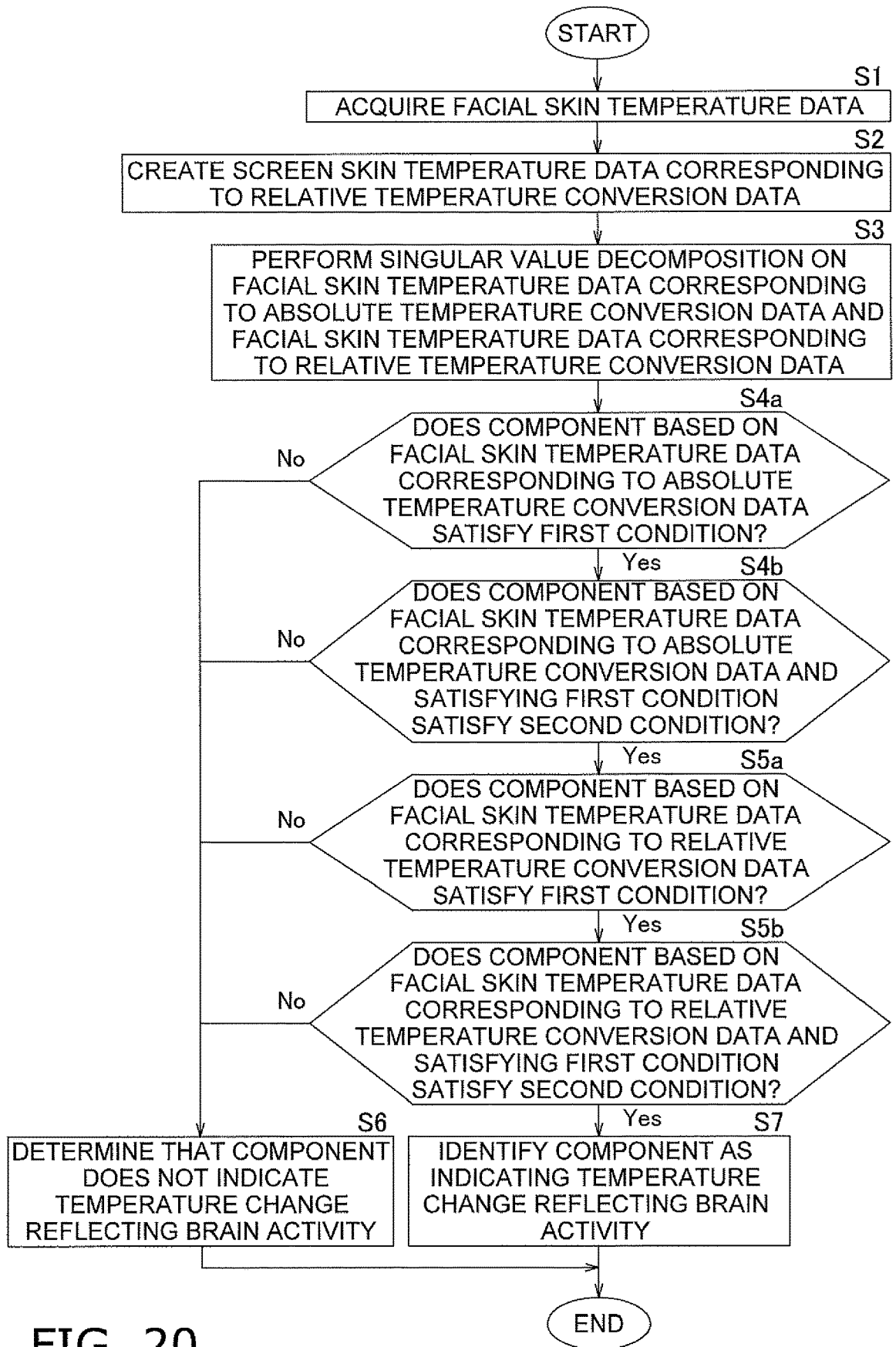
FIG. 20 is a flowchart illustrating an example of process flow in the brain activity visualization device to identify a component indicating a skin temperature change reflecting the brain function.

(4-1) Brain activity estimation means 30 for estimating brain activity on the basis of facial skin temperature data FIG. 19 is a diagrammatic illustration of the brain activity visualization device 10 according to an embodiment of the present invention. FIG. 20 is a flowchart illustrating process flow in the brain activity visualization device 10 to identify a component indicating a skin temperature change reflecting the brain function.

The brain activity estimation means 30 of the brain activity visualization device 10 estimates the brain activity of a person (test subject) from the facial skin temperature of the person. As illustrated in FIG. 19, the brain activity visualization device 10 includes a facial skin temperature acquisition means 20, the brain activity estimation means 30, and a state visualization means 200.

The facial skin temperature acquisition means 20 detects the skin temperature of at least a portion of the face of a person and acquires in time series facial skin temperature data including the detected temperature data and location data of the detection region (step S1). Here, the facial skin temperature acquisition means 20 is an infrared thermography device. As illustrated in FIG. 19, the facial skin temperature acquisition means 20 includes an infrared camera 21 and a processing unit 22. The infrared camera 21 is used to detect infrared radiation energy emitted from the face of the person. The infrared camera 21 is assumed here to detect infrared radiation energy from the entire area of the face of the person. The processing unit 22 converts the infrared radiation energy detected by the infrared camera 21 into temperatures to generate temperature data, creates a temperature distribution diagram of facial skin temperatures on the entire area of the face in which a region where the infrared radiation energy has been detected is represented as location data (coordinate data), and processes the created temperature distribution diagram as facial skin temperature data corresponding to temperature conversion data. The facial skin temperature data corresponding to temperature conversion data is stored in a storage unit (not illustrated) included in the processing unit 22.

Here, the processing unit 22 creates a temperature distribution diagram of facial skin temperatures on the entire area of the face. However, this is not limiting. A temperature distribution diagram of facial skin temperatures including the temperatures of at least the paranasal-sinus surrounding area and/or the forehead portion may be created and used as facial skin temperature data corresponding to temperature conversion data.

In addition, while the facial skin temperature acquisition means 20 acquires facial skin temperature data corresponding to temperature conversion data, the person is presented with a brain function activation exercise for a certain period. That is, the facial skin temperature data corresponding to temperature conversion data, which is acquired by the facial skin temperature acquisition means 20, includes data obtained in a period during which the brain function activation exercise is presented to the person. The brain function activation exercise presented to the person is not specifically limited, and may be any exercise estimated to activate the brain. For example, the content of the brain function activation exercise may be determined as desired according to the purpose of use of the brain activity visualization device 10.

The brain activity estimation means 30 estimates human brain activity on the basis of the facial skin temperature data corresponding to temperature conversion data, which is acquired by the facial skin temperature acquisition means 20. Specifically, as illustrated in FIG. 19, the brain activity estimation means 30 includes a conversion unit 31, an analysis unit 32, and an estimation unit 33.

The conversion unit 31 converts the temperature data included in the facial skin temperature data corresponding to temperature conversion data into relative temperature data and creates facial skin temperature data based on the converted relative temperature data, that is, facial skin temperature data corresponding to relative temperature conversion data (step S2). Specifically, the conversion unit 31 converts temperature data included in facial skin temperature data corresponding to temperature conversion data obtained at intervals of a predetermined time (e.g., 30 seconds) into relative temperature data by using the average value of the temperature data as a reference value. Then, the conversion unit 31 creates facial skin temperature data corresponding to relative temperature conversion data by utilizing the converted relative temperature data and the location data.

The analysis unit 32 decomposes each of the facial skin temperature data corresponding to time-series temperature conversion data and the facial skin temperature data corresponding to relative temperature conversion data into a plurality of components by using singular value decomposition, principal component analysis, or independent component analysis (step S3). Here, the analysis unit 32 performs the singular value decomposition on each of the facial skin temperature data corresponding to the acquired temperature conversion data and the facial skin temperature data corresponding to the converted relative temperature conversion data by using SVD of MATLAB (registered trademark) as an analysis tool. The singular value decomposition is performed on the facial skin temperature data corresponding to temperature conversion data acquired in time series and the facial skin temperature data corresponding to relative temperature conversion data, in which the factor is time data obtained at intervals of a predetermined period (e.g., 30 seconds) and the measure is the facial skin temperature data corresponding to temperature conversion data within the period and the facial skin temperature data corresponding to relative temperature conversion data. Through the singular value decomposition, each of the facial skin temperature data corresponding to temperature conversion data and the facial skin temperature data corresponding to relative temperature conversion data is decomposed into a plurality of components, and a temporal distribution, a spatial distribution, and a singular value indicating the magnitude of each component are calculated.

Further, the analysis unit 32 determines whether each component satisfies a first condition and a second condition to identify a component indicating a skin temperature change reflecting brain activity from the plurality of components obtained through decomposition using the singular value decomposition (steps S4a, S4b, S5a, and S5b). The analysis unit 32 first determines whether each component based on the facial skin temperature data corresponding to temperature conversion data satisfies the first condition (step S4a), and determines whether a component based on the facial skin temperature data corresponding to temperature conversion data that is determined in step S4a to satisfy the first condition satisfies the second condition (step S4b). Then, the analysis unit 32 focuses only on a component matching the component determined in steps S4a and S4b to satisfy the first condition and the second condition among the components based on the facial skin temperature data corresponding to relative temperature conversion data, and determines whether this component satisfies the first condition (step S5a). Thereafter, the analysis unit 32 determines whether a component based on the facial skin temperature data corresponding to relative temperature conversion data that is determined in step S5a to satisfy the first condition satisfies the second condition (step S5b). However, the order of the determination performed by the analysis unit 32 is not limited to that described above. For example, it may be determined whether the components based on the facial skin temperature data corresponding to temperature conversion data and the components based on the facial skin temperature data corresponding to relative temperature conversion data each satisfy the first condition and the second condition, and a component for which the determination results match may be finally extracted.

The first condition is a condition in which the amplitude of the component waveform of a component obtained through decomposition using the singular value decomposition has a correlation with changes during the brain deactivation time and the brain activation time. The analysis unit 32 extracts as a determination component a component satisfying the first condition from among the plurality of components. During the acquisition of the facial skin temperature data corresponding to temperature conversion data, a brain function activation exercise is presented to a person for a certain period. The analysis unit 32 compares and analyzes the component waveform of each component and each of the period during which the brain function activation exercise is presented and the period during which no brain function activation exercise is presented, where the period during which no brain function activation exercise is presented to the person is defined as the brain deactivation time and the period during which the brain function activation exercise is presented to the person is defined as the brain activation time. The analysis unit 32 evaluates whether there is a correlation between the component waveform of each component and each of the brain deactivation time and the brain activation time by utilizing comparison and analysis results based on the component waveform data, and extracts a component evaluated to have a correlation with each of the brain deactivation time and the brain activation time among the plurality of components as a determination component satisfying the first condition. On the other hand, the analysis unit 32 determines that a component evaluated to have no correlation with each of the brain deactivation time and the brain activation time among the plurality of components does not satisfy the first condition and is not a component indicating a temperature change reflecting human brain activity (step S6).

Here, a person is presented with a brain function activation exercise for a certain period during the acquisition of the facial skin temperature data corresponding to temperature conversion data, and the analysis unit 32 extracts a determination component accordingly. However, the content of the first condition, that is, the determination component extraction means in the analysis unit 32, is not limited thereto. For example, if a component exhibiting a component waveform having a correlation with the brain deactivation time and the brain activation time is identified from the plurality of components by experiment or the like conducted in advance, the analysis unit 32 extracts the identified component from the plurality of components as a determination component. When a human movement known to be related to the activation/inactivation of the brain, such as eye movement or blinking, is detected in this brain activity visualization device, the analysis unit 32 may compare, analyze, and evaluate the detection result and the component waveform of each component to extract a determination component from the plurality of components. The criterion by which the analysis unit 32 determines whether the first condition is satisfied is determined, as appropriate, by simulation, experiment, desktop calculations, or the like according to the purpose of use or the like of the brain activity visualization device 10.

The second condition is a condition in which temperature changes in a predetermined region on the human face for the extracted determination component. The analysis unit 32 determines that a component that is the determination component and that satisfies the second condition is likely to be related to human brain activity, and extracts the component as a candidate component. That is, the analysis unit 32 determines whether the determination component is related to human brain activity on the basis of the presence of a temperature change in a predetermined region on the human face. Specifically, the analysis unit 32 determines whether a temperature change has occurred in the paranasal-sinus surrounding area and/or the forehead portion on the basis of temperature distribution data of the extracted determination component. If a temperature change has occurred, the determination component is determined to satisfy the second condition and to be a component that is likely to be related to human brain activity, and is extracted as a candidate component. On the other hand, no temperature change has occurred in the paranasal-sinus surrounding area and/or the forehead portion, the analysis unit 32 determines that the determination component does not satisfy the second condition and is not a component indicating a skin temperature change reflecting brain activity (step S6). The criterion by which the analysis unit 32 determines whether the second condition is satisfied is determined, as appropriate, by simulation, experiment, desktop calculations, or the like according to the purpose of use or the like of the brain activity visualization device 10.

Then, the analysis unit 32 identifies the component determined in step S5b to satisfy the second condition as a component indicating a skin temperature change reflecting brain activity (step S7). That is, the component identified in step S7 as a component indicating a skin temperature change reflecting brain activity is a component that realizes that a match is found between the candidate component extracted by decomposing the facial skin temperature data corresponding to temperature conversion data by using the singular value decomposition and performing analysis and the candidate component extracted by decomposing the facial skin temperature data corresponding to relative temperature conversion data by using the singular value decomposition and performing analysis. Candidate components that do not match in both analyses are each determined in step S6 not to be a component indicating a skin temperature change reflecting brain activity.

The estimation unit 33 estimates human brain activity on the basis of the component identified by the analysis unit 32 as a component indicating a skin temperature change reflecting human brain activity. Specifically, the estimation unit 33 estimates the amount of brain activity during the acquisition of the facial skin temperature data on the basis of the component waveform data of the component identified by the analysis unit 32.

(4-1-1) Modification 1A

The brain activity estimation means 30 described above includes the conversion unit 31, and the conversion unit 31 creates facial skin temperature data corresponding to relative temperature conversion data. Then, the analysis unit 32 decomposes not only the facial skin temperature data corresponding to temperature conversion data, which is acquired by the facial skin temperature acquisition means 20, but also facial skin temperature data corresponding to relative temperature data based on temperature data converted to relative temperature data into a plurality of components by using the singular value decomposition, and analyzes each of the components.

Alternatively, the brain activity estimation means 30 may not include the conversion unit 31. In this case, the process of creating facial skin temperature data corresponding to relative temperature conversion data and analyzing data based on the facial skin temperature data corresponding to relative temperature conversion data may be omitted.

However, to accurately identify a component related to human brain activity, as in the embodiment described above, it is desirable that the brain activity estimation means 30 include the conversion unit 31 and that the analysis unit 32 decompose not only the facial skin temperature data corresponding to temperature conversion data, which is acquired by the facial skin temperature acquisition means 20, but also facial skin temperature data corresponding to relative temperature data based on temperature data converted to relative temperature data into a plurality of components by using the singular value decomposition and analyze each of the components.

(4-1-2) Modification 1B

The facial skin temperature acquisition means 20 described above is an infrared thermography device capable of acquiring temperature data in non-contact with a target object.

However, the facial skin temperature acquisition means is not limited to an infrared thermography device if it is capable of detecting the skin temperature of at least a portion of the face of a person and acquiring in time series facial skin temperature data including the detected temperature data and location data of the detection region.

For example, the facial skin temperature acquisition means may be a device including a temperature sensor. Specifically, a temperature sensor may be attached to a predetermined region on the face of a person, and time-series facial skin temperature data may be acquired on the basis of temperature data detected by the temperature sensor and on the basis of location data of the region to which the temperature sensor is attached. In this way, even when facial skin temperature data is acquired using a temperature sensor in contact with a target person, unlike electroencephalogram electrodes or the like, the temperature sensor, which does not require processing before attachment, can acquire data more easily than existing detection methods such as electroencephalography, magnetic resonance imaging, and near-infrared spectroscopy. This can facilitate estimation of human brain activity.

Figure 21:
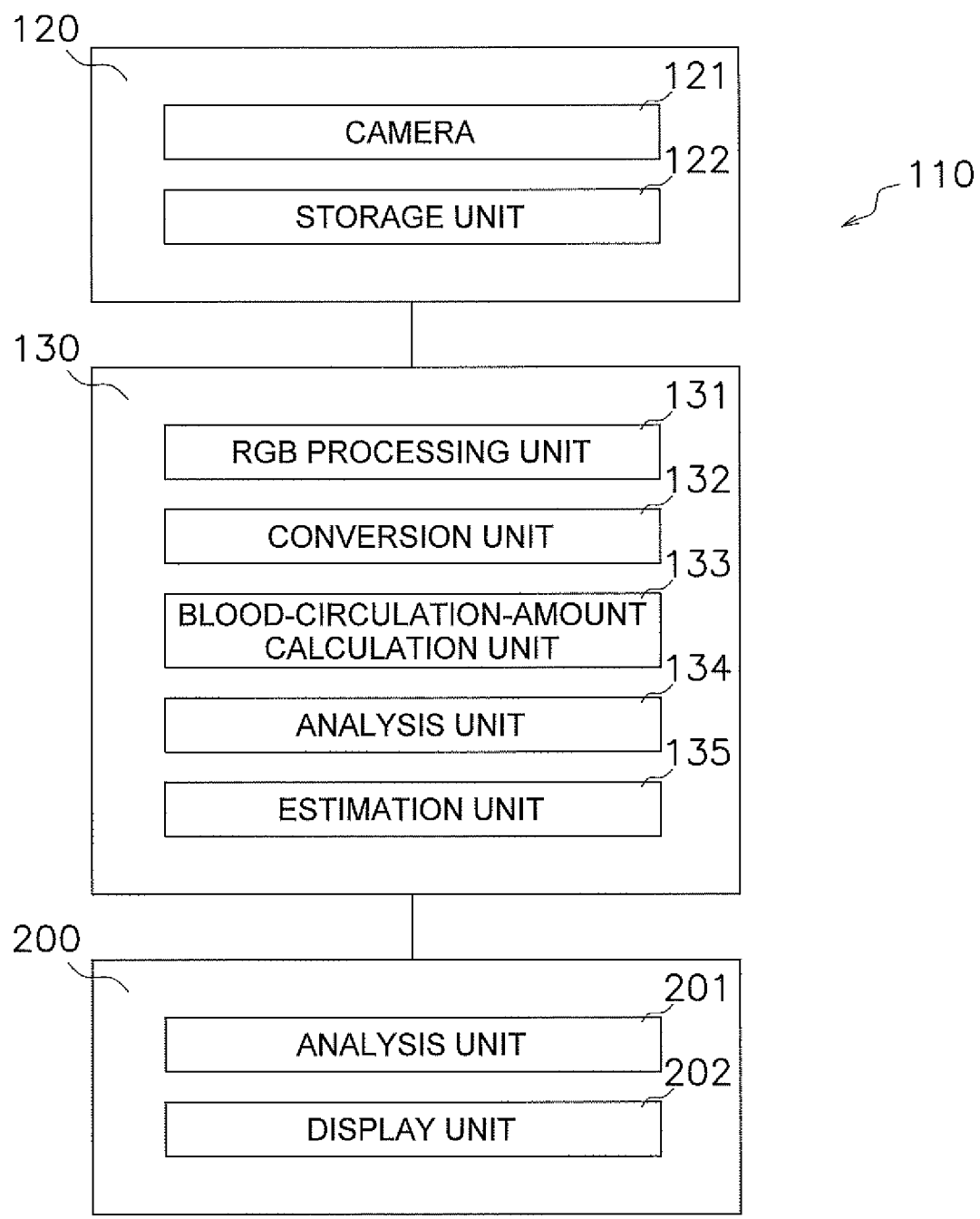
FIG. 21 is a diagrammatic illustration of a brain activity visualization device according to an embodiment of the present invention.
Figure 22:
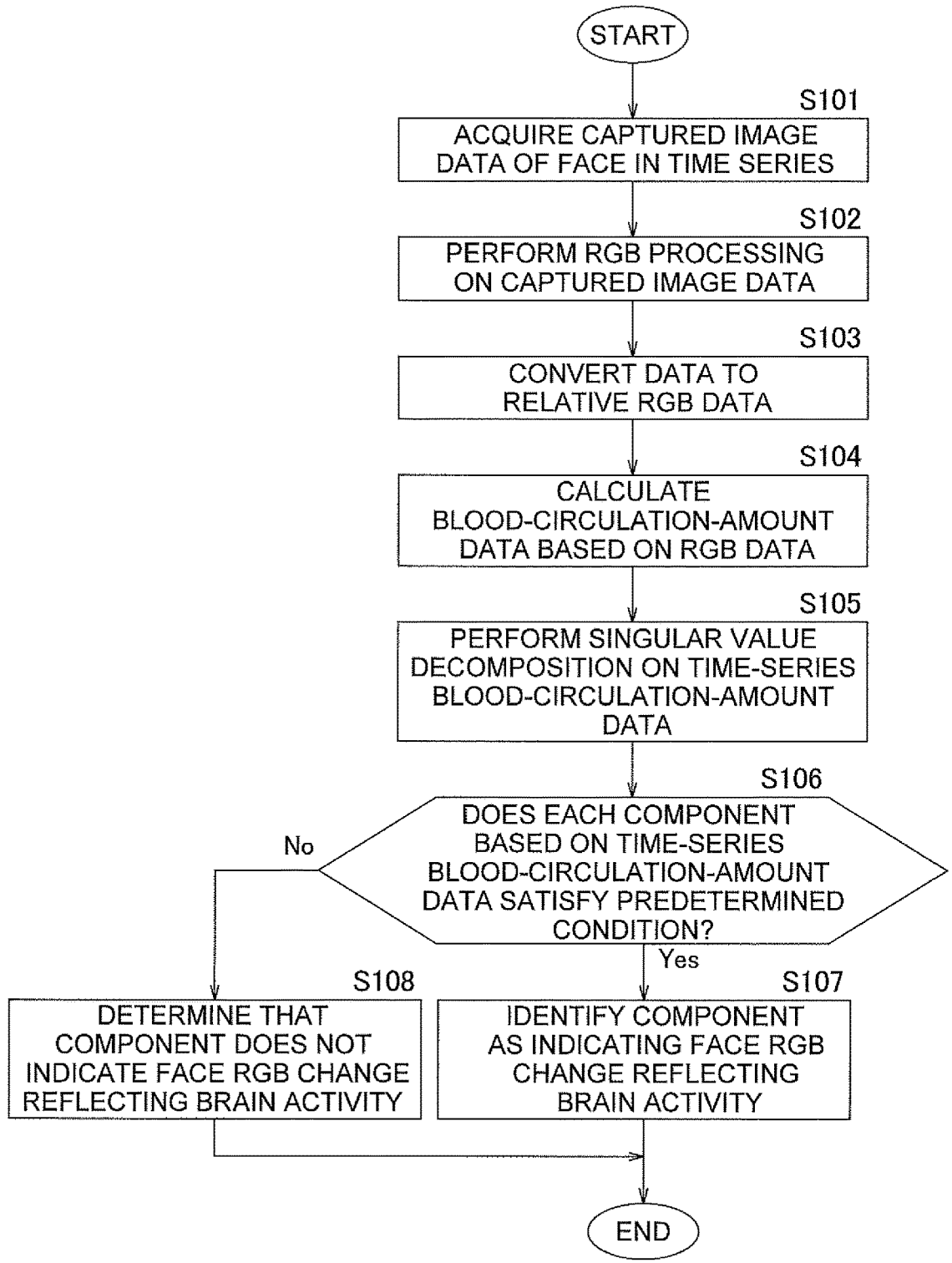
FIG. 22 is a flowchart illustrating an example of process flow in the brain activity visualization device to identify a component indicating a face RGB change reflecting the brain function.

(4-2) Brain activity estimation means 130 for estimating brain activity on the basis of captured face image data FIG. 21 is a diagrammatic illustration of the brain activity visualization device 110 according to an embodiment of the present invention. FIG. 22 is a flowchart illustrating an example of process flow in the brain activity visualization device 110 to identify a component indicating a face RGB change reflecting the brain function.

The brain activity estimation means 130 of the brain activity visualization device 110 is a device for estimating the brain activity of a person (test subject) from captured face image data of the person. As illustrated in FIG. 21, the brain activity visualization device 110 includes an image data acquisition means 120, the brain activity estimation means 130, and the state visualization means 200.

The image data acquisition means 120 acquires captured image data of at least a portion of the face of a person in time series (step S101). The image data acquisition means 120 is not limited if it includes at least an imaging device. Examples of the image data acquisition means 120 include portable terminals including an imaging device, such as a smartphone and a tablet (e.g., iPad: registered trademark). As illustrated in FIG. 21, the image data acquisition means 120 includes a camera 121 serving as an imaging device, and a storage unit 122. The camera 121 is used to acquire captured face image data of the person in time series. Here, the camera 121 captures a moving image of the entire area of the face of the person and acquires captured moving image data. The storage unit 122 stores time-series captured image data captured by the imaging device. Here, the storage unit 122 stores the moving image data acquired by the camera 121.

The camera 121 captures a moving image of the entire area of the face, which is not limiting. The camera 121 may capture a moving image including at least images of the forehead portion and/or the paranasal-sinus surrounding area of the face.

In addition, while the image data acquisition means 120 acquires time-series captured face image data, the person is presented with a brain function activation exercise for a certain period. That is, the captured image data acquired by the image data acquisition means 120 includes data obtained in a period during which the brain function activation exercise is presented to the person. The brain function activation exercise presented to the person is not specifically limited, and may be any exercise estimated to activate the brain. For example, the content of the brain function activation exercise may be determined as desired according to the purpose of use of the brain activity visualization device 110.

The brain activity estimation means 130 estimates human brain activity on the basis of the time-series captured face image data acquired by the image data acquisition means 120. Specifically, as illustrated in FIG. 21, the brain activity estimation means 130 includes an RGB processing unit 131, a conversion unit 132, a blood-circulation-amount calculation unit 133, an analysis unit 134, and an estimation unit 135. In FIG. 21, the brain activity estimation means 130 is illustrated as a single device including the RGB processing unit 131, the conversion unit 132, the blood-circulation-amount calculation unit 133, the analysis unit 134, and the estimation unit 135. However, the present invention is not limited to this, and some or each of the RGB processing unit 131, the conversion unit 132, the blood-circulation-amount calculation unit 133, the analysis unit 134, and the estimation unit 135 may be present as an independent device. Further, the image data acquisition means 120, the RGB processing unit 131, the conversion unit 132, and the blood-circulation-amount calculation unit 133 constitute a facial blood-circulation-amount acquisition means.

The RGB processing unit 131 performs RGB processing to decompose the captured image data acquired by the image data acquisition means 120 into three color components: an R component, a G component, and a B component (step S102). While RGB processing may be performed on captured image data of the entire area of the face, to reduce the amount of computation processing and noise, data of the forehead portion and/or the paranasal-sinus surrounding area is extracted from the captured image data, and only the extracted data is subjected to RGB processing.

The conversion unit 132 converts the RGB data of the captured image data obtained through RGB processing into relative RGB data (step S103). Specifically, the conversion unit 132 converts RGB data obtained from the captured image data acquired at intervals of a predetermined time (e.g., 30 seconds) into relative RGB data by using the average value of the RGB data as a reference value.

The blood-circulation-amount calculation unit 133 calculates time-series facial blood-circulation-amount data on the basis of the RGB data of the captured image data obtained through RGB processing (step S104).

The analysis unit 134 decomposes the time-series relative conversion blood-circulation-amount data into a plurality of components by using singular value decomposition, principal component analysis, or independent component analysis (step S105). Here, the analysis unit 134 performs the singular value decomposition on the relative conversion blood-circulation-amount data by using SVD of MATLAB (registered trademark) as an analysis tool. Specifically, the singular value decomposition is performed on the time-series relative conversion blood-circulation-amount data, in which the factor is time data obtained at intervals of a predetermined period (e.g., 30 seconds) and the measure is per-pixel relative conversion blood-circulation-amount data computed from relative RGB data within the period. Through the singular value decomposition, the time-series relative conversion blood-circulation-amount data is decomposed into a plurality of components, and a temporal distribution, a spatial distribution, and a singular value indicating the magnitude of each component are calculated.

Further, the analysis unit 134 determines whether each component satisfies a predetermined condition to identify a component indicating a face RGB change reflecting brain activity from the plurality of components obtained through decomposition using the singular value decomposition (step S106). Examples of the predetermined condition include a condition in which the amplitude of the component waveform of a component obtained through decomposition using the singular value decomposition has a correlation with changes during the brain deactivation time and the brain activation time (hereinafter referred to as first condition), and a condition in which a change in the amount of blood circulation changes in a predetermined region on the human face for a component obtained through decomposition using the singular value decomposition (hereinafter referred to as second condition). One or more conditions may be set as the predetermined condition on which the determination performed by the analysis unit 134 is based. Here, the first condition is set as the predetermined condition.

Then, the analysis unit 134 extracts a component satisfying the predetermined condition from the plurality of components as a determination component. Further, the analysis unit 134 identifies a component that is an extracted determination component and that satisfies all the conditions included in the predetermined condition as a component indicating a face RGB change reflecting brain activity (step S107). On the other hand, the analysis unit 134 determines that a component determined not to satisfy at least one of the conditions included in the predetermined condition among the plurality of components is not a component indicating a face RGB change reflecting brain activity (step S108).

As described above, only one condition (the first condition) is set as the predetermined condition, and a brain function activation exercise is presented to the person for a certain period during the acquisition of time-series captured face image data. Accordingly, the analysis unit 134 compares and analyzes the component waveform of each component and each of the period during which the brain function activation exercise is presented and the period during which no brain function activation exercise is presented, where the period during which no brain function activation exercise is presented to the person is defined as the brain deactivation time and the period during which the brain function activation exercise is presented to the person is defined as the brain activation time. Then, the analysis unit 134 evaluates whether there is a correlation between the component waveform of each component and each of the brain deactivation time and the brain activation time by utilizing comparison and analysis results based on the component waveform data, and extracts a component evaluated to have a correlation with each of the brain deactivation time and the brain activation time among the plurality of components as a determination component satisfying the predetermined condition. Also, the analysis unit 134 identifies the extracted component as a component indicating a face RGB change reflecting brain activity. On the other hand, the analysis unit 134 determines that a component evaluated to have no correlation with each of the brain deactivation time and the brain activation time among the plurality of components does not satisfy the predetermined condition and is not a component indicating a face RGB change reflecting human brain activity.

Here, a person is presented with a brain function activation exercise for a certain period during the acquisition of time-series captured face image data, and the analysis unit 134 extracts a determination component accordingly. However, the content of the first condition, that is, the determination component extraction means in the analysis unit 134, is not limited thereto. For example, if a component exhibiting a component waveform having a correlation with the brain deactivation time and the brain activation time is identified from the plurality of components by experiment or the like conducted in advance, the analysis unit 134 extracts the identified component from the plurality of components as a determination component. When a human movement known to be related to the activation/inactivation of the brain, such as eye movement or blinking, is also detected in the brain activity visualization device 110, the analysis unit 134 may compare, analyze, and evaluate the detection result and the component waveform of each component to extract a determination component from the plurality of components. The criterion by which the analysis unit 134 determines whether the first condition is satisfied is determined, as appropriate, by simulation, experiment, desktop calculations, or the like according to the purpose of use or the like of the brain activity visualization device 110.

When the second condition is set as the predetermined condition, the analysis unit 134 extracts a determination component on the basis of the presence of a change in the amount of facial blood circulation in a predetermined region on the human face. Specifically, the analysis unit 134 determines whether a change in the amount of blood circulation has occurred in the paranasal-sinus surrounding area and/or the forehead portion on the basis of blood circulation amount distribution diagrams corresponding to the plurality of components obtained by decomposition using the singular value decomposition. If a change in the amount of blood circulation has occurred, the analysis unit 134 determines that the component satisfies the second condition. On the other hand, if no change in the amount of blood circulation has occurred in the paranasal-sinus surrounding area and/or the forehead portion, the analysis unit 134 determines that the component does not satisfy the second condition. The criterion by which the analysis unit 134 determines whether the second condition is satisfied is determined, as appropriate, by simulation, experiment, desktop calculations, or the like according to the purpose of use or the like of the brain activity visualization device 110.

If the blood-circulation-amount calculation unit 133 calculates time-series blood-circulation-amount data based on RGB data obtained before conversion to the relative RGB data, the analysis unit 134 may also determine whether each of the plurality of components obtained by performing the singular value decomposition or the like on the blood-circulation-amount data satisfies the first condition and/or the second condition, and extract a determination component.

The estimation unit 135 estimates human brain activity on the basis of the component identified by the analysis unit 134 as a component indicating a face RGB change reflecting human brain activity. Specifically, the estimation unit 135 estimates the amount of brain activity during the acquisition of captured face image data on the basis of the component waveform data of the component identified by the analysis unit 134.

(4-2-1) Modification 2A

As described above, a portable terminal including an imaging device, such as a smartphone or a tablet (e.g., iPad: registered trademark), may be used as the camera 121. That is, the captured image data described above may be obtained by capturing an image of a visible light area.

The blood-circulation-amount calculation unit 133 described above may calculate facial blood-circulation-amount data by using, mainly, the R component among the pixels included in RGB data. The blood-circulation-amount data is not necessarily limited to an erythema index if blood-circulation-amount data can be calculated on the basis of RGB data.

(4-2-2) Modification 2B

The blood-circulation-amount calculation unit 133 described above calculates relative conversion blood-circulation-amount data on the basis of the relative RGB data converted by the conversion unit 132. Alternatively or additionally, blood-circulation-amount data may be calculated on the basis of the RGB data obtained before conversion to the relative RGB data. In the blood-circulation-amount data calculated on the basis of the RGB data obtained before conversion to the relative RGB data, a component having a correlation with brain activity is likely to appear (verified with high performance). Accordingly, for example, the blood-circulation-amount data calculated on the basis of the RGB data obtained before conversion to the relative RGB data may be analyzed prior to the relative conversion blood-circulation-amount data calculated on the basis of relative RGB data. In addition, for example, first, the blood-circulation-amount data may be analyzed to extract a component having a significant correlation, and, for the relative conversion blood-circulation-amount data, only the component corresponding to the extracted component may be analyzed to reduce the amount of computation processing.

(4-2-3) Modification 2C

The camera 121 described above is assumed to be an ordinary camera for visible-light areas. Alternatively, an infrared camera may be used. In this case, the infrared camera emits infrared light and receives the reflection of infrared light. Accordingly, captured image data indicating a change or the like in the subject's face can be obtained. The inventors have found that there is a correlation between blood-circulation-amount data calculated from captured image data obtained by the reflection of infrared radiation and blood-circulation-amount data calculated by mainly using the R component among the pixels included in RGB data of a captured image of a visible light area. Accordingly, even with the use of such captured image data obtained from the reflection of infrared radiation, human brain activity can be estimated.

(4-2-4) Modification 2D

In the foregoing description, the brain activity visualization device 110 includes the image data acquisition means 120 and the brain activity estimation means 130. However, the brain activity visualization device according to this embodiment is not limited thereto. That is, it is only required that the brain activity visualization device according to this embodiment includes the blood-circulation-amount calculation unit 133, the analysis unit 134, and the estimation unit 135, and the other elements may have any configuration. Specifically, the brain activity visualization device according to this embodiment may be configured not only to capture image data but also to receive captured image data from an external device and analyze the received captured image data.

(4-3) State Visualization Means 200

The state visualization means 200 visualizes the physiological state of a subject by displaying it on the basis of the brain activity of the subject estimated by the brain activity estimation means 30 and/or the brain activity estimation means 130. For example, the state visualization means 200 may include an analysis unit 201 that analyzes a change in the amount of brain activity of the subject to analyze the physiological state of the subject. Specifically, the analysis unit 201 analyzes a change in the amount of brain activity in response to a stimulus (such as a visual stimulus, an auditory stimulus, a tactile stimulus, an olfactory stimulus, or a gustatory stimulus) applied to the subject to determine the physiological state of the subject. The type or level of the physiological state may be set as appropriate on the basis of the degree of increase in the amount of brain activity and/or the duration of the increase according to the use of the brain activity visualization devices 10 and 110. The physiological state of the subject analyzed by the analysis unit 201 is output from a display unit 202 of the state visualization means 200 to an administrator. Accordingly, the administrator is able to understand the physiological state of the subject. The display unit 202 may be any device capable of making information concerning the analyzed physiological state of the subject visible to the administrator, such as a display device that displays an image or a message.

After the analysis units 32 and 134 identify a component that reflects brain activity, the facial skin temperature acquisition means 20 and/or the image data acquisition means 120 may further acquire various time-series data. In this case, in the brain activity visualization devices 10 and 110, the further acquired various data is decomposed into a plurality of components by using the singular value decomposition, and only the identified component is analyzed to provide a real-time notification of the physiological state of the subject.

There have been techniques for acquiring heart rate information, biometric information, or the like of a test subject from the facial skin temperature of the test subject or from a captured image of the test subject. Such existing techniques are employed for a component obtained by subjecting various data obtained from the facial skin temperature acquisition means 20 and/or the image data acquisition means 120 to the singular value decomposition or the like, thereby accurately acquiring heart rate information or biometric information. Accordingly, the analysis unit 32 and/or the analysis unit 134 may have a function of analyzing the plurality of components obtained through the singular value decomposition to acquire heart rate information or biometric information, and the estimation units 33 and 135 of the embodiment described above may have a function of estimating the activity of the sympathetic/parasympathetic nervous systems on the basis of the acquired heart rate information or biometric information.

(5) Features (5-1)

In this embodiment, human brain activity is estimated on the basis of time-series facial skin temperature data and/or facial blood-circulation-amount data acquired by the facial skin temperature acquisition means 20 and/or the image data acquisition means 120. Accordingly, human brain activity can be estimated without using a sensor that requires processing before attachment, such as electroencephalogram electrodes. This can facilitate estimation of human brain activity, and enables visualization of the physiological state of the subject on the basis of the estimated brain activity.

(5-2)

When a situation is created in which the brain of a person is activated or deactivated by actually presenting a brain function activation exercise to the person or not during the acquisition of time-series facial skin temperature data and/or image data, a component whose component waveform has a correlation with the brain activation and deactivated times may be a component that is likely to be a component indicating a change in skin temperature and/or the amount of blood circulation that reflects brain activity.

In this embodiment, while the facial skin temperature acquisition means 20 and/or the image data acquisition means 120 acquires time-series facial skin temperature data and/or image data, a person is presented with a brain function activation exercise for a certain period. That is, in this embodiment, a situation is created in which the brain of a person is activated or deactivated by actually presenting a brain function activation exercise to the person or not. Then, the acquired various time-series data is decomposed into a plurality of components by using the singular value decomposition, the correlation between the component waveform of each of the components and the brain activation and deactivated times is evaluated, and a component having a correlation with the brain activation and deactivated times is extracted from the plurality of components as a determination component. Accordingly, compared to when, for example, a predetermined component identified in advance by experiment or the like is extracted from the plurality of components as an extraction component, the possibility of extracting a component having low relevance to human brain activity from the plurality of components as an extraction component can be reduced.

(5-3)

The brain has a mechanism for cooling the brain while leaving the body temperature unchanged, called a selective brain cooling system. The selective brain cooling system is known to dissipate heat generated by brain activity through the forehead portion and the to paranasal-sinus surrounding area. Thus, a change in the amount of facial blood circulation, which is correlated with the facial skin temperature or facial skin temperature that changes with brain activity, appears in the forehead portion and/or the paranasal-sinus surrounding area.

In this embodiment, various data of the forehead portion and/or the paranasal-sinus surrounding area is analyzed, and a determination component is extracted. Accordingly, a component related to human brain activity can be extracted accurately.

(6) Example Use of Brain Activity Visualization Device

Next, an example use of the brain activity visualization device according to the present invention will be described.

(6-1) Use for Patient

An example of a case will be described where the brain activity visualization devices 10 and 110 of the embodiment or modification described above are used for, for example, a patient who visits the hospital. For example, when the brain activity visualization devices 10 and 110 are used to objectively quantify the state of depression, a brain function activation exercise such as mental arithmetic with carrying or borrowing is presented to a patient, and a change in the amount of brain activity before and after the brain activity activation exercise is presented is analyzed and visualized to determine the mental health status of the patient. Specifically, when the amount of brain activity does not increase in the period during which the brain function activation exercise is presented, the patient's lack of motivation can be determined. Even when the amount of brain activity increases in the period during which the brain function activation exercise is presented, if the duration of the increase in the amount of brain activity is short, the patient can be determined to have low motivation. Such analysis is performed multiple times a day. If a decrease in the amount of brain activity is observed on average, the administrator can determine that the patient has suffered from depression.

When the brain activity visualization devices 10 and 110 are used to determine whether an emergency patient is conscious or whether a patient is awake, a stimulus, such as massage to skin or word, is presented to the patient, and a change in the amount of brain activity before and after the presentation of the stimulus is analyzed and visualized to determine whether the patient is conscious or whether the patient is awake. For example, when the amount of brain activity increases in the period during which the patient under anesthesia is given a stimulus to the skin, a word, or the like, the patient can be determined to be awake. Accordingly, even if the patient is unable to say a word, the administrator can know whether the patient is conscious or whether the patient is awake. In addition, the intensity of the stimulus presented to the patient can be changed, and whether the brain is activated during the to change can be analyzed to determine the degree (level) of awakening. Examples of the low-intensity stimulus include grasping a hand and moving a hand. Examples of the high-intensity stimulus include a stimulus that changes the body temperature, such as directing ice on the hand, and a stimulus that causes pain in the body.

When the brain activity visualization devices 10 and 110 are used to determine the effect of therapy such as rehabilitation, a patient is presented with a brain function activation exercise such as mental arithmetic with carrying or borrowing, and a change in the amount of brain activity during the presentation of the brain function activation exercise can be analyzed and visualized to determine the effect of therapy such as rehabilitation for the patient. For example, brain function activation exercises having the same intensity are presented to a patient before and after rehabilitation, brain training, or exercise therapy is performed, and a change in the amount of brain activity during the presentation of the brain function activation exercises is analyzed. Accordingly, the administrator is able to determine the effect of therapy such as rehabilitation from the degree of increase in the amount of brain activity or the duration of the increase. For example, if the amount of brain activity does not increase when a brain function activation exercise is presented to a patient, it can be determined that the patient has suffered cerebral ischemia. If the duration of the increase in the amount of brain activity is short, the volume of blood flow in cerebral blood vessels can be determined to be low. Accordingly, each of the brain activity visualization devices 10 and 110 can also be used as a monitoring device in a high-pressure oxygen therapy machine.

When the brain activity visualization devices 10 and 110 are used to quantify the pain of the patient, pain intensity may be quantified from a change in the amount of brain activity (in particular, the degree of increase in the amount of brain activity and the duration of the increase) during a period over which the patient feels pain (when reported by the patient). Visualizing the analysis result allows the administrator to know the pain level of the patient.

(6-2) Use for People in Extreme Conditions Subjected to Shock Waves and the like An example of a case will be described where the brain activity visualization devices 10 and 110 of the embodiment or modification described above are used for people in extreme conditions subjected to explosion shock waves, such as firefighters. When the brain activity visualization devices 10 and 110 are used to determine protection against a shock wave and the like striking a living body (e.g., determine the state of damage of the living body by the shock wave), the subject is presented with a brain function activation exercise, and a change in the amount of brain activity during the presentation of the brain function activation exercise is analyzed and visualized, which enables the administrator to estimate the state of blood flow in cerebral blood vessels of the subject. For example, if the amount of brain activity does not increase in the period during which the brain function activation exercise is presented to the subject, it can be determined that the subject has suffered cerebral ischemia. If the duration of the increase in the amount of brain activity is short, the volume of blood flow in cerebral blood vessels can be determined to be low.

(6-3) Use for Comfort Determination

An example of a case will be described where the brain activity visualization devices 10 and 110 of the embodiment or modification described above are used to determine the comfort of a subject. For example, when the brain activity visualization devices 10 and 110 are used to determine living comfort, the level of discomfort is quantified from a change in the amount of brain activity (the degree of increase in the amount of brain activity and the duration of the increase) during a period over which a subject in a predetermined living space feels discomfort (when reported by the subject). Such analysis is performed multiple times a day, and visualizing the results of the analysis allows the administrator to evaluate whether the amount of brain activity rises on average to determine the comfort level, that is, comfort/discomfort feeling, of the subject.

(6-4) Use for Concentration Level Determination

An example of a case will be described where the brain activity visualization devices 10 and 110 of the embodiment or modification described above are used to determine a person's concentration level during learning or surgery. For example, when the brain activity visualization devices 10 and 110 are used to quantify the degree of concentration of a learner on learning in school, tutoring school, company, e-learning, the hospital, or the like, a change in the amount of brain activity (the degree of increase) during a certain period (e.g., learning time) before and after the learning (exercise) activities of the learner can be analyzed to quantify the degree of concentration of the learner on the content of the learning activities of the learner. Accordingly, the administrator is able to evaluate the degree of concentration of the learner on the content of learning on the basis of visualized analysis results.

(7) Mental Illness Determination Device

A mental illness determination device will be described, which is an application of a brain activity visualization device according to the present invention. The mental illness determination device determines the mental or physical physiological state of a subject. Specifically, the studies made by the inventors have shown that depressed people respond slower to positive images or the like described below than non-depressed people. In contrast, depressed people tend to have higher response to negative images or the like than non-depressed people. Accordingly, the inventors have devised a depression state determintion device that determines a state of depression by utilizing the characteristics described above. As an extension, the inventors further have devised a mental illness determination device that determines the state of mental illness of a subject.

(7-1) Configuration of Mental Illness Determination Device

Figure 23:
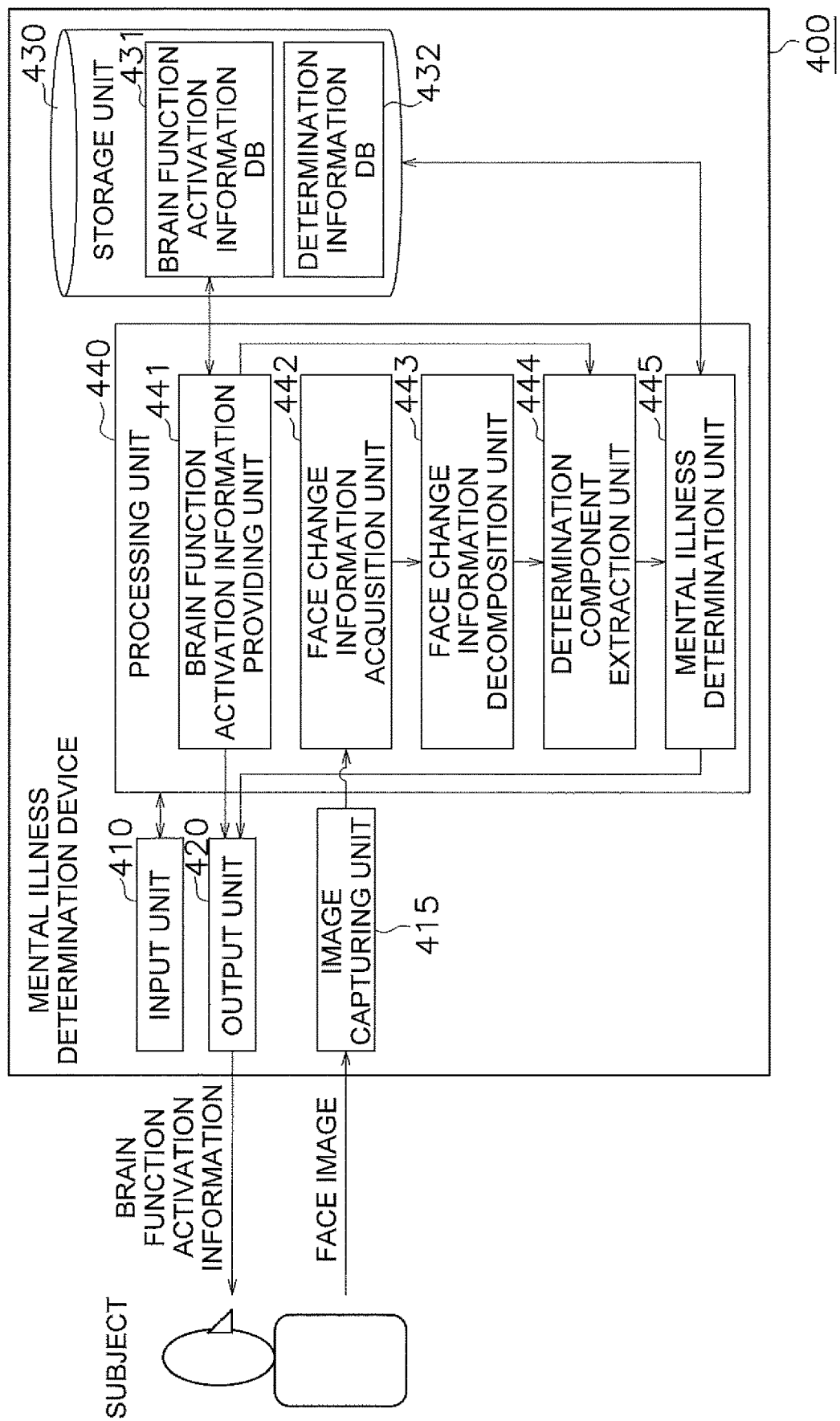
FIG. 23 is a schematic diagram illustrating a configuration of a mental illness determination device according to an embodiment of the present invention.

FIG. 23 is a schematic diagram illustrating an example of a mental illness determination device according to this embodiment. In the following description, a description will be given of the determination of the state of "depression" as the state of mental illness, by way of example.

A mental illness determination device 400 includes an input unit 410, an image capturing unit 415, an output unit 420, a storage unit 430, and a processing unit 440.

The input unit 410 inputs various types of information to the mental illness determination device 400. For example, the input unit 410 is constituted by a keyboard, a mouse, a touch screen and/or the like. Various instructions are input to the mental illness determination device 400 through the input unit 410, and the processing unit 440 executes processes in accordance with the instructions.

The image capturing unit 415 captures a "face image" including the face of a subject 300. For example, the image capturing unit 415 is constituted by a solid-state imaging device that acquires an RGB image, such as a CCD device and a CMOS device, and an infrared camera or the like that acquires a thermogram, and so on. The infrared camera or the like is desirably capable of detecting temperatures from 29.0° C. to 37.0° C. in normal room temperature conditions with high sensitivity. Further, the image capturing unit 415 is capable of continuously capturing images at predetermined intervals. Face images are desirably captured from the front under constant illumination conditions. When a front image is not obtainable due to changes in posture, the three-dimensional shape of the face is estimated for a posture-change image by using a perturbation space method, and a front image is rendered from the shape to obtain a face image. For an illumination-change image, an illumination basis model of the face, which is constructed based on a diffuse reflection model, is used to obtain a face image under constant illumination conditions. Then, face images continuously captured by the image capturing unit 415 are delivered to the processing unit 440.

The output unit 420 outputs various types of information from the mental illness determination device 400. For example, the output unit 420 is constituted by a display, a speaker, and so on. Here, brain function activation information described below is provided to the subject 300 via the output unit 420.

The storage unit 430 stores information input to the mental illness determination device 400, information calculated by the mental illness determination device 400, and so on. For example, the storage unit 430 is constituted by a memory, a hard disk device, and so on. The storage unit 430 further stores programs for implementing the functions of the processing unit 440 described below. Here, the storage unit 430 includes a brain function activation information database 431 and a determination information database 432.

The brain function activation information database 431 stores brain function activation information for activating the human brain function. Examples of the "brain function activation information" include emotional stimulation information, which is classified according to the comfort and the degree of response a person. The "emotional stimulation information" is information for stimulating any sense or any combination of senses among the visual sense, the auditory sense, the olfactory sense, the gustatory sense, the tactile sense, and the somatic sensation to change the emotions of the subject. Examples of the emotional stimulation information include an emotional image. The "emotional image" is classified into a negative image or a positive image in terms of comfort. Specifically, examples of the positive image include a photograph of a bride, a photograph of playing puppies, and images that increase the psychological comfort of people, such as images of a smiling person, a beautiful scene of snowy mountains, and flowers. Examples of the negative image include images that decrease the psychological comfort of people, such as images of a sad looking person, a scene of dilapidated slum houses, a TV drama murder scene, a spider, or an insect, a snake, and a photograph of a hospital. Further, emotional stimulation information other than emotional images can also be classified into positive information that makes the subject comfortable and negative information that makes the subject less comfortable. For example, sounds that make the subject comfortable are classified as positive sounds, and sounds that make the subject less comfortable are classified as negative sounds. The senses other than the visual sense and the auditory sense are stimulated indirectly with emotional stimulation information. For example, when the olfactory sense is stimulated, output information of a positive scent that makes the subject comfortable is emotional stimulation information, and the positive scent is output from a scent generator or the like. In the following description, the positive information and the negative information are represented as "positive image or the like" and "negative image or the like", respectively, in some times. In addition, the "brain function activation information" is not limited to this, and predetermined visual information including any one or any combination of the following: the emotional image described above, an image-exposure image, a substance image, an image indicating a cognitive exercise, light stimulation information, and an image indicating a sense-stimulating exercise. The brain function activation information database 431 stores not only the emotional stimulation information described above for activating brain function but also an image that deactivates brain function or any other deactivation information. For example, the brain function activation information database 431 stores a "rest image" that deactivates brain function. Alternately presenting the rest image and the emotional image enables turning on and off of the activation of the brain function of the subject.

Figure 24:
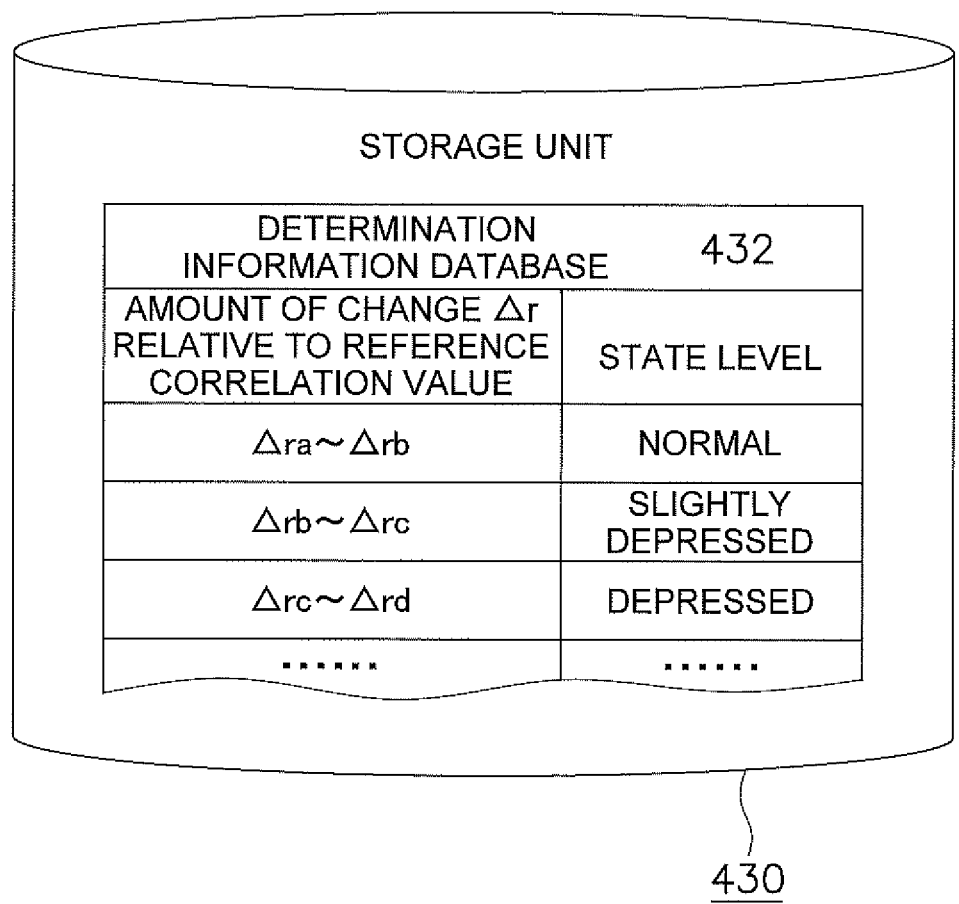
FIG. 24 is a schematic diagram illustrating a configuration of a determination information database in the mental illness determination device.

As illustrated in FIG. 24, the determination information database 432 stores, as "determination information" in advance, in association with the "state level", an amount of change $\Delta r$ (=r2−r1) of a correlation value r2 of a determination component extracted in response to the provision of the positive image or the like with respect to a "reference correlation value" r1 of a reference determination component extracted in response to the provision of the negative image or the like, the amount of change $\Delta r$ falling within a predetermined range. The amount of change $\Delta r$ is represented as the absolute value. The "reference determination component" is set by using data of the extracted determination component in response to the provision of the negative image or the like, data of the previously extracted determination component, data of a determination component provided from the outside, and so on.

The example illustrated in FIG. 24 shows the determination of the state level of "depression". Specifically, the determination information database 432 stores, in accordance with the range of values of the amount of change $\Delta r$, the range $\Delta r = \Delta r_a$ to $\Delta r_b$ as "normal", the range of $\Delta r_b$ to $\Delta r_c$ as "slightly depressed", and the range of $\Delta r_c$ to $\Delta r_d$ as "markedly depressed", with the values $\Delta r_a$, $\Delta r_b$, $\Delta r_c$, and $\Delta r_d$ arranged in ascending order. The determination information database 432 may also store the data of the reference determination component. Here, the determination information database 432 stores determination information for determining the state of "depression". When the state of any other mental illness is determined, the determination information database 432 stores corresponding determination information.

The processing unit 440 executes information processing performed in the mental illness determination device 400.

Specifically, the processing unit 440 is constituted by a CPU, a cache memory, and so on. The programs stored in the storage unit 430 are executed, thereby allowing the processing unit 440 to function as a brain function activation information providing unit 441, a face change information acquisition unit 442, a face change information decomposition unit 443, a determination component extraction unit 444, and a mental illness determination unit 445.

The brain function activation information providing unit 441 provides brain function activation information. For example, in response to the operation of the input unit 410, the brain function activation information providing unit 441 reads brain function activation information from the brain function activation information database 431 and outputs the brain function activation information to the output unit 420.

The face change information acquisition unit 442 acquires "face data" and "face change information" indicating a time-series change in the face data from the face image captured by the image capturing unit 415. Specifically, the face change information acquisition unit 442 acquires face data via the image capturing unit 415 in synchronization with the timing at which the brain function activation information providing unit 441 provides the brain function activation information. Further, the face change information acquisition unit 442 acquires face change information indicating a time-series change in the face data of the subject 300 from continuously acquired face data. For example, when 60 pieces of face data of 240×320 pixels are acquired at predetermined intervals, the face change information is a collection of 4,608,000 pieces of data. The acquired face change information is delivered to the face change information decomposition unit 443. When the image capturing unit 415 is an infrared camera, the face change information acquisition unit 442 acquires, as face data, facial skin temperature data indicating the facial skin temperatures of the subject 300. When the image capturing unit 415 is a solid-state imaging device such as a CCD device and a CMOS device, the face change information acquisition unit 442 acquires, as face data, facial blood-circulation-amount data based on face RGB data of the subject 300. The face change information acquisition unit 442 may acquire, as face data, only the data of the paranasal-sinus surrounding area and/or the forehead portion of the subject 300.

The face change information decomposition unit 443 decomposes the face change information, which is a collection of multiple pieces of data, into a plurality of components 1, 2, 3, . . . by using singular value decomposition, principal component analysis, or independent component analysis. Information on the components obtained through decomposition is delivered to the determination component extraction unit 444. When the face change information is subjected to the singular value decomposition or the like, the components 1, 2, 3, . . . are assigned in descending order of the singular values. In addition, a component having a higher singular value is more likely to be affected by a large variation. Accordingly, component 1 is usually affected by noise or the like in an external environment, rather than by the provision of the brain function activation information.

The determination component extraction unit 444 extracts, as the "determination component", a component related to the brain function activation information from the plurality of components 1, 2, 3 . . . . Specifically, the determination component extraction unit 444 calculates a correlation value r between each of the plurality of components 1, 2, 3, . . . determined by the face change information decomposition unit 443 and the "determination waveform" corresponding to the brain function activation information.

Figure 25:
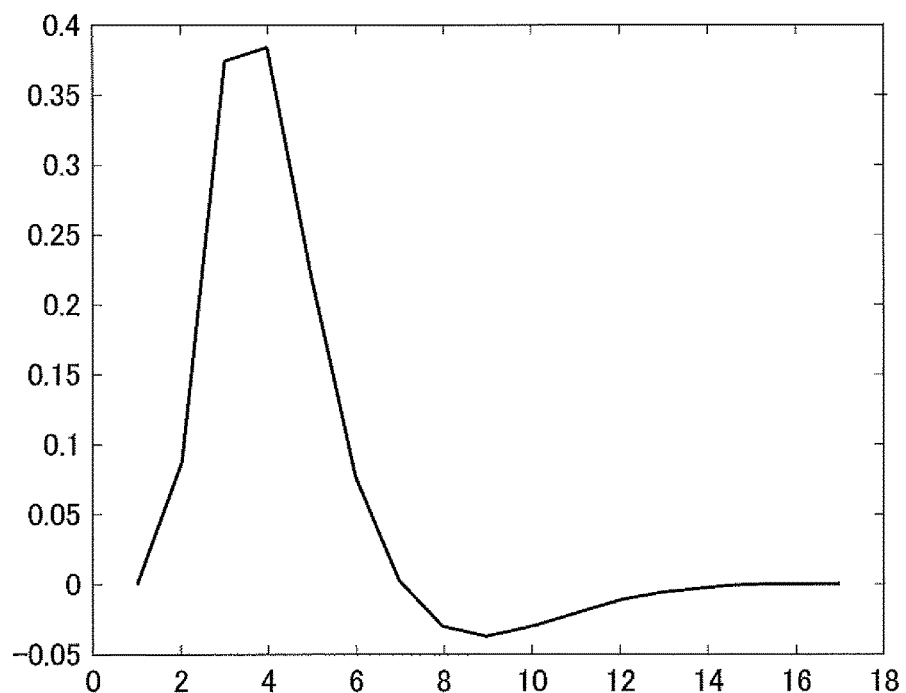
FIG. 25 is a schematic diagram illustrating an example waveform of a redspot-dynamic response function.

Then, when the calculated correlation value r is greater than or equal to a predetermined value, the determination component extraction unit 444 sets the component corresponding to the correlation value r as a component related to the brain function activation information. Then, the determination component extraction unit 444 extracts the determination component on the basis of the value of the significance level. That is, the determination component extraction unit 444 extracts a component having a low significance level as the determination component. The extracted determination component and the calculated correlation value r are delivered to the storage unit 430 or the mental illness determination unit 445. As the "determination waveform" described above, a modified wave that takes the human physiological response into account is used. The determination waveform is displaced after a predetermined time elapses after the provision of the emotional stimulation information. Specifically, a rectangular wave may be employed as the determination waveform. Alternatively, a waveform, which is a convolution of a rectangular wave with a redspot-dynamic response function, can also be employed as the determination waveform. The redspot-dynamic response function is generated from the average value or the like of a plurality of components determined by calculating a component found to have a correlation with brain function activation information is provided for a moment among the plurality of components 1, 2, 3, . . . obtained through decomposition by the face change information decomposition unit 443 and by performing the same calculation a plurality of times. At this time, amplitude (height direction) is in arbitrary unit, and no absolute value can be given. A signal obtained at rest is used as a baseline value, and this value is used as a reference to determine the height of the waveform. Then, the average value of superimposed pieces of data, which are obtained from a plurality of test subjects, is calculated to generate a redspot-dynamic response function. The initial value of the redspot-dynamic response function has a waveform illustrated in FIG. 25 when the emotional stimulation information is provided for a moment. When the emotional stimulation information is provided for a certain period of time, a redspot-dynamic response function is generated from a convolution with a rectangular wave. The redspot-dynamic response function has waveform in which, as the amount of displacement increases, a peak value extends along the horizontal axis from the peak time point. The redspot-dynamic response function further has a waveform whose phase is delayed at the time point at which the provision of the brain function activation information (stimulation) is finished, with the displacement decreasing. The redspot-dynamic response function, when found to have a significant correlation with a component obtained from the face change information, has a shape close to the correlation waveform and thus has a higher correlation value than a rectangular wave or the like. This can enhance the accuracy of the extraction of the determination component.

The mental illness determination unit 445 calculates a difference $\Delta r$ between the reference correlation value r1 for the reference determination component extracted in response to the provision of the negative image or the like and the correlation value r2 for the determination component extracted in response to the provision of the positive image or the like. Then, the mental illness determination unit 450 determines a "state level" corresponding to the difference $\Delta r$ between the reference correlation value r1 and the correlation value r2 on the basis of the determination information stored in the determination information database 432. The determined state level is output to the display device or the like via the output unit 420.

(7-2) Operation of Mental Illness Determination Device

Figure 26A:
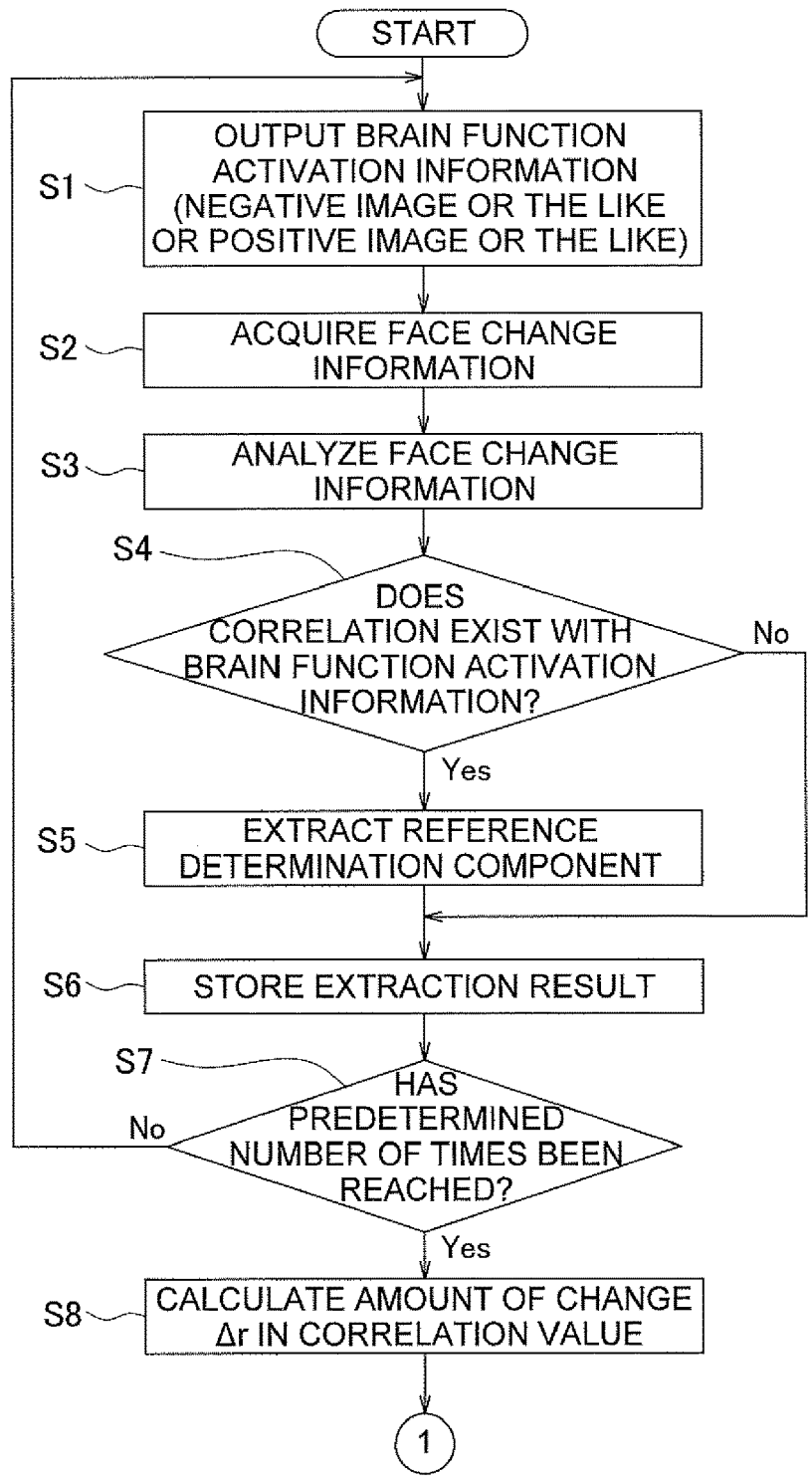
FIG. 26A is a flowchart illustrating the operation of the mental illness determination device.
Figure 26B:
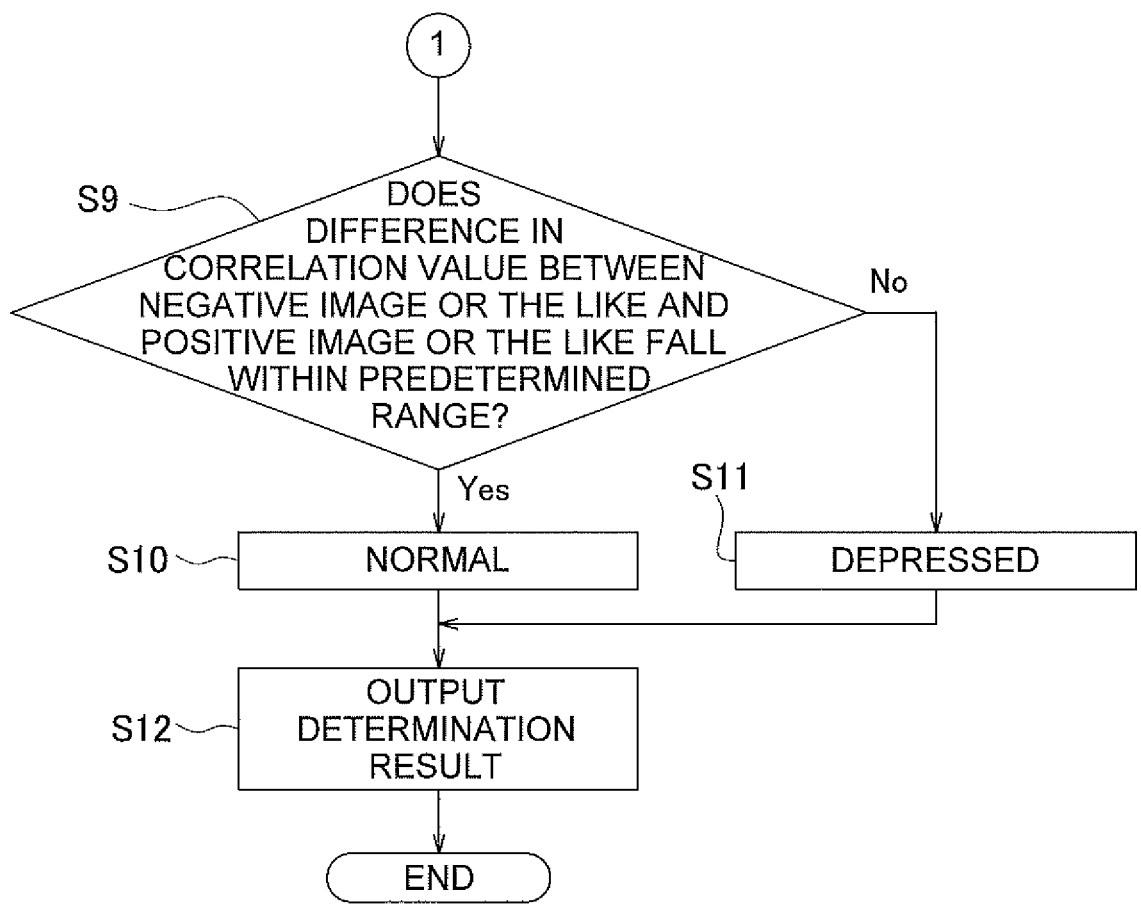
FIG. 26B is a flowchart illustrating the operation of the mental illness determination device.

FIG. 26 is a flowchart illustrating the operation of the mental illness determination device 400. In the following description, a description will be given of the determination of the state of "depression" as the state of mental illness, by way of example.

First, an instruction is input to the mental illness determination device 400 via the input unit 410 or the like to start measurement. At this time, the name and/or the test subject number or the like of the subject 300, who is the test subject, is input. Then, a guide screen is displayed on the output unit 420 to guide the subject 300 so as to position the face of the subject 300 at the center of the guide screen.

Figure 27:
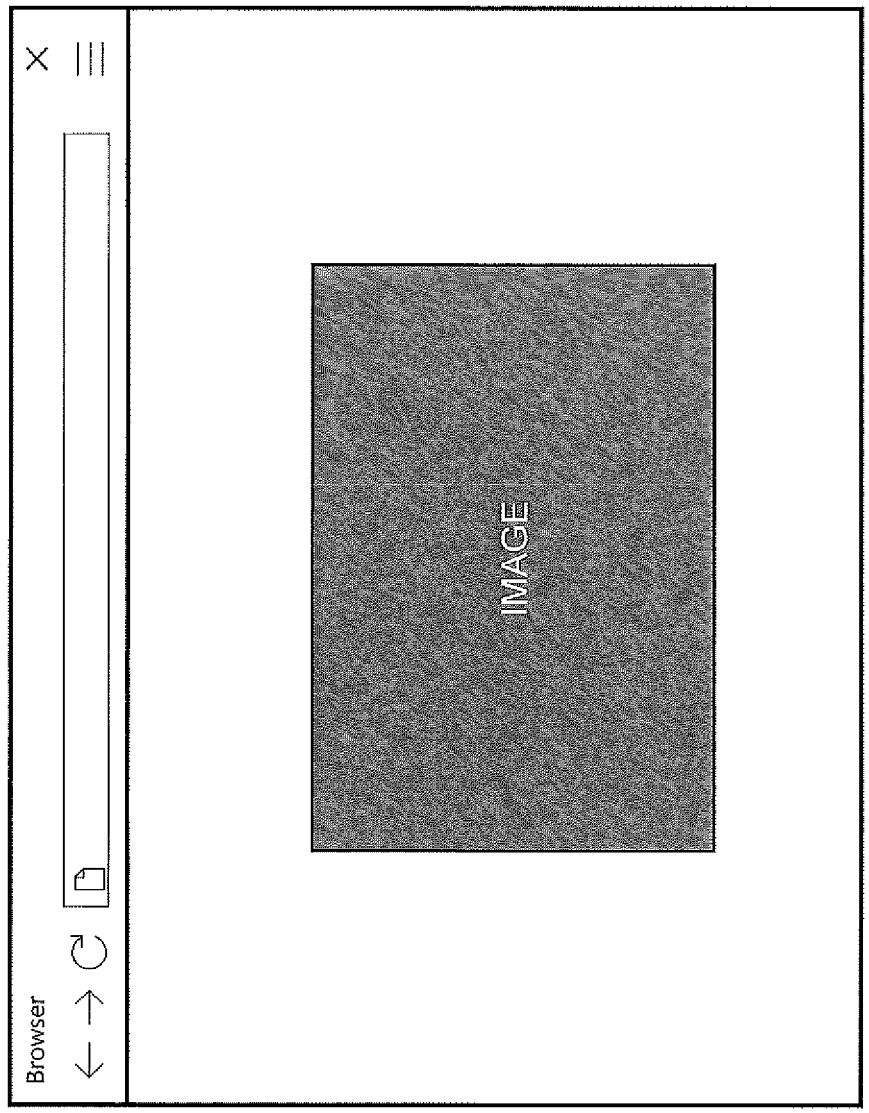
FIG. 27 is a schematic diagram illustrating an example screen displaying an image, which is output from the mental illness determination device.

Then, an instruction is input to the mental illness determination device 400 to output the brain function activation information. Accordingly, the brain function activation information is read from the brain function activation information database 431, and the brain function activation information is output to a display screen as illustrated in FIG. 27 via the output unit 420 (S1). Here, deactivation information (the rest image or the like), the negative image or the like, and the positive image or the like are sequentially output to the output unit 420 as the brain function activation information. The rest image is a blank image, a cross-mark image, or an intermediate image.

Figure 28:
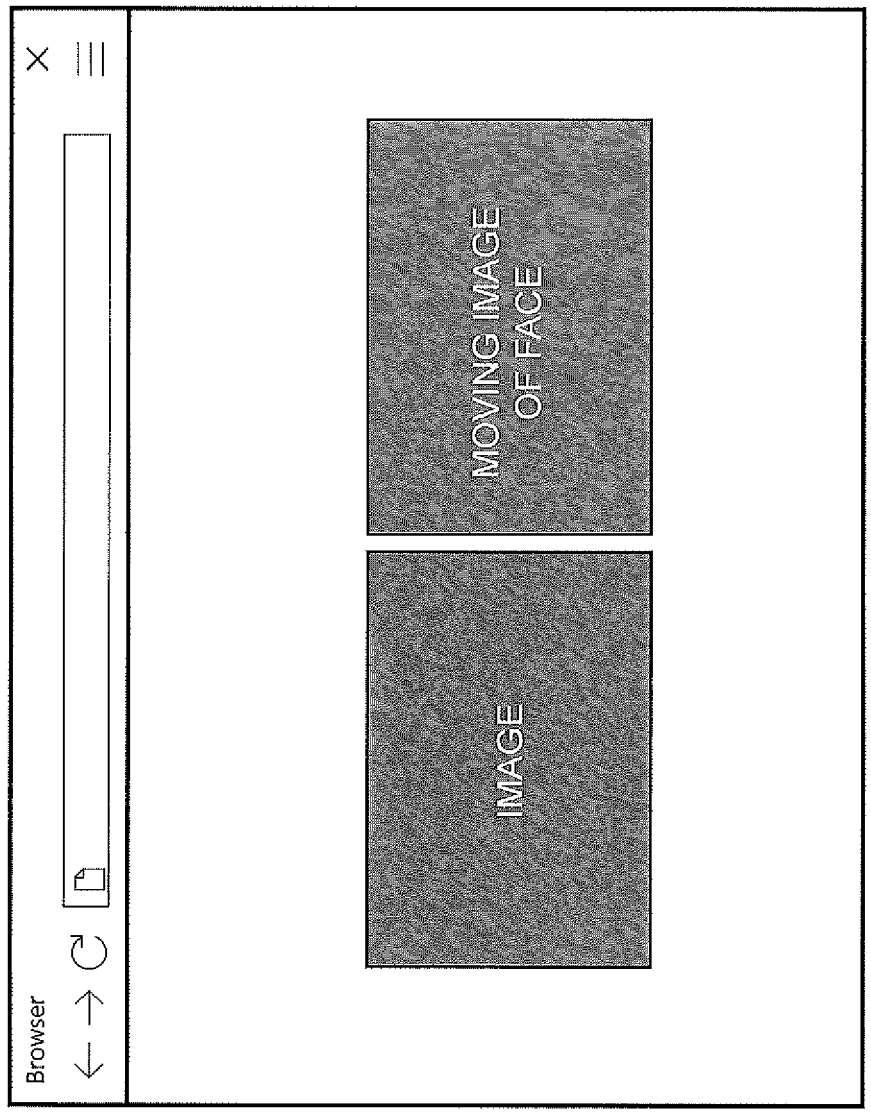
FIG. 28 is a schematic diagram illustrating an example screen displaying captured images, which is output from the mental illness determination device.

Then, face images of the subject 300, who is located in front of the output unit 420, are captured by the image capturing unit 415 at predetermined intervals at the same time as the output of the brain function activation information or at a predetermined timing (S2). The captured face images are delivered to the face change information acquisition unit 442. Then, when a predetermined time elapses, the display of the image is finished, and, at the same time, the capturing of a moving image of the face is also finished. At this time, as illustrated in FIG. 28, the acquired face images and the currently displayed emotional image or the like can also be displayed to check the content of both images.

Subsequently, in the mental illness determination device 400, the captured face image is analyzed. Specifically, the face change information acquisition unit 442 acquires, from the captured face image, face change information indicating a time-series change in the face data of the subject 300. Then, the face change information decomposition unit 443 performs the singular value decomposition, the principal component analysis, or the independent component analysis to decompose the face change information into a plurality of components 1, 2, 3, . . . (S3).

Then, the determination component extraction unit 444 calculates a correlation value between each of the plurality of components 1, 2, 3, . . . obtained through decomposition by the face change information decomposition unit 443 and the determination waveform corresponding to the brain function activation information. Then, the determination component extraction unit 444 determines whether the correlation value is greater than or equal to a predetermined value (S4). If the correlation value is determined to be greater than or equal to the predetermined value, "existence of a correlation" is determined between the brain function activation information and the component (S4—Yes). Then, the determination component extraction unit 44 extracts a component having a correlation with the brain function activation information and having a low significance level as a "determination component" (S5). Further, the determination component extraction unit 444 stores the correlation value between the brain function activation information and the determination component in the storage unit 430 separately for the type of the positive image or the like and the type of the negative image or the like (S6). On the other hand, if the correlation value between the brain function activation information and each of the components 1, 2, 3, . . . is less than the predetermined value, "non-existence of a correlation" is determined, and information indicating non-existence of a correlation is stored in the storage unit 430 (S4—No, S6).

Thereafter, steps S1 to S6 described above are executed a predetermined number of times (S7). Then, the mental illness determination unit 445 calculates the amount of change Δr, which is the difference between the reference correlation value r1 for the reference determination component extracted in response to the provision of the negative image or the like and the correlation value r2 for the determination component extracted in response to the provision of the positive image or the like (S8).

Figure 29:
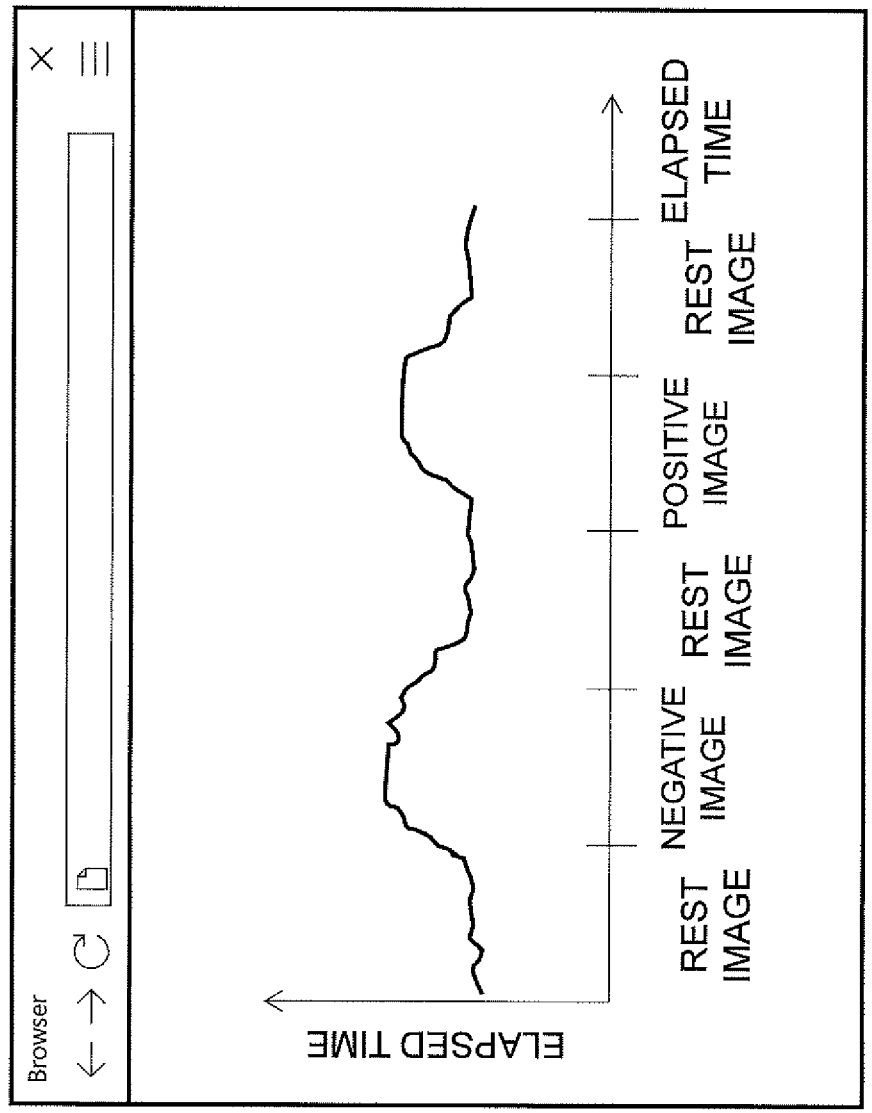
FIG. 29 is a schematic diagram illustrating an example screen displaying an analysis waveform, which is output from the mental illness determination device.
Figure 30:
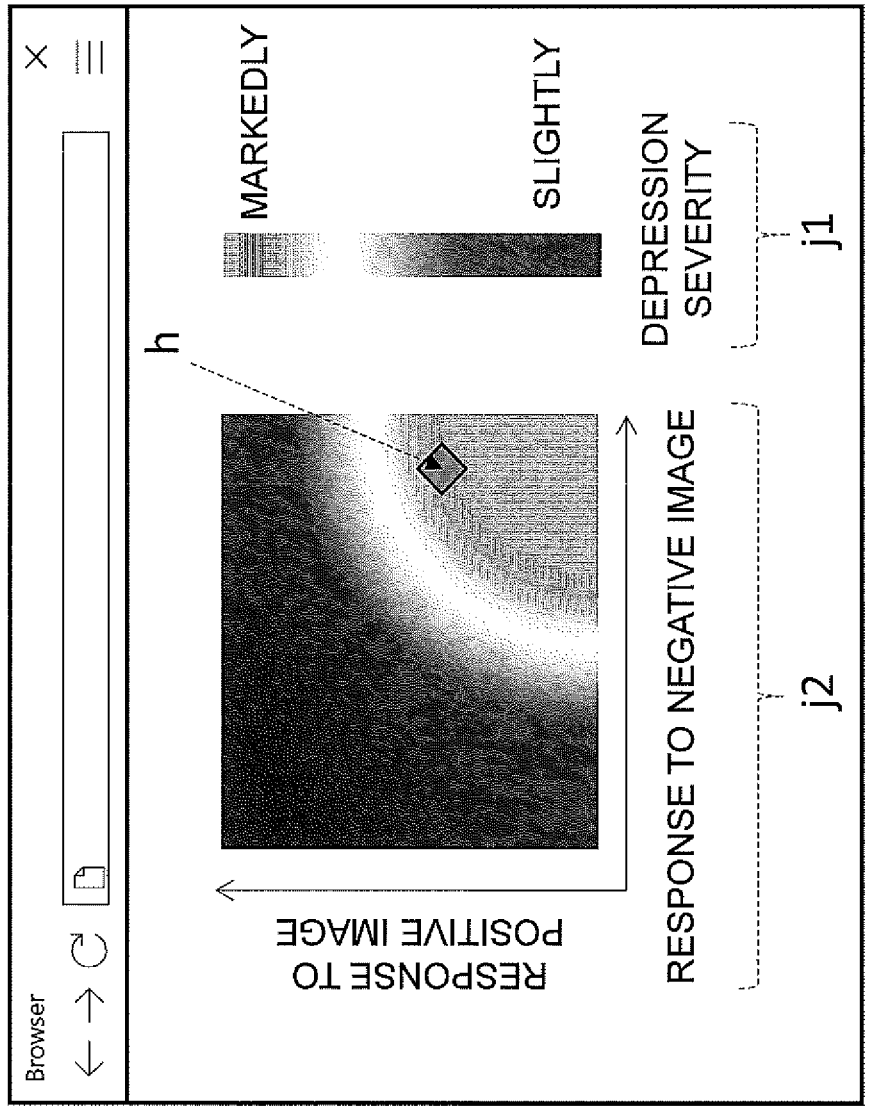
FIG. 30 is a schematic diagram illustrating an example screen displaying a distribution diagram, which is output from the mental illness determination device.

Subsequently, the mental illness determination unit 450 determines whether the amount of change Δr of the correlation value r2 with respect to the reference correlation value r1 falls within a predetermined range (S9). The determination of whether the amount of change Δr falls within the predetermined range is performed by matching against the determination information stored in the determination information database 432. If the amount of change Δr of the correlation value r2 with respect to the reference correlation value r1 falls within the predetermined range, the mental illness determination unit 445 determines that the subject 300 is "normal" (S9—Yes, S10). On the other hand, if the amount of change Δr of the correlation value r2 with respect to the reference correlation value r1 does not fall within the predetermined range, the mental illness determination unit 445 determines that the subject 300 is "depressed" (S9—No, S11). For example, if the amount of change Δr falls within the range of Δra to Δrb described above, the subject 300 is determined to be normal. If the amount of change Δr exceeds Δrb, the subject 300 is determined to be depressed. The determination result is output to the display device or the like via the output unit 420 (S12) as a determination result. At this time, the output unit 420 may display an analysis waveform as illustrated in FIG. 29. Alternatively, a distribution diagram as illustrated in FIG. 30 may be displayed. The color scale or gray scale (j1) on the right side of FIG. 30 represents the state level (here, the depression level). The two-dimensional distribution (j2) on the left side of FIG. 30 indicates the degree of response to the negative image or the like on the horizontal axis, and the degree of response to the positive image or the like on the vertical axis, with a plotted point h indicating the state of the test subject.

Thereafter, the mental illness determination device 400 saves the data in accordance with an input instruction from the device user. Specifically, the mental illness determination device 400 stores, for each test subject, the data of the determination result, the analysis waveform, the measurement result, the image display conditions, and so on in the storage unit in association with each other.

(7-3) Features of Mental Illness Determination Device (7-3-1)

As described above, the mental illness determination device 400 according to this embodiment includes the brain function activation information providing unit (emotional stimulation information providing unit) 441, the face change information acquisition unit 442, the face change information decomposition unit 443, the determination component extraction unit 444, and the mental illness determination unit 445. The brain function activation information providing unit 441 provides "brain function activation information" for activating the human brain function to the subject 300. For example, "emotional stimulation information" is provided as the brain function activation information. The face change information acquisition unit 442 acquires "face change information" indicating a time-series change in face data of the subject 300. The face change information decomposition unit 443 decomposes the face change information into a plurality of components 1, 2, 3, . . . by using singular value decomposition, principal component analysis, or independent component analysis. The determination component extraction unit 444 extracts a component related to the brain function activation information from the plurality of components 1, 2, 3, . . . as a "determination component". The mental illness determination unit 445 determines a state of mental illness of the subject 300 on the basis of the determination component.

Accordingly, the mental illness determination device 400 according to this embodiment extracts a determination component related to the brain function activation information from a plurality of components 1, 2, 3, . . . obtained by subjecting the face change information to the singular value decomposition, the principal component analysis, or the independent component analysis. This facilitates the estimation of the presence of brain activity of the subject 300 without using electrodes or the like that require preprocessing before attachment. Thus, a state of mental illness of the subject 300 can be easily determined on the basis of the determination component corresponding to the brain function of the subject 300.

Figure 31:
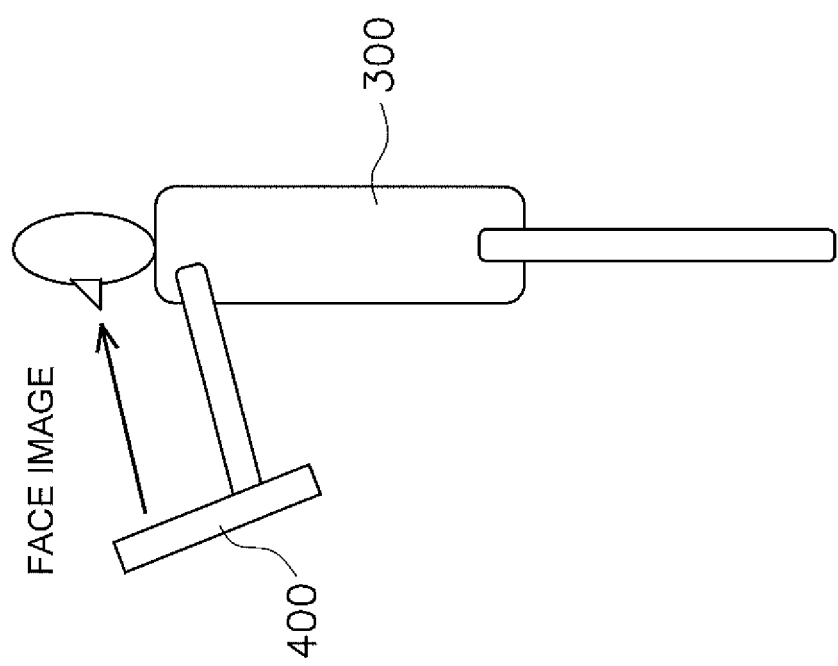
FIG. 31 is a schematic diagram illustrating a specific exemplary embodiment of the mental illness determination device.
Figure 32:
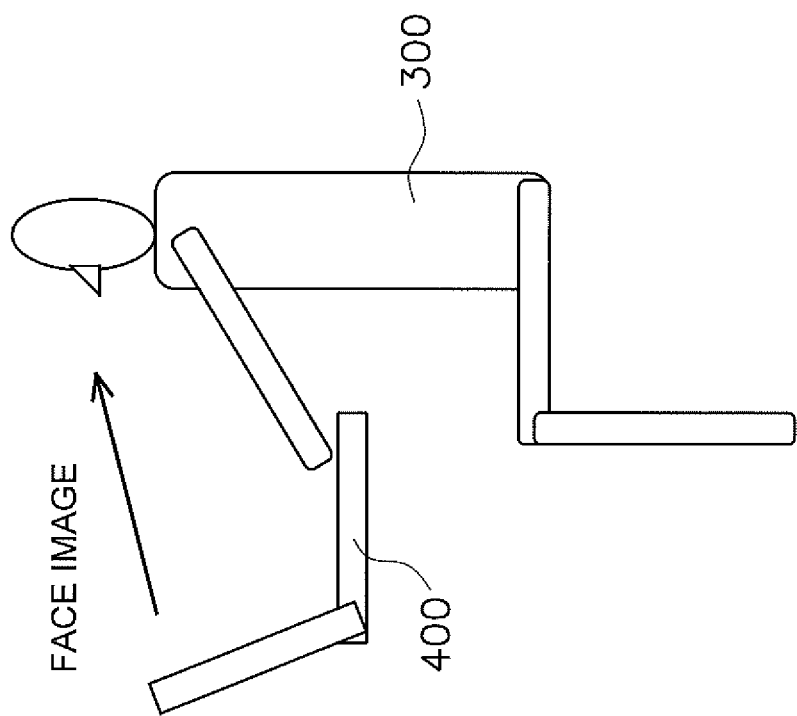
FIG. 32 is a schematic diagram illustrating a specific exemplary embodiment of the mental illness determination device.

As illustrated in FIG. 31, the mental illness determination device 400 according to this embodiment can be incorporated in a smart device. Alternatively, as illustrated in FIG. 32, the mental illness determination device 400 can be incorporated in a notebook PC. These configurations facilitate mental illness determination at any location.

In the foregoing description, the description has been given of the determination of the state of "depression" as the state of mental illness, by way of example. However, the mental illness determination device 400 is capable of determining any mental illness that can be determined with the configuration described above. For example, the mental illness determination device 400 is capable of determining the state of any disorder or the states of any combination of disorders among mood disorders, anxiety disorders, substance-related disorders, dementia, and autism on the basis of the determination component. In particular, the mental illness determination unit 445 is capable of determining, as the state of one of the mood disorders described above, the state of any disorder or any combination of disorders among depression, schizophrenia, and bipolar disorder. When the state of depression is to be determined, the response to the positive image or the like and the response to the negative image or the like are mainly compared with each other. When the state of any other mental illness is to be determined, the corresponding process is executed.

In the mental illness determination device 400 according to this embodiment, the brain function activation information providing unit 441 may provide, instead of an emotional image, "emotional stimulation information" for stimulating any sense or any combination of senses among the auditory sense, the olfactory sense, the gustatory sense, the tactile sense, and the somatic sensation of the subject 300 to change emotion. That is, the emotional stimulation information may stimulate any other sense, instead of stimulating the visual sense. Specifically, a positive sound for relaxing and a negative sound for discomfort may be used. Even with these pieces of information, results similar to those obtained when an emotional image is presented can also be obtained.

In the mental illness determination device 400 according to this embodiment, furthermore, the brain function activation information providing unit 441 may be configured to present an emotional image in addition to providing emotional stimulation information for stimulating any sense or any combination of senses among the auditory sense, the olfactory sense, the gustatory sense, the tactile sense, and the somatic sensation of the subject 300. This configuration enables the stimulation of different brain regions and enables the determination of various types of mental illnesses. For example, using information for stimulating the visual sense, diseases related to the occipital region of the brain can be diagnosed. Using information for stimulating the auditory sense, diseases related to the temporal region and the frontal region of the brain can be diagnosed. Moreover, using information on a face image, dementia and autism can be diagnosed. Using voice audio information, anxiety disorders can be diagnosed.

(7-3-2)

In the mental illness determination device 400 according to this embodiment, furthermore, the face change information acquisition unit 442 acquires, as face data, data of the paranasal-sinus surrounding area and/or the forehead portion of the subject 300. Thus, a determination component related to brain activity can be extracted accurately. The brain has a mechanism for cooling the brain while leaving the body temperature unchanged, called a selective brain cooling system. The selective brain cooling system dissipates heat generated by brain activity through an area around the paranasal sinuses and the forehead portion. By analyzing data of these parts, a component related to brain activity can be extracted accurately. As a result, the mental illness determination device 400 according to this embodiment can execute high-accuracy mental illness determination.

(7-3-3)

In the mental illness determination device 400 according to this embodiment, furthermore, the face change information acquisition unit 442 acquires, as face data, facial skin temperature data indicating the facial skin temperature of the subject 300. In other words, the mental illness determination device 400 can determine a state of mental illness by using an infrared camera or the like.

(7-3-4)

In the mental illness determination device 400 according to this embodiment, furthermore, the face change information acquisition unit 442 acquires, as face data, facial blood-circulation-amount data based on face RGB data of the subject 300. That is, the mental illness determination device 400 can determine a state of mental illness by using a solid-state imaging device (CCD, CMOS). This enables mental illness determination with a simple configuration.

(7-3-5)

In the mental illness determination device 400 according to this embodiment, furthermore, the determination component extraction unit 444 extracts a determination component on the basis of the value of the significance level. In the mental illness determination device 400, a determination component related to the brain function activation information is extracted on the basis of the value of the significance level. This enables an increase in the reliability of mental illness determination.

(7-3-6)

In the mental illness determination device 400 according to this embodiment, furthermore, the brain function activation information providing unit 441 provides, as brain function activation information, an emotional image classified as a negative image or the like or a positive image or the like. Thus, a determination component related to brain activity can be extracted. As a result, the state of mental illness of a subject can be easily determined.

(7-3-7)

Further, the mental illness determination device 400 according to this embodiment includes the determination information database 432 that stores, as "determination information", in association with the state level, an amount of change $\Delta r$ of the correlation value r2 of the determination component calculated in response to the provision of the positive image or the like with respect to the reference correlation value r1 of the reference determination component calculated in response to the provision of the negative image or the like, the amount of change $\Delta r$ falling within a predetermined range. Then, the mental illness determination unit 445 calculates the correlation value r2 of the determination component in response to the provision of the positive image or the like, and determines the state level of the subject 300 on the basis of the calculated correlation value r2 and the determination information.

With this configuration, the mental illness determination device 400 facilitates the determination of the state level of mental illness by using the determination component extracted in response to the provision of the positive image or the like. In summary, the mental illness determination device 400 can not only determine the presence of mental illness but also determine and output the state level of mental illness.

(7-3-8)

A determination method according to this embodiment for determining a state of mental illness does not necessarily require the mental illness determination device 400. That is, a mental illness determination method according to this embodiment may include, regardless of the use of the mental illness determination device 400, a brain function activation information providing step of providing, as brain function activation information for activating the human brain function, emotional stimulation information classified as the positive image or the like to the subject 300, a face change information acquisition step of acquiring "face change information" indicating a time-series change in face data of the subject 300 after the provision of the positive image or the like, a face change information decomposition step of decomposing the face change information into a plurality of components by using singular value decomposition, principal component analysis, or independent component analysis, a determination component extraction step of extracting a component related to the brain function activation information from the plurality of components as a determination component, and a determination step of determining a state of mental illness of the subject 300 on the basis of the determination component.

In this determination method, after the provision of emotional stimulation, the face change information is subjected to the singular value decomposition, the principal component analysis, or the independent component analysis to obtain a plurality of components, from which a determination component related to the brain function activation information is extracted to determine a state of mental illness. This facilitates the determination of a state of mental illness of the subject 300.

(7-3-9)

In the mental illness determination device 400 described above, the reference correlation value r1 is set in response to the provision of the negative image or the like. Alternatively, the reference correlation value may be set in response to the provision of the positive image or the like. In this case, the determination information database 432 stores, as "determination information" in advance, in association with the "state level", an amount of change $\Delta r$ (=r4−r3) of a correlation value r4 of a determination component extracted in response to the provision of the negative image or the like with respect to a "reference correlation value" r3 of a reference determination component extracted in response to the provision of the positive image or the like, the amount of change $\Delta r$ falling within a predetermined range. Further, the mental illness determination unit 445 calculates a difference $\Delta r$ between the reference correlation value r3 calculated in response to the provision of the positive image or the like and the correlation value r4 calculated in response to the provision of the negative image or the like. Then, the mental illness determination unit 445 determines the state level of mental illness corresponding to the difference $\Delta r$ between the reference correlation value r3 and the correlation value r4 on the basis of the determination information stored in the determination information database 432.

(7-3-10)

As described above, the mental illness determination device 400 may, instead of determining a state of mental illness by using an amount of change falling within a predetermined range of a correlation value for a determination component with respect to a reference value, determine a state of mental illness on the basis of any one or any combination of the following: a value obtained by performing multiple regression analysis on a determination component, the area of a region for which the determination waveform is generated, the average value of the determination waveform, and the value for the center of gravity of the determination waveform. Note that the use of the "multiple regression analysis" facilitates quantification of a correlation value of the response to a plurality of stimuli. The use of the "correlation value" facilitates quantification of a correlation value of the response to a single stimulus. The use of the "area" facilitates quantification of the absolute value of response. The use of the "average value" facilitates quantification of the absolute value of response. In addition, noise can be reduced compared to the use of the area. The use of the "value for the center of gravity" facilitates quantification of the absolute value of response. In addition, the timing at which a response occurred can be easily determined compared to the use of the area.

(7-3-11)

In the mental illness determination device 400 according to this embodiment, furthermore, the determination component extraction unit 444 extracts the determination component on the basis of a correlation value between a determination waveform corresponding to the emotional stimulation information and each of the plurality of components. This configuration can specify the determination component corresponding to the brain function of the subject.

Here, a modified wave that takes the human physiological response into account may be employed as the determination waveform. The determination waveform is displaced after a predetermined time elapses after the provision of the emotional stimulation information. The determination waveform, when found to have a significant correlation with a component obtained from the face change information, shows a high correlation value, and thus the accuracy of the extraction of the determination component can be enhanced. In addition, a slight delay of the phase with respect to the response of the brain provides accurate correlation. Specifically, a redspot-dynamic response function may be employed as the determination waveform. The redspot-dynamic response function is generated from a plurality of components determined by calculating a component found to have a correlation with brain activation information is provided for a moment among the plurality of components 1, 2, 3, . . . obtained through decomposition by the face change information decomposition unit 443 and by performing the same calculation a plurality of times. The redspot-dynamic response function is optimized using previous history, and, thus, shows a high correlation value when the redspot-dynamic response function is found to have a significant correlation with a component obtained from the face change information. This can enhance the accuracy of the extraction of the determination component.

Alternatively, a rectangular wave may be employed as the determination waveform. A rectangular wave can be adjusted depending on whether emotional stimulation information is being provided, and thus the determination component can be easily extracted.

(7-4) Modification of Mental Illness Determination Device (7-4-1)

Figure 33:
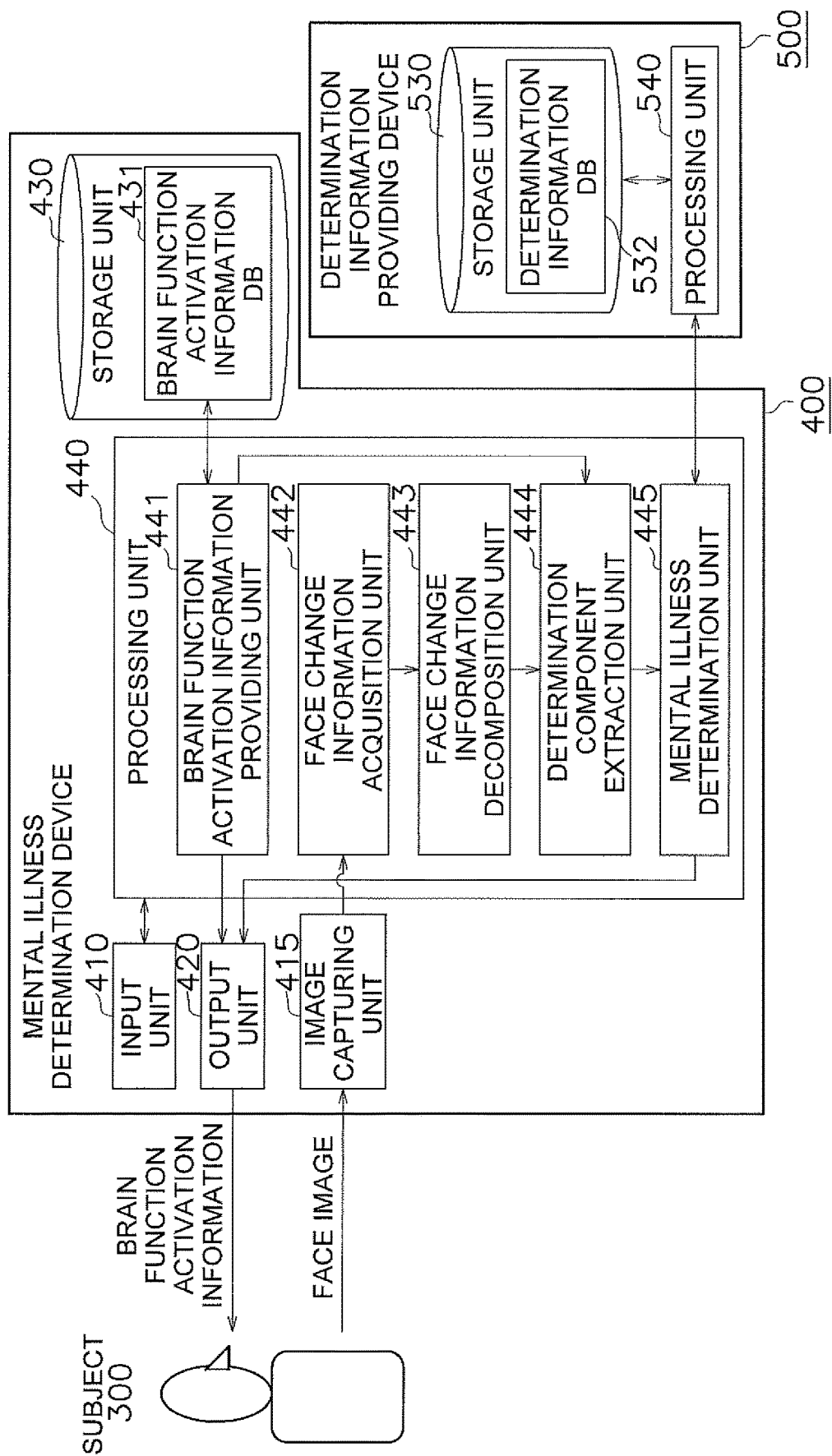
FIG. 33 is a schematic diagram illustrating a configuration of a modification of the mental illness determination device.

As illustrated in FIG. 33, the mental illness determination device 400 according to this embodiment may utilize a determination information providing device 500 or the like located on a network.

The determination information providing device 500 includes a storage unit 530 and a processing unit 540.

The storage unit 530 has a determination information database 532. The determination information database 532 has a configuration similar to that of the determination information database 432 described above. That is, the determination information database 532 stores, as determination information, in association with the state level of mental illness, an amount of change Δr of the correlation value r2 of the determination component calculated in response to the provision of the positive image or the like with respect to the reference correlation value r1 of the reference determination component calculated in response to the provision of the negative image or the like, the amount of change Δr falling within a predetermined range.

The processing unit 540 transmits the determination information stored in the determination information database 532 in response to a request from the mental illness determination device 400. The processing unit 540 may have a function of generating determination information as big data on the basis of predetermined information, independently of the determination component extracted by the mental illness determination device 400. When the mental illness determination device 400 calculates the reference correlation value r1, the processing unit 540 executes a process for updating the reference correlation value r1 stored in the determination information database 432, if necessary.

In this modification, the mental illness determination unit 445 requests the determination information providing device 500 described above to provide determination information. More specifically, in the mental illness determination device 400 according to this modification, the determination information database 532 is stored in the determination information providing device 500 on the network, and the mental illness determination unit 445 accesses the determination information providing device 500 when determining the state level of mental illness. Then, the mental illness determination unit 445 determines the state level of mental illness of the subject 300 on the basis of the calculated correlation value r2 and the determination information.

Accordingly, in the mental illness determination device 400 of this modification, the mental illness determination unit 445 can determine the state level of mental illness of the subject 300 by using the determination information providing device 500 on the network.

In addition, the mental illness determination unit 445 determines a state of mental illness by using the reference determination component stored in the determination information providing device 500 on an external network. The provision of the negative image or the like may thus be omitted. That is, as illustrated in FIG. 34, a configuration can be employed in which only the positive image or the like is provided as the brain function activation information.

Figure 34:
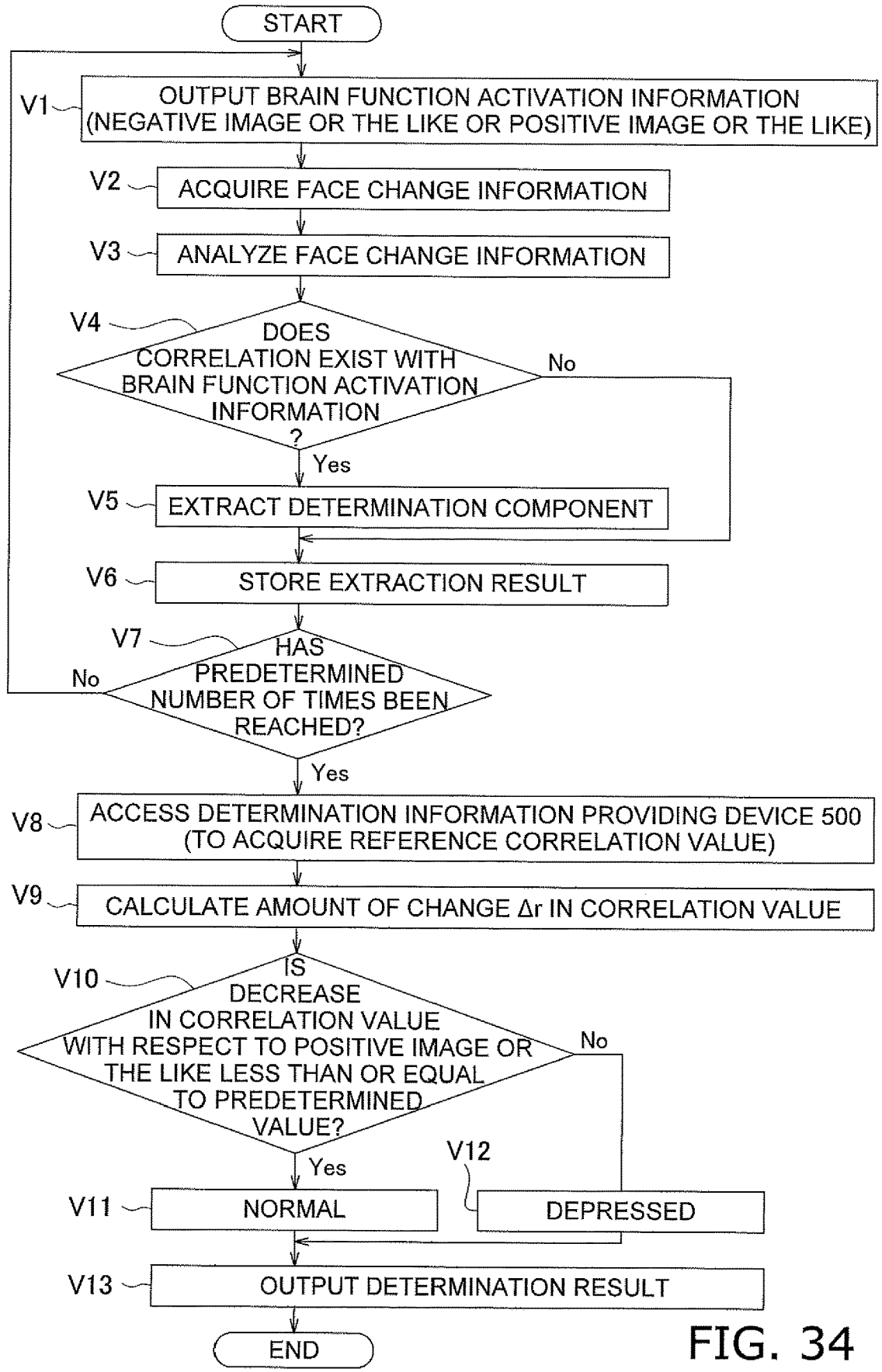
FIG. 34 is a flowchart illustrating the operation of the modification of the mental illness determination device.

FIG. 34 is a flowchart for describing a determination method for determining a state of mental illness according to this modification. In this modification, only the positive image or the like is provided to the subject 300 as brain function activation information (V1). In steps V2 to V7, processing similar to that in steps S2 to S7 described above is performed. Accordingly, the mental illness determination device 400 calculates the correlation value r2 calculated in response to the provision of the positive image or the like. Then, in step V8, the mental illness determination device 400 requests the determination information providing device 500 to transmit determination information. Accordingly, the mental illness determination device 400 acquires the reference correlation value r1 calculated in response to the provision of the negative image or the like. Subsequently, the mental illness determination unit 445 determines whether the amount of change Δr of the correlation value r2 with respect to the reference correlation value r1 falls within a predetermined range (V9 to 12). Then, the determination result is output to the display device or the like via the output unit 420 (S13). Accordingly, the state of mental illness is determined by using the reference determination component stored in the determination information providing device 500 on the external network.

Some of the steps described above may be executed without using the mental illness determination device 400.

In the mental illness determination method of this modification, furthermore, the determination of a state of mental illness using big data can be implemented. That is, the reference correlation value r1 and the predetermined amount of change Δr are determined from big data. Specifically, the negative image or the like is provided to a person other than the subject 300 to extract a reference determination component, and the reference correlation value r1, which is calculated on the basis of this reference determination component, is used. This can optimize the determination information, if necessary.

In the modification described above, a method has been described for providing only the positive image or the like to determine a state of mental illness. However, a method is also feasible for providing only the negative image or the like to determine a state of mental illness. That is, when a correlation value for the negative image or the like shows a higher value than a reference correlation value stored in a determination information providing device on a network, the state of depression or the like may be determined.

(7-4-2)

The mental illness determination device 400 according to this embodiment may further include an autonomic nervous activity measurement unit that measures the autonomic nervous activity of the subject. The mental illness determination unit 445 determines the type of mental illness on the basis of the autonomic nervous activity. This configuration can determine the ratio of a response to emotional stimulation, which is derived from the autonomic nervous system, to a response to emotional stimulation, which is derived from brain activity, and thus determine various types of diseases. The types of diseases that can be determined include, for example, "depressive disorder/major depressive disorder, dysthymic disorder, depressive disorder not otherwise specified, depression-related syndrome", "bipolar disorder/bipolar I disorder, bipolar II disorder", "schizophrenia", "developmental disability/pervasive developmental disorders (autism, Asperger's syndrome, Tourette syndrome), learning disability LD, attention deficit hyperactivity disorder ADHD", "mental retardation", "anxiety disorder/generalized anxiety disorder, panic disorder, social anxiety disorder, obsessive-compulsive disorder, dissociative disorder, adjustment disorder", "dementia/Alzheimer-type dementia, vascular dementia, dementia with Lewy bodies, frontotemporal dementia", "substance use disorder", "organic mental illness, including the symptomatic ones", "epilepsy", and "personality disorder".

(7-4-3)

The mental illness determination device 400 according to this embodiment may further include a line-of-sight measurement unit that measures the line of sight of the subject 300. The mental illness determination unit 445 removes a low-reliability determination result on the basis of the line of sight of the subject 300. This configuration can determine whether the subject 300 is recognizing image information. Thus, a low-reliability determination result can be removed.

(7-5) Test for Verifying Mental Illness Determination Device (7-5-1)

A test for verifying a mental illness determination device according to this embodiment was performed in the following conditions. Here, the determination of the state of "depression" was verified as the state of mental illness.

In this test, 25 photographs of negative images and 25 photographs of positive images were used, and each photograph was presented for 4.8 seconds. Each photograph was shown in such a manner as to be displayed on a large TV screen, from which a test subject was seated 1 meter away. For measurement, RGB image data was acquired by using a camera having a face tracking function. The measurement was performed such that the test subject initially rested for 2 minutes, was presented with an emotional image for another 2 minutes, and rested for another 2 minutes.

Figure 35A:
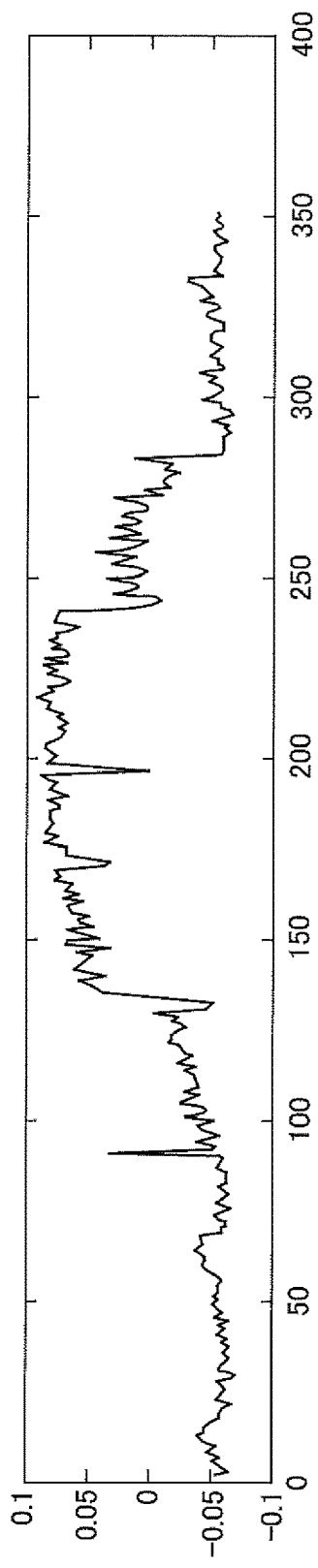
FIGS. 35A and 35B are diagrams illustrating the waveform of a determination component when a positive image is presented.
Figure 35B:
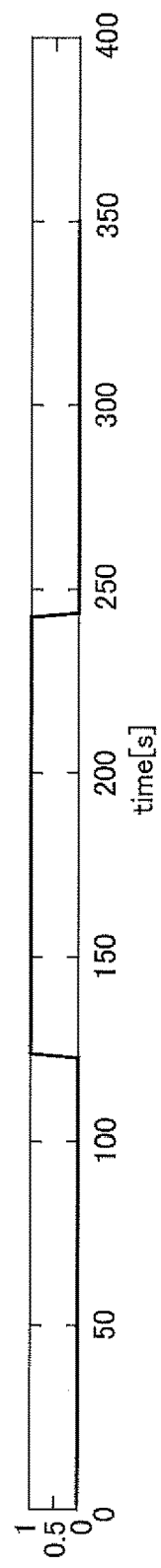

FIGS. 35A and 35B illustrate the waveform of a determination component when the positive image is presented to a certain subject, and FIGS. 36A and 36B illustrate the waveform of a determination component when the negative image is presented to the subject. In the example in FIGS. 35A and 35B and 36A and 36B, FIGS. 35A and 36A each illustrate the waveform of the determination component, and FIGS. 35B and 36B each illustrate the timing during which the positive image or the negative image is presented. Here, the determination component had a correlation value of 0.86 in response to the provision of the positive image. However, the determination component also showed a correlation value of 0.86 in response to the provision of the negative image. This indicates that not only the provision of the positive image but also the provision of the negative image has a correlation with the determination component. This subject scored 3 for depression in the CES-D depression scale and was thus a person with a "slight tendency for depression" although the score was within a normal range.

This indicates that the provision of an emotional image enables the estimation of activation of the brain function, which can be utilized to determine the physiological state, in particular, the state of "depression".

(7-5-2)

Further, a test for verifying the mental illness determination device 400 according to this embodiment was performed in the following conditions. Here, the determination of the state of "depression" as the state of mental illness was verified.

In this test, face images were acquired from eight test subjects. Specifically, the test subjects were seated in chairs having a headrest placed in laboratory, and captured image data of an area around the nose portion of the entire area of the face of each of the test subjects was acquired in time series by using an RGB camera of a notebook PC.

In this test, as the notebook PC, an imaging device installed on the liquid crystal display screen side of MacBook Air (registered trademark), manufactured by Apple Inc., was used, and time-series face images were acquired as color moving image data. The notebook PC was placed in front of the test subject at a distance of 0.5 m from the test subject. Then, the imaging device continuously captured image data for 130 seconds along the time axis in periods of 10 frames per second to obtain moving image data of the face.

In this test, furthermore, the test subjects were presented with brain function activation information during the acquisition of the face images. Examples of the brain function activation information include information for causing each test subject to recognize an image or a moving image and a schematic diagram or perform any other operation on the basis of the video displayed on the display device or the like, information for causing each test subject to perform psychological tasks such as memorizing symbols, characters, or words, information for stimulating the auditory sense of each test subject to understand a word, recognize music or ambient sound or perform any other operation, information for stimulating the olfactory sense of each test subject to recognize an odor or aroma or perform any other operation, and information for stimulating the somatic sensation of each test subject to recognize the sense of pain or touch or perform any other operation. In this test, the "positive image and negative image" were employed as the brain function activation information. In addition, as a precondition, each test subject was assigned a task of gazing at continuous images on the display device.

Figure 37:
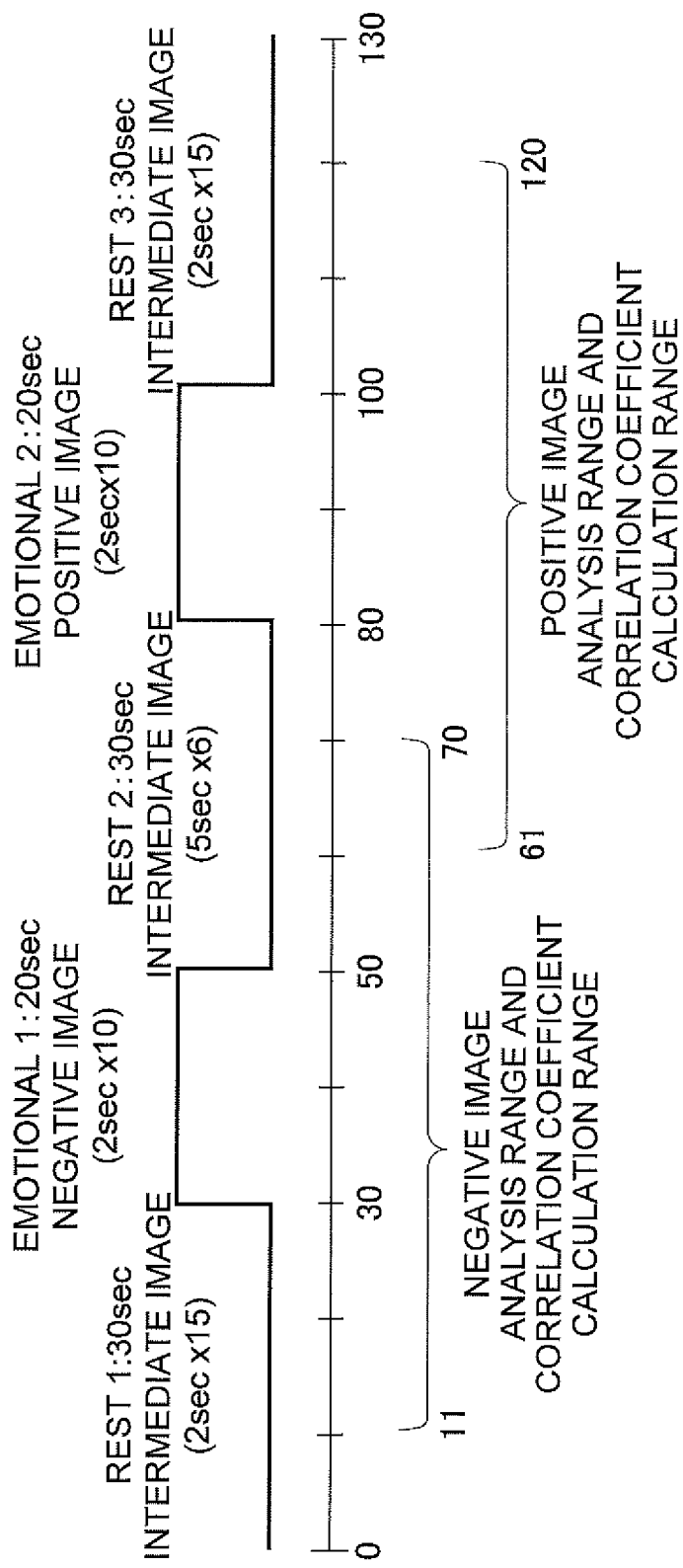
FIG. 37 is a diagram for describing an overview of a test performed by the mental illness determination device.

In this test, as illustrated in FIG. 37, each test subject was presented with brain function activation information (emotional image information) such that the "rest image" was presented for 30 seconds after the start of face image acquisition ("rest 1"), the "negative image" was presented for another 20 seconds ("emotion 1"), the "rest image" was presented for another 30 seconds ("rest 2"), the "positive image" was presented for another 20 seconds ("emotion 2"), and the "rest image" was presented a period of another 30 seconds ("rest 3").

In analysis of the face images, blood-circulation-amount data was calculated on the basis of RGB data obtained from the captured moving image data of the faces, and the singular value decomposition was performed by using SVD of MATLAB (registered trademark) (Singular Value Decomposition) as an analysis tool. Here, an erythema index "a*" having a correlation with redness of the skin or the amount of hemoglobin, which was computed from RGB data of an image, was determined in accordance with the CIE-L*a*b* color system, and was defined as blood-circulation-amount data. The singular value decomposition was performed on the blood-circulation-amount data (here, the erythema index) based on RGB data obtained from all the pieces of moving image data acquired in time series (130-second data), in which the factor was time data obtained at intervals of 1 second (130 time points for 130 seconds) and the measure was the erythema index computed from the RGB data within the period (at intervals of 1 second) (erythema index computed from the average value of RGB values obtained from extracted 1-second frame data and adjusted in accordance with the moving image data). Through the singular value decomposition, the time-series blood-circulation-amount data based on the RGB data obtained from the moving image data of the faces is decomposed into a plurality of components, and a temporal distribution V and a spatial distribution U of each of the components, and a singular value S indicating the magnitude of each component were calculated. The relationship among them is represented by a formula below. In the formula, V' denotes a matrix in which the rows and columns of V are transposed.

$$X = (U \cdot S) \cdot V^* \quad \text{[Formula. 2]}$$

The temporal distribution V and the spatial distribution U of each component determined using the singular value decomposition were plotted on a graph, and a component waveform diagram and a blood circulation amount distribution diagram of each component were created.

Further, the created component waveform diagram and blood circulation amount distribution diagram of each component were analyzed to identify a component indicating a change in the amount of facial blood circulation, that is, a face RGB change, that reflects emotional activity. The component waveform diagram of each component was analyzed to determine the existence of a correlation between the amplitude of the component waveform of each component and each of the time of providing the rest image and the time of providing two types of emotional images, namely, the positive image and the negative image. Specifically, an evaluation was made of whether a correlation existed between the amplitude shown in the component waveform diagram of each component and the resting period/two types of brain function activation periods.

In this test, as illustrated in FIG. 37, within the period during which captured face image data was acquired, a period of 20 seconds from the start time point of data acquisition to the elapse of 30 seconds, which was the period during which no brain function activation information (emotional image) was presented to the test subjects, and a period of 20 seconds from the elapse of 50 seconds from the start of data acquisition until next brain function activation information (emotional image) was presented were set as the brain "resting time". Further, a period of 20 seconds from the elapse of 30 seconds from the start of data acquisition to the elapse of 50 seconds, which was the period during which the negative image or the like was resented to the test subjects, was set as the "negative emotion activation time". Then, an evaluation was made of the existence of a correlation between the amplitude shown in the component waveform diagram of each component and each of the brain resting time and the negative emotion activation time.

Further, within the period during which captured face image data was acquired, a period of 20 seconds from the elapse of 60 seconds from the start of data acquisition to the elapse of 80 seconds, which was the period during which no brain function activation information was presented to the test subjects, and a period of 20 seconds from the elapse of 100 seconds from the start of data acquisition were set as the brain "resting time". Further, a period of 20 seconds from the elapse of 80 seconds from the start of data acquisition to the elapse of 100 seconds, which was the period during which the positive image or the like was presented to the test subjects, was set as the "positive emotion activation time". Then, an evaluation was made of the existence of a correlation between the amplitude shown in the component waveform diagram of each component and each of the brain resting time and the negative and positive emotion activation times. The determination of the existence of a correlation was performed using statistical correlation analysis. When the significance level ($\alpha$) was 0.05 or less, it was determined that a correlation existed.

The blood circulation amount distribution diagram of each component was analyzed for the presence of a change in the amount of blood circulation in a predetermined face region. The blood circulation amount distribution diagram was created by arranging a spatial distribution U calculated for each pixel at the position of the pixel. An evaluation was made of whether a change in the amount of blood circulation occurred in the nose portion surrounding area and the forehead portion on the blood circulation amount distribution diagram of each component created in the way described above.

The determination of the polarity (plus or minus) of blood-circulation-amount data X is based on the relationship among the values of the spatial distribution U, the singular value S, and the temporal distribution V. Accordingly, in some times, the polarity appears to be reversed on the component waveform diagram and blood circulation amount distribution diagram of each component. For this reason, the polarity is assumed to be excluded from the evaluation of the component waveform diagram and the blood circulation amount distribution diagram.

Figure 38:
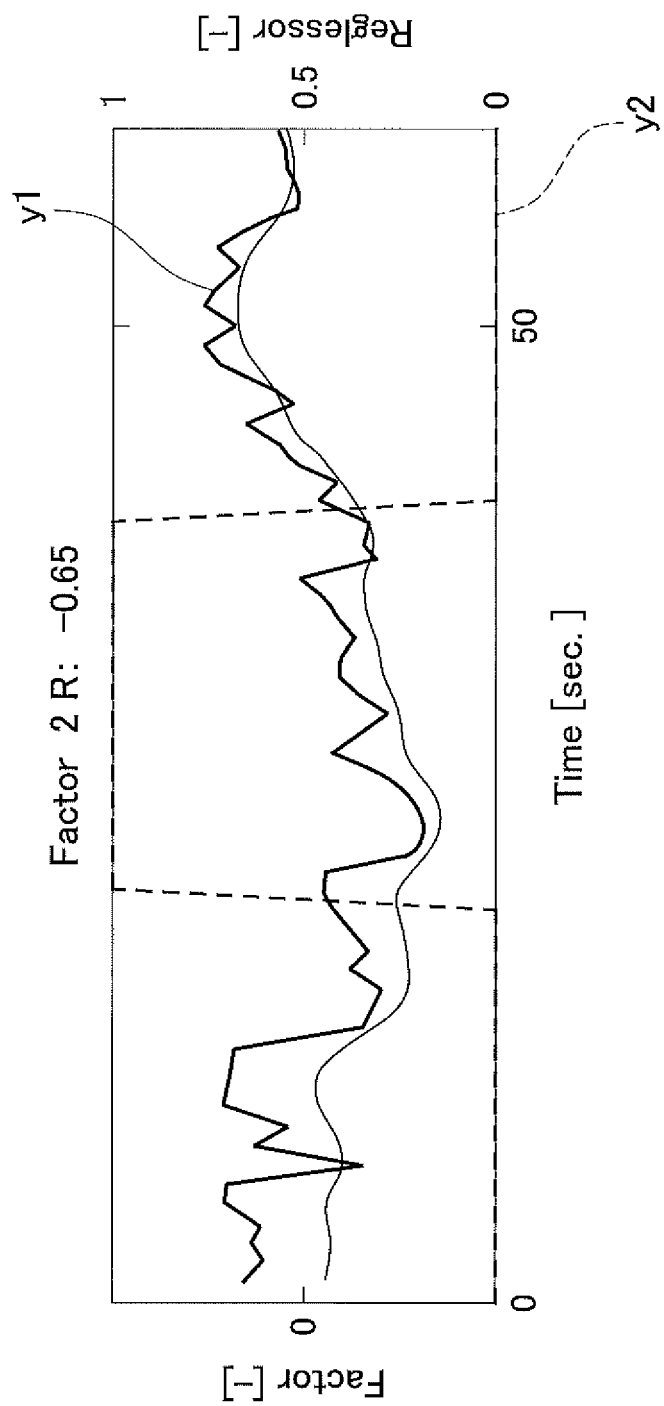
FIG. 38 is a diagram illustrating the waveform of a determination component when a negative image is presented.
Figure 39:
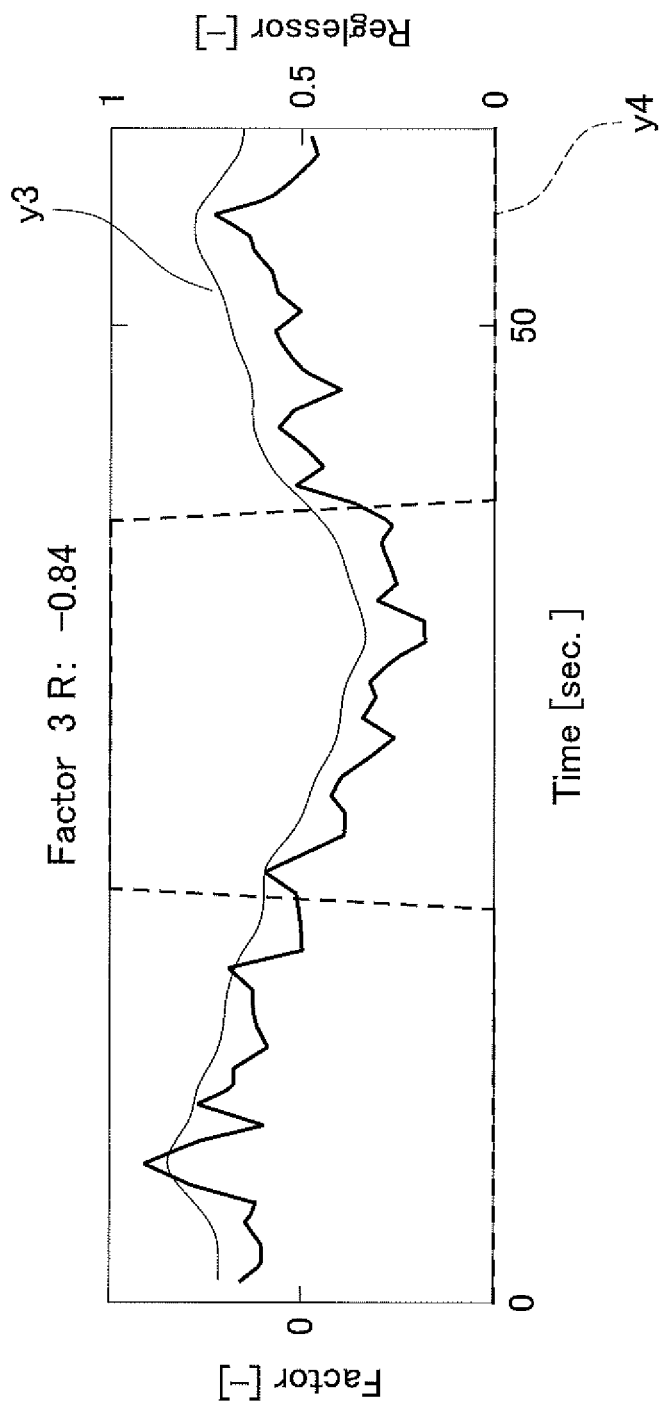
FIG. 39 is a diagram illustrating the waveform of a determination component when a positive image is presented.

Under the conditions described above, the results illustrated in FIGS. 38 and 39 were obtained. FIG. 38 illustrates example waveforms when the negative image was presented. Solid line y1 indicates the waveform of the component 2 for a certain test subject, and dotted line y2 indicates the determination waveform corresponding to the negative image. FIG. 39 illustrates example waveforms when the positive image was presented. Solid line y3 indicates the waveform of the component 3 for the same test subject, and dotted line y4 indicates the determination waveform corresponding to the positive image.

The results described above indicate that a determination component can be extracted in accordance with brain function activation information (emotional image) and that a state of mental illness can be determined.

Note that the present invention is not limited to the embodiment as is. The present invention can be embodied by modifying constituent elements without departing from the gist thereof at the stage of implementation. In the present invention, furthermore, a variety of aspects of the invention can be constituted by appropriate combinations of a plurality of constituent elements disclosed in the embodiment described above. For example, some constituent elements may be omitted from all the constituent elements described in the embodiment. In addition, different embodiments may include appropriate combinations of constituent elements.

The present invention facilitates estimation of brain activity and is thus useful in applications to brain activity visualization devices that visualize the physiological state of a subject on the basis of the brain activity.

What is claimed is:

1. A mental illness determination device comprising:
a processing unit including
a face change information acquisition unit configured to acquire face change information indicating a time-series change in face data of a subject when emotional stimulation information for stimulating any sense or any combination of senses among an auditory sense, an olfactory sense, a gustatory sense, a tactile sense, and a somatic sensation of the subject to change emotion, and being divided into positive information for increasing comfort and negative information for decreasing comfort is provided to the subject;
a mental illness determination unit configured to determine a state of mental illness of the subject on the basis of the face change information; and
a determination component extraction unit configured to extract, as a determination component, a component related to the emotional stimulation information from a plurality of components extracted from the face change information,
each of the plurality of components corresponding to one of a plurality of sets of temporal distributions and spatial distributions,
the determination component extraction unit being further configured to extract the determination component based on a correlation value between a determination waveform corresponding to the emotional stimulation information and each of the plurality of components, and
the face change information being acquired in a region including an area around paranasal sinuses and/or a forehead.

2. The mental illness determination device according to claim 1, wherein
the determination component extraction unit is further configured to extract, as a determination component, a component related to the emotional stimulation information by
analyzing a correlation between the emotional stimulation information and each of the plurality of temporal distributions and
then analyzing the spatial distributions.

3. The mental illness determination device according to claim 1, wherein
a modified wave that takes a human physiological response into account is used as the determination waveform.

4. The mental illness determination device according to claim 3, wherein
the determination waveform is displaced after an elapse of a predetermined time from provision of the emotional stimulation information.

5. The mental illness determination device according to claim 3, wherein
the determination waveform is a rectangular wave.

6. The mental illness determination device according to claim 3, wherein
the determination waveform is generated from a plurality of waveforms, the plurality of waveforms being determined by
calculating a component found to have a correlation among the plurality of components and performing calculation of the component a plurality of times.

7. The mental illness determination device according to claim 1, wherein
the mental illness determination unit is further configured to determine the state of mental illness based on any one or any combination of
an amount of change falling within a predetermined range of a correlation value for the determination component with respect to a reference value,
a value obtained by performing multiple regression analysis on the determination component,
an area of a region for which the determination waveform is generated,
an average value of the determination waveform, and
a value for a center of gravity of the determination waveform.

8. The mental illness determination device according to claim 1, wherein
the processing unit further includes a face change information decomposition unit configured to decompose the face change information into a plurality of components by using singular value decomposition, principal component analysis, or independent component analysis,
each of the plurality of components corresponding to one of a plurality of sets of temporal distributions and spatial distributions.

9. The mental illness determination device according to claim 1, wherein
the processing unit further includes an emotional stimulation information providing unit configured to provide the emotional stimulation information to the subject.

10. The mental illness determination device according to claim 1, wherein
the subject is provided with the emotional stimulation information and emotional image information for stimulating a visual sense of the subject to change emotion.

11. A mental illness determination device comprising:
a processing unit including
a face change information acquisition unit configured to acquire face change information indicating a time-series change in face data of a subject when emotional stimulation information for stimulating a sense of the subject to change emotion is provided;
a determination component extraction unit configured to extract a determination component based on
a correlation value between each of a plurality of components extracted from the face change information, each of the plurality of components corresponding to one of a plurality of sets of temporal distributions and spatial distributions, and
a determination waveform corresponding to the emotional stimulation information; and
a mental illness determination unit configured to determine a state of mental illness of the subject based on the determination component,
the determination waveform being generated from a plurality of waveforms, the plurality of waveforms being determined by calculating a component found to have a correlation among the plurality of components and performing calculation of the component a plurality of times.

12. The mental illness determination device according to claim 11, wherein
a determination information providing device on a network includes a determination information storage unit that stores, as determination information, in association with a state level of mental illness, an amount of change of a correlation value of a determination component calculated for the emotional stimulation information with respect to a reference correlation value of a reference determination component calculated for the emotional stimulation information, the amount of change falling within a predetermined range, and the mental illness determination unit is further configured to calculate a correlation value of the determination component for the emotional stimulation information, and determine a state level of mental illness of the subject on the basis of the calculated correlation value and the determination information.

13. A mental illness determination device comprising:

a face change information acquisition unit configured to acquire face change information indicating a time-series change in face data of a subject when emotional stimulation information for stimulating any sense or any combination of senses among an auditory sense, an olfactory sense, a gustatory sense, a tactile sense, and a somatic sensation of the subject to change emotion, and being divided into positive information for increasing comfort and negative information for decreasing comfort is provided to the subject, the face change information being acquired in a region including an area around paranasal sinuses and/or a forehead;

a mental illness determination unit configured to determine a state of mental illness of the subject on the basis of the face change information; and a determination information providing device on a network including a determination information storage unit that stores, as determination information, in association with a state level of mental illness, an amount of change of a correlation value of a determination component calculated for emotional stimulation information with respect to a reference correlation value of a reference determination component calculated for the emotional stimulation information, the amount of change falling within a predetermined range, and the mental illness determination unit is being further configured to calculate a correlation value of the determination component for the emotional stimulation information, and determine a state level of mental illness of the subject on the basis of the calculated correlation value and the determination information.

* * * * *